(12) United States Patent
Ayares et al.

(10) Patent No.: US 10,149,461 B2
(45) Date of Patent: Dec. 11, 2018

(54) IMMUNOCOMPROMISED UNGULATES

(71) Applicant: Revivicor, Inc., Blacksburg, VA (US)

(72) Inventors: David L. Ayares, Blacksburg, VA (US); Michael Mendicino, Blacksburg, VA (US); Kevin Wells, Colombia, MO (US); Amy S. Dandro, Blacksburg, VA (US)

(73) Assignee: Revivicor, Inc., Blacksburg, VA (US)

( * ) Notice: Subject to any disclaimer, the term of this patent is extended or adjusted under 35 U.S.C. 154(b) by 0 days.

(21) Appl. No.: 14/665,517

(22) Filed: Mar. 23, 2015

(65) Prior Publication Data

US 2016/0278349 A1   Sep. 29, 2016

Related U.S. Application Data

(63) Continuation of application No. 13/092,242, filed on Apr. 22, 2011, which is a continuation of application No. PCT/US2009/062265, filed on Oct. 27, 2009.

(60) Provisional application No. 61/108,742, filed on Oct. 27, 2008.

(51) Int. Cl.
| | | |
|---|---|---|
| *A01K 67/00* | (2006.01) | |
| *A01K 67/027* | (2006.01) | |
| *C07K 14/705* | (2006.01) | |
| *C12N 15/85* | (2006.01) | |
| *G01N 33/50* | (2006.01) | |

(52) U.S. Cl.
CPC ...... *A01K 67/0276* (2013.01); *A01K 67/0273* (2013.01); *A01K 67/0275* (2013.01); *C07K 14/70521* (2013.01); *C12N 15/8509* (2013.01); *G01N 33/5088* (2013.01); *A01K 2217/052* (2013.01); *A01K 2217/075* (2013.01); *A01K 2227/108* (2013.01); *A01K 2267/01* (2013.01); *A01K 2267/0387* (2013.01); *C07K 2319/30* (2013.01); *C12N 2015/8518* (2013.01); *C12N 2015/8527* (2013.01)

(58) Field of Classification Search
CPC ............ A01K 2207/15; A01K 2217/00; A01K 2267/01; A01K 67/0278; A01K 2217/075; A01K 2227/107; A01K 2217/05; A01K 2227/105; A01K 2227/108; A01K 2267/0387; A01K 67/0276; C07K 16/00; C07K 16/06; C07K 14/47; C12N 15/8509; C12N 15/1131; C12N 2015/8518; C12N 2015/8527; G01N 33/68; A61K 2039/505; A61K 2123/00; A61K 38/00
See application file for complete search history.

(56) References Cited

U.S. PATENT DOCUMENTS

| | | | |
|---|---|---|---|
| 5,545,806 A | 8/1996 | Lonberg et al. | |
| 5,545,807 A | 8/1996 | Surani et al. | |
| 5,569,825 A | 10/1996 | Lonberg et al. | |
| 5,591,669 A | 1/1997 | Krimpenfort et al. | |
| 5,612,205 A | 3/1997 | Kay et al. | |
| 5,625,126 A | 4/1997 | Lonberg et al. | |
| 5,625,825 A | 4/1997 | Rostoker et al. | |
| 5,633,425 A | 5/1997 | Lonberg et al. | |
| 5,643,763 A | 7/1997 | Dunn et al. | |
| 5,661,016 A | 8/1997 | Lonberg et al. | |
| 5,721,367 A | 2/1998 | Kay et al. | |
| 5,770,429 A | 6/1998 | Lonberg et al. | |
| 5,789,215 A | 8/1998 | Berns et al. | |
| 5,789,650 A | 8/1998 | Lonberg et al. | |
| 5,814,318 A | 9/1998 | Lonberg et al. | |
| 7,074,983 B2 | 7/2006 | Robl et al. | |
| 7,368,284 B2 * | 5/2008 | Koike ................ | A01K 67/0271 435/191 |
| 7,414,170 B2 | 8/2008 | Robl et al. | |
| 2003/0037347 A1 | 2/2003 | Robl et al. | |
| 2003/0056237 A1 | 3/2003 | Goldsby et al. | |
| 2004/0068760 A1 | 4/2004 | Robl et al. | |
| 2005/0155095 A1 | 7/2005 | Koike | |
| 2005/0223418 A1 | 10/2005 | Koike | |
| 2006/0068479 A1 | 3/2006 | Koike | |
| 2006/0130157 A1 | 6/2006 | Wells et al. | |
| 2008/0040821 A1 | 2/2008 | Robl et al. | |
| 2010/0077494 A1 | 3/2010 | Wells et al. | |

FOREIGN PATENT DOCUMENTS

| | | |
|---|---|---|
| EP | 0 843 961 A1 | 5/1998 |
| WO | WO 91/10741 A1 | 7/1991 |
| WO | WO 92/03918 A1 | 3/1992 |
| WO | WO 92/22645 A1 | 12/1992 |
| WO | WO 92/22647 A1 | 12/1992 |
| WO | WO 92/22670 A1 | 12/1992 |
| WO | WO 93/12227 A1 | 6/1993 |

(Continued)

OTHER PUBLICATIONS

Butler, 2009, Veterinary Immunology and Immunopathology, 128:147-170.*
Baguisi, A., et al., "Production of goats by somatic cell nuclear transfer," *Nat. Biotechnology*, 17(5): 456-461 (May 1999).
Betthauser, J., et al., "Production of cloned pigs from in vitro systems," *Nat. Biotechnology*, 18(10):1055-1059 (Oct. 2000).
Binns, R.M., and Licence, S.T., "Patterns of migration of labelled blood lymphocyte subpopulations: evidence for two types of Peyer's patch in the young pig," *Adv. Exp. Med. Biol.*, 186: 661-668 (1985).

(Continued)

*Primary Examiner* — Valarie E Bertoglio
(74) *Attorney, Agent, or Firm* — King & Spalding

(57) ABSTRACT

Porcine animals, tissue and organs as well as cells and cell lines derived from such animals are provided that lack functional endogenous immunoglobulin loci and are deficient in immunoglobulin expression and B-cells. These animals are useful as model systems for research and for development of new pharmaceutical and biological agents. In addition, methods are provided to prepare such animals.

16 Claims, 13 Drawing Sheets
Specification includes a Sequence Listing.

(56) References Cited

FOREIGN PATENT DOCUMENTS

| WO | WO 94/00569 A1 | 1/1994 |
|---|---|---|
| WO | WO 94/02602 A1 | 2/1994 |
| WO | WO 94/25585 A1 | 11/1994 |
| WO | WO 96/14436 A1 | 5/1996 |
| WO | WO 96/34096 A1 | 10/1996 |
| WO | WO 97/13852 A1 | 4/1997 |
| WO | WO 98/24884 A1 | 6/1998 |
| WO | WO 98/24893 A2 | 6/1998 |
| WO | WO 00/51424 A2 | 9/2000 |
| WO | WO 01/35735 | 5/2001 |
| WO | WO 02/07648 A1 | 1/2002 |
| WO | WO 02/070648 | 9/2002 |
| WO | WO 02/070648 A2 | 9/2002 |
| WO | WO 03/047336 | 6/2003 |
| WO | WO 04/028243 A2 | 4/2004 |
| WO | WO 06/047603 | 5/2006 |
| WO | WO 06/047603 A2 | 5/2006 |

OTHER PUBLICATIONS

Bodey, B., "Human cancer detection and immunotherapy with conjugated and non-conjugated monoclonal antibodies," *Anticancer Res.*, 16(2):661-674 (Mar.-Apr. 1996).
Bonnefoy-Berard, N., and Revillard, J.P., "Mechanisms of immunosuppression induced by antithymocyte globulins and OKT3," *J. Heart Lung Transplant*, 15(5):435-442 (May 1996).
Brown, W.R., and Butler, J.E. "Characterization of a C alpha gene of swine," *Mol. Immunol.*, 31(8):633-642 (Jun. 1994).
Brüggemann, M., et al. "A repertoire of monoclonal antibodies with human heavy chains from transgenic mice," *Proc. Nat'l. Acad. Sci. USA*, 86(17):6709-6713 (Sep. 1989).
Brüggemann, M., et al., "The immunogenicity of chimeric antibodies," *J. Exp. Med.*, 170(6):2153-2157 (Dec. 1, 1989).
Burnett, R. C, et al., "The IgA heavy-chain gene family in rabbit: cloning and sequence analysis of 13 C alpha genes," *EMBO J.*, 8(13):4041-4047 (Dec. 20, 1989).
Butler, J.E., and Brown, W.R., et al , "The immunoglobulins and immunoglobulin genes of swine," *Vet. Immunol. Immunopathol.*, 43(1-3):5-12 (Oct. 1994).
Butler, J.E., et al, "Swine have a single $J_H$, <20 $V_H$ genes and no IgD," Chapter 27 in *Advances in Swine in Biomedical Research*, Tumbleson and Schook, eds. (Plenum Press, New York, 1996), pp. 291-305.
Butler, J.E., et al., "The swine Ig heavy chain locus has a single JH and no identifiable IgD," *Intl. Immunol.*, 8(12):1897-1904 (Dec. 1996).
Casadevall, Arturo, "Passive Antibody Administration (Immediate Immunity) as a Specific Defense Against Biological Weapons" *Emerging Infectious Diseases* (Centers for Disease Control and Prevention (CDC)), 8(8):833-841 (Aug. 2002).
Cendrowski, W., "Antilymphocyte globulin and adrenal steroids in the treatment of multiple sclerosis: short report based on seven cases," *Boll. Ist. Sieroter. Milan*, 58(4):339-343 (Sep. 30, 1979).
Chen, J., et al., "Immunoglobulin gene rearrangement in B cell deficient mice generated by targeted deletion of the JH locus," *International Immunology*, 5(6):647-656 (Jun. 1993).
Choi, T.K., et al., "Transgenic mice containing a human heavy chain immunoglobulin gene fragment cloned in a yeast artificial chromosome," *Nature Genetics*, 4(2):117-123 (Jun. 1993).
Cibelli, J.B., et al., "Cloned transgenic calves produced from nonquiescent fetal fibroblasts," *Science*, 280(5367):1256-1258 (May 22, 1998).
Colby, C., et al., "Antithymocyte immunoglobulin in severe aplastic anemia and bone marrow transplantation," *Ann. Pharmacother.*, 30(10):1164-1174 (Oct. 1996).
Dai, Y., et al., "Targeted disruption of the α1,3-galactosyltransferase gene in cloned pigs," *Nature Biotechnology*, 20:251-255 (Mar. 2002).

Dufour, V, et al., "The sheep Ig variable region repertoire consists of a single VH family," *J. Immunol,.* 156(6):2163-2170 (Mar. 15, 1996).
Dugan, M.J., et al, "ATG plus corticosteroid therapy for acute graft-versus-host disease: predictors of response and survival," *Ann. Hematol.*, 75(1-2):41-46 (Jul.-Aug. 1997).
Fishwild, D.M., et al., "High-avidity human IgG kappa monoclonal antibodies from a novel strain of minilocus transgenic mice," *Nature Biotech.*, 14(7):845-851 (Jul. 1996).
Green, L.L., et al., "Antigen-specific human monoclonal antibodies from mice engineered with human Ig heavy and light chain YACs," *Nature Genetics*, 7(1):13-21 (May 1994).
Green, L.L., and Jakobovits, A., "Regulation of B cell development by variable gene complexity in mice reconstituted with human immunoglobulin yeast artificial chromosomes," *J. Exp. Med.*, 188(3):483-495 (Aug. 3, 1998).
Honjo, T., et al., "Constant-region genes of the immunoglobulin heavy chain and the molecular mechanism of class switching," Chapter 7 in Honjo, T, Alt. F. W. T. H. eds, *Immunoglobulin Genes* (Academic Press, New York, 1989) pp. 123-149.
Jones, P.T.,, et al., "Replacing the complementarity-determining regions in a human antibody with those from a mouse," *Nature*, 321(6069):522-525 (May 29-Jun. 4, 1986).
Kacskovics, I, et al., "Five putative subclasses of swine IgG identified from the cDNA sequences of a single animal," *J Immunol.*, 153(8):3565-3573 (Oct. 15, 1994).
Kastrukoff, L. K.,, et al., "Multiple sclerosis treated with antithymocyte globulin—a five year follow-up," *Can. J Neurol. Sci.*, 5(2):175-178 (May 1978).
Kolber-Simonds, D., et al., "Production of alpha-1,3-galactosyltransferase null pigs by means of nuclear transfer with fibroblasts bearing loss of heterozygosity mutations," *Proc. Natl. Acad. Sci. USA*, 101(19):7335-7340 (May 11, 2004) (Electronic publication May 3, 2004).
Kubota, C., et al., "Six cloned calves produced from adult fibroblast cells after long-term culture," *Proc. Nat'l. Acad. Sci. USA*, 97(3):990-995 (Feb. 1, 2000).
Kuroiwa, Y., et al., "Cloned transchromosomic calves producing human immunoglobulin," *Nature Biotechnology*, 20(9):889-894 (Sep. 2002) (Electronic publication Aug. 12, 2002).
Kuroiwa, Y., et al., "Sequential targeting of the genes encoding immunoglobulin-mu and prion protein in cattle," *Nat. Genet.*, 36(7):775-780 (Jul. 2004) (Electronic publication Jun. 6, 2004).
Lai, L., et al., "Production of α-1,3-galactosyltransferase knockout pigs by nuclear transfer cloning," *Science* 295:1089-1092 (Feb. 8, 2002) and supplementary data, *Science Express*, Jan. 3, 2002.
Lonberg, N., et al., "Antigen-specific human antibodies from mice comprising four distinct genetic modifications," *Nature*, 368(6474):856-859 (Apr. 28, 1994).
Mendez, M.J., et al., "Functional transplant of megabase human immunoglobulin loci recapitulates human antibody response in mice," *Nature Genetics*, 15(2):146-156 (Feb. 1997).
Morrison, S.L.,, et al., "Chimeric human antibody molecules: mouse antigen-binding domains with human constant region domains," *Proc. Natl. Acad. Sci. USA*, 81(21):6851-6855 (Nov. 1984).
Phelps, C.J., et al., "Production of α1,3-galactosyltransferase-deficient pigs," *Science*, 299:411-414 (Jan. 17, 2003).
Polejaeva, I.A., et al., "Cloned pigs produced by nuclear transfer from adult somatic cells," *Nature*, 407:86-90 (Sep. 7, 2000).
Ramsoondar, J.J., et al., "Production of α1,3-galactosyltransferase-knockout cloned pigs expressing human α1,2-fucosyltransferase," *Biol. of Reproduction*, 69:437-445 (online before print Apr. 2, 2003).
Rathbun, G., "Organization and expression of the mammalian heavy-chain variable-region locus," Chapter 4 in *Immunoglobulin Genes*, Honjo, T. Alt. F. W. and Rabbitts, T. H., eds, (Academic Press, New York, 1989), pp. 63-90.
Renner, C.,, et al, "Monoclonal antibodies in the treatment of non-Hodgkin's lymphoma: recent results and future prospects," *Leukemia*, 11( Suppl 2):S55-S59 (1997), miscite as Botti, C., et al., & w/o title.

(56) References Cited

OTHER PUBLICATIONS

Reynaud, C.A., et al., "Formation of the chicken B-cell repertoire: ontogenesis, regulation of Ig gene rearrangement, and diversification by gene conversion," *Adv. Immunol.*, 57:353-378 (1994).

Sendai, Y., et al., "Heterozygous disruption of the alpha1,3-galactosyltransferase gene in cattle," *Transplantation*, (2003) 76(6):900-902 (Sep. 27, 2003).

Sinclair, M.C., et al, "Bovine IgG repertoire is dominated by a single diversified VH gene family," *J. Immunol.*, 159(8): 3883-3889, (Oct. 15, 1997).

Sun, J., et al., "Expressed swine VH genes belong to a small VH gene family homologous to human VHIII," *J. Immunol.*, 153(12): 5618-5627, (Dec. 15, 1994).

Taylor, L.D., et al., "Human immunoglobulin transgenes undergo rearrangement, somatic mutation and class switching in mice that lack endogenous IgM," *Intl. Immunol.*, 6(4):579-591 (Apr. 1994).

Taylor, L.D., et al., "A transgenic mouse that expresses a diversity of human sequence heavy and light chain immunoglobulins," *Nucleic Acids Research*, 20(23):6287-6295 (Dec. 11, 1992).

Tsai, H.F., et al., "Gene conversion-like sequence transfers in a mouse antibody transgene: antigen selection allows sensitive detection of V region interactions based on homology," *International Immunology*, vol. 14(1):55-64 (Jan. 2002).

Tuaillon, N., et al., "Analysis of direct and inverted DJH rearrangements in a human Ig heavy chain transgenic minilocus," *J. Immunol.*, 154(12):6453-6465 (Jun. 15, 1995).

Walker, J. E.,, et al., "A trial of antilymphocyte globulin in the treatment of chronic progressive multiple sclerosis," *J. Neurol. Sci.*, 29(2-4):303-309 (Oct. 1976).

Wilmut, I.,, et al., "Viable offspring derived from fetal and adult mammalian cells," *Nature*, 385(6619):810-813 (Feb. 27, 1997).

Zhao, Y., et al., "Physical mapping of the bovine immunoglobulin heavy chain constant region gene locus," *J. Biol. Chem.*, 278(37):35024-35032 (Sep. 12, 2003) (Electronic publication Jun. 26, 2003).

Zhao, Y., et al., "The porcine Ig delta gene: unique chimeric splicing of the first constant region domain in its heavy chain transcripts.," *J. Immunol.*, 171(3):1312-8 (Aug. 1, 2003).

Zou et al., *J. Immunol.*, 170(3):1354-1361 (Feb. 2003).

Hao-Chih, Tai et al., Progress in xenotransplantation following the introduction of gene-knockout technology, *Transplant International*, vol. 20, No. 2, Feb. 1, 2007, pp. 107-117.

Mendicino, M. et al., "Generation of antibody- and B cell-deficient pigs by targeted disruption of the J-region gene segment of the heavy chain locus," Transgenic Research, Kluwer Academic Publishers, vol. 20, No. 3, Sep. 26, 2010, pp. 625-641.

Ramsoondar J. et al., "Targeted disruption of the porcine immunoglobin kappa light chain locus," *Transgenic Research*, Kluwer Academic Publishers, vol. 20, No. 3, Sep. 26, 2010 pp. 643-653.

Extended European Search Report for EP 09824080.7 dated Feb. 27, 2012.

Patel et al., Animal Pharming for the Production of Pharmaceutical Proteins, Drug Delivery Technology, Apr. 2007, vol. 7, No. 4, pp. 47-53.

International Search Report, for PCT/US09/62265 dated Dec. 9, 2009.

Kuriowa et al., Sequential Targeting of the Genes Encoding Immunoglobulin-μ and Prion Protein in Cattle; (2004) Nat Genet. 36, 775-780.

Kitamura et al., (1991) Nature 350, 423-426.

Couronne et al.; Strategies and Tools for Whole-Genome Alignments; *Genome Research*; vol. 13:73-80; Sep. 4, 2002.

Jeon et al.; *Mol. Cells*; vol. 16, No. 1, ppp113-116; Apr. 10, 2003.

Uenishi et al.; *Nucleic Acids Research*, Aug. 16, 2003; vol. 32; pp. 2-6.

Sutherland et al. Protective Effect of CTLA41G Secreted by Transgenic Fetal Panceas A1 log rafts. Transplantation, 2000, vol. 69, pp. 1806-1812.

Yates et al. Gene therapy of RAG-2-/- mice: sustained correction of the immunodeficiency. 3949. Blood, 2002, vol. 100, pp. 3942.

Su et al. Chlamydia trachomatis Genital Tract Infection of Antibody-Deficient Gene Knockout MiceImmunity, 1997, vol. 65, pp. 1993-1999.

Riberdy et al. Protection against a Lethal Avian Influenza A Virus in a Mammalian System. Journal of Virology, 1999, vol. 73, pp. 1453-1459.

Snyder et al. Protection against Lethal Vaccinia Virus Challenge in HLA-A2 Transgenic Mice by Immunization with a Single CDS+ T-Cell Peptide Epitope of Vaccinia and Variola Viruses J. Virol., 2004, vol. 78, pp. 7052-7060.

Kuroiwa, Yoshimi et al., "Antigen-specific human polyclonal antibodies from hyperimmunized cattle," Nature Biotechnology, vol. 27, No. 2, Feb. 2009, pp. 173-181.

\* cited by examiner

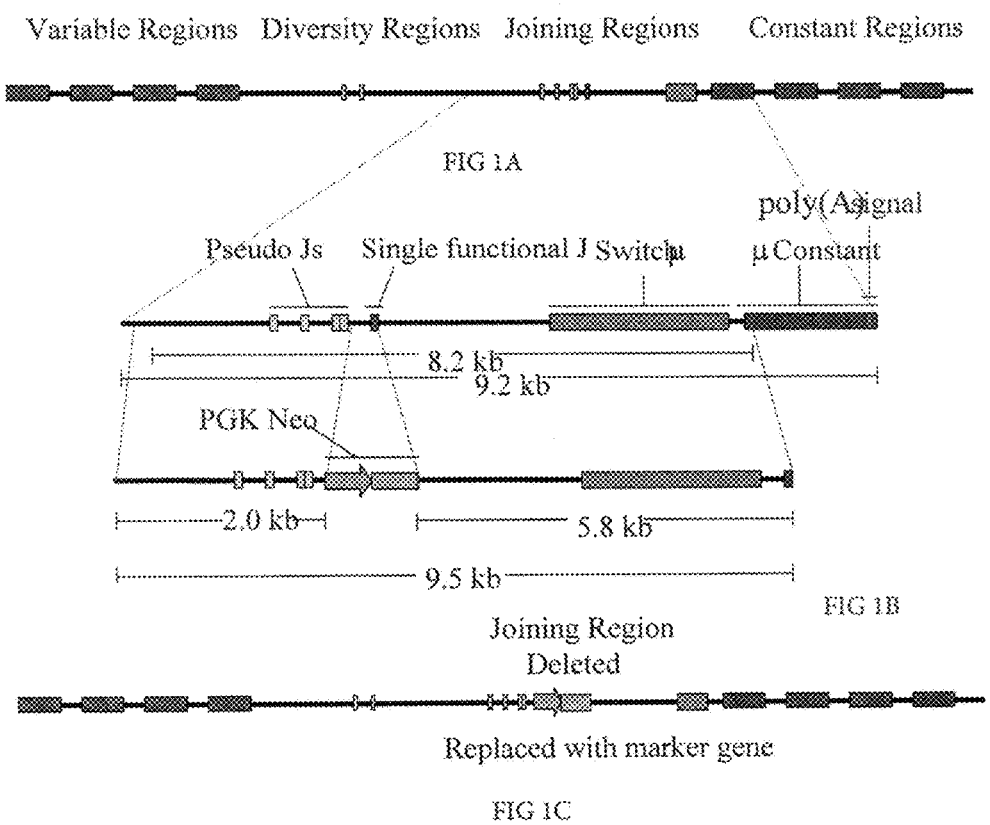

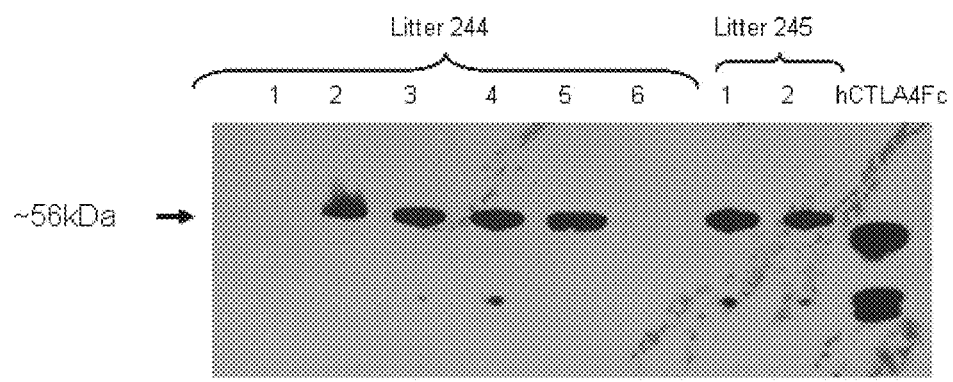
FIGURE 10a
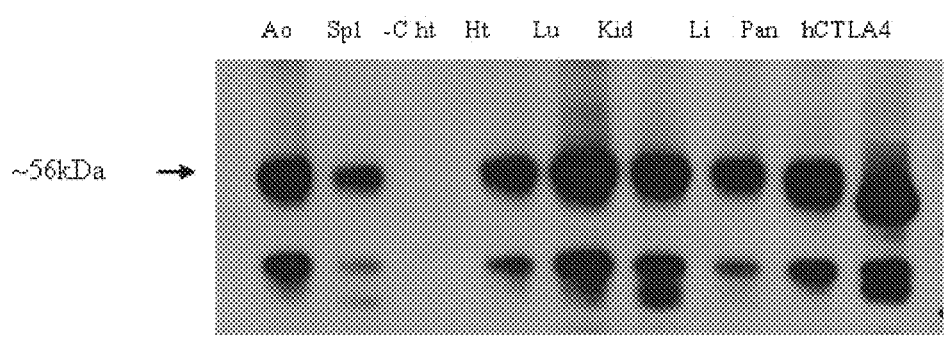
FIGURE 10b
FIGURE 10

IMMUNOCOMPROMISED UNGULATES

CROSS-REFERENCE TO RELATED APPLICATIONS

This application claims priority to U.S. Provisional Application No. 61/108,742, filed Oct. 27, 2008, the disclosure of which is incorporated herein in its entirety.

FIELD OF THE INVENTION

Animals, in particular porcine animals, tissue and organs as well as cells and cell lines derived from such animals are provided that lack functional endogenous immunoglobulin expression. These animals are useful for development of new pharmaceutical and biological agents. In addition, methods are provided to prepare such animals.

BACKGROUND

Models are necessary to study certain disease characteristics. In infectious disease research and vaccine development, it is important to study the cellular and humoral immune response, both together and separately. A 2006 report by the World Health Organization stated "There is evidence suggesting that both cellular and humoral immune responses contribute to protection in humans, and thus the development of laboratory methods and animal models for evaluation of new acellular pertussis vaccines/combinations which detect both types of immune response is necessary."

Mice are the most commonly used research model animal as they are easy to maintain, reproduce readily, and are less costly to house and care for than large animal models. In addition, the ability to readily genetically modify the mouse genome has enabled the creation of many mouse lines with specific phenotypes that are useful for research (Malakoff, 2000). There are numerous existing immune-deficient mouse models.

Immune-deficient mice with spontaneous mutations were first characterized in 1966-68 (nude) and 1983 (scid). The nude mutation causes a failure of most T-cells to develop from their thymic precursor cells although some T-cells, B-cells and NK cells are present. Therefore the nude mouse is not an immunologically inert mouse although it has been used extensively in research. Mice homozygous for the mutation scid (SCID mice) have no B or T lymphocytes, however they do have NK cells. In addition, they often have a "leaky" phenotype in which immunoglobulins are produced (Bosma et al. (1989) Curr Top Microbiol Immunol 152, 1-263, Bosma & Carroll, (1991) Ann. Rev. Immunol. 9, 323-350). A Rag-1 or Rag-2 deficient mouse has also been developed (Mombaerts et al., (1992) Cell 68, 869-877, Shinkai, et al. (1992) Cell 68, 855-867, U.S. Pat. No. 5,859,307). Rag-1 and Rag-2 deficient mice cannot initiate V(D)J rearrangement and therefore lack mature lymphocytes. SCID mutant and Rag-1 and Rag-2 null mice have been widely used in studies with T-cell deficient nude mice in preconditioning, transplantation, and pathogen challenge protocols.

One way the body reacts to antigens is by making antibodies. Antibodies (also called immunoglobulins or "Igs") are proteins that are manufactured by B-cells and circulate in the blood to detect foreign antigens When a vertebrate first encounters an antigen, it exhibits a primary humoral immune response, where B lymphocytes are activated, which generate highly specific antibodies to the antigen and differentiate into "effector" cells to secrete the antibodies. If the animal encounters the same antigen again after a short time the immune response is more rapid and has a greater magnitude than the first response. The initial encounter causes certain B-cells to proliferate and differentiate. The progeny lymphocytes include not only effector cells but also memory cells, which retain the capacity to produce effector cells upon subsequent stimulation by the original antigen. The effector cells live for only a few days but memory cells will remain active for an extended period, even throughout the animal's life, and can be reactivated by a second stimulation with the same antigen. Thus, when an antigen is encountered again, the memory cells quickly produce effector cells, which rapidly produce antibodies.

To examine the role of B-cells in immune responses, mice have been made B-cell deficient by antibody depletion (Gordon, 1979), T-cell reconstitution of SCID mice (Ronchese and Hausmann, 1993; Sunshine et al., (1991) J Exp Med 174, 1653-1656), or by genetic disruption of the Ig locus (Kitamura et al., (1991) Nature 350, 423-426; Jakobovits et al., (1993) Proceedings of the National Academy of Sciences of the United States of America 90, 2551-2555; Chen et al., (1993) Int Immunol 5, 647-656).

The use of B-cell deficient mice, in side by side studies with wild type mice, SCID, Rag-1 or Rag-2 null mice, has allowed T-cell (cellular) responses to be studied separately from B-cell (humoral) responses for many diseases. For example, immune responses by B-cell deficient mice have been studied for the bacterial diseases *Salmonella*, *Bodetella*, and *Tularemia* (Ugrinovic et al., (2003) Infect Immun 71, 6808-6819, Leef et al., (2000) J Exp Med 191, 1841-1852, Chen et al., (2004) Microbial pathogenesis 36, 311-318.), the viral disease Smallpox (Wyatt et al., (2004) Proceedings of the National Academy of Sciences of the United States of America 101, 4590-4595), the parasitic diseases *Leishmania* (Brown and Reiner, (1999) Infect Immun 67, 266-270, Miles et al., (2005) J Exp Med 201, 747-754, Ronet et al., (2008) J Immunol 180, 4825-4835.) and Malaria (Weidanz et al., (2005) Exp Parasitol 111, 97-104), and for inflammatory bowel disease (Ma et al., (1995) J Exp Med 182, 1567-1572). In fact, papers detailing production of three different lines of Hc KO, B-cell deficient mice produced in the 1990's (Kitamura et al., (1991) Nature 350, 423-426; Chen et al., (1993) Int Immunol 5, 647-656; Jakobovits et al., (1993) Proceedings of the National Academy of Sciences of the United States of America 90, 2551-2555) have to date been cited by over 1000 scientific publications (source: Google Scholar search engine). In addition to studying the basic immune response to a pathogenic challenge, these animals have also been used to test vaccines for effectiveness (Wyatt et al., (2004) Proceedings of the National Academy of Sciences of the United States of America 101, 4590-4595). The use of B-cell deficient transgenic mice also allowed for the determination of the critical role for B-cells in the systemic autoimmunity phenotype associated with lupus (Chan et al., (1999) Immunol Rev 169, 107-121).

Although mice are used extensively, there are few examples in the literature for the use of other species as immuno-deficient animal models for human disease research. Most of these are very specialized in relation to the animal chosen and the disease being modeled. Rats have been immunosuppressed by administration of dexamethasone prior to infection with *aspergillus* to test the efficacy of prophylactic drugs (Ulmann et al., (2007) J Antimicrob Chemother 60, 1080-1084). A ligated germ-free rabbit appendix was utilized to study inflammatory responses related to inflammatory bowel disease (Shanmugam et al., (2005) Inflamm Bowel Dis 11, 992-996).

PCT Publication No. WO06/047603 and related U.S. Patent publications U.S. 2006/0130157 and U.S. 2008/0026457, which are incorporated in their entirety herein, describe certain ungulate immunoglobin germline gene sequence arrangement as well as genomic sequences encoding the heavy chain locus of ungulate immunoglobulin, and ungulate cells, tissues and animals that lack an allele of a native heavy or light chain immunoglobulin gene and specifically describe methods of targeted disruption of individual porcine Ig gene sequences as well as replacement with human Ig genes. The resulting genetically modified animals are described as useful to produce human polyclonal antibodies as therapeutics.

Mice have been genetically modified to make them more appropriate models for infection with human pathogens. For example, species-specific ligand/receptors exist for infections such as Listeria. These receptors have been introduced as transgenes into mice. These transgenic mice then express the receptor and become more susceptible hosts as the pathogen can bind to its known receptor (which is not present in wild type mice) and initiate infection (see Lecuit and Cossart et al., (2002) Trends Mol Med 8, 537-542). Although such mouse models have proven useful, researchers still stress that there are technical limitations, as animals which normally develop listeriosis are not classical laboratory animals such as the rat or mouse, but rather farm animals (Lecuit, (2007) Microbes Infect 9, 1216-1225).

There remains a need for an animal system that can be effectively used to model human disorders, and in particular to model immune deficiencies. There also remains a need for an effective animal model to develop novel therapeutics. There further remains a need for a large animal model to develop and produce proteins, in particular human immunoglobulins, without endogenous contamination.

It is an object of the invention to provide improved animal systems to model human disorders and to allow production of certain therapeutic agents, particularly certain biologics.

SUMMARY OF THE INVENTION

There remains a need for a true large animal model that lacks a humoral immune response and that can effectively model human infectious disease pathologies. The present invention provides animals, in particular ungulates, and most particularly pigs, lacking production of immunoglobulin, methods of producing such animals and uses thereof.

In one embodiment, animals are provided that lack expression of a native immunoglobulin gene, including expressing only a non-functional version of such gene. In certain embodiments, the animals lack functional native immunoglobulin protein expression. In certain embodiments, these animals exhibit reduced, have altered, or lack B-cell production. In some embodiments, the animals lack native immunoglobulins and lack B-cells. In certain embodiments, the animals lack or have altered or reduced humoral responses. In certain embodiments, the animal has a targeted disruption in a gene encoding a heavy chain in its genome. In certain embodiments, the animal has a targeted disruption in a gene encoding a heavy chain joining region in its genome. In certain embodiments, the animal has a targeted disruption in both alleles of a heavy chain joining region in its genome. In certain embodiments, the animal has a targeted disruption in a gene encoding a light chain in its genome.

In one embodiment, the animals provided herein are useful as research animal models for infectious disease and immunology research. The immuno-deficient animals described herein that lack production of native immunoglobulins and, typically, lack production of B-cells, can be used in scientific research to study, for example, mechanisms of protective immunity or to investigate and test treatments against disorders in a veterinary context. In certain embodiments, the animals described herein can be used to study whether a viral infection such as porcine reproductive and respiratory syndrome (PRRS) requires B-cells for virulence. Furthermore, these animals can be used to study diseases found in humans. In certain embodiments the animals are used to develop therapies for human diseases in lieu of more commonly used rodent models. Large animals, such as ungulates, and most particularly pigs, are physiologically more similar to humans than are rodents, and thus provide a more effective model for studying disease mechanisms and for development and study of potential human therapeutics. Therefore, in one embodiment, a method of testing disease mechanisms is provided comprising exposing an animal that lacks native immunoglobulins and lacks B-cell production to an agent that causes a disease and analyzing a response in the animal. The response can be a cellular response or it can be a gross physiological response, such as lifespan.

In other embodiments, the animals do not express native immunoglobulins but do express at least one immunoglobulin from a different species. In particular embodiments, the animals express at least one human immunoglobulin. In some embodiments, the animals are useful for production of xenogenous biologics, and in particular embodiments are useful for production of xenogenous antibodies.

In some embodiments, the animals are useful for the production of therapeutic intravenous immunoglobulin (IVIG) for use in treatment of human disorders. In some embodiments, blood products derived from animals described herein are provided, and in particular embodiments, IVIG derived from an animal described herein is provided. In some embodiments, an IVIG specific to a particular antigen or selection of antigens is provided. In certain embodiments, such an IVIG is provided in a dose at least sufficient to provide passive immunity for one week, or for at least two weeks, or for at least three weeks, or for at least four weeks. In certain embodiments, the IVIG is a fully human IVIG.

In some embodiments, animals and methods of their production and use are described that lack production of native immunoglobulin and are additionally deficient in at least one additional gene native to the animal. In particular embodiments, the animals are also deficient in a glycosyltransferase enzyme. In particular embodiments, the enzyme is α(1,3)galactosyltransferase.

In yet other embodiments, the animals lacking production of endogenous immunoglobulins additionally express at least one recombinant protein.

BRIEF DESCRIPTION OF THE FIGURES

FIG. 1 illustrates the architecture of the porcine Hc locus. FIG. 1A is a schematic of the porcine Hc locus. FIG. 1B shows the region to be targeted is magnified, and the targeting vector is shown below it. FIG. 1C shows the targeted porcine Hc locus, with the only functional JH region deleted.

FIG. 2 shows southern blot screening strategy for litters and representative blot.

FIG. 4 is an analysis of transcription of different Ig isotypes in spleen.

FIG. 10 shows western blot analyses of pCTLA4-Ig transgenic pig tail lysates (FIG. 10A) and pCTLA4-Ig transgenic pig organs from a representative transgenic animal (FIG. 10B) under reduced and denaturing conditions. Bands were detected with anti-human IgG1 antibody.

DETAILED DESCRIPTION

Figure 2A:
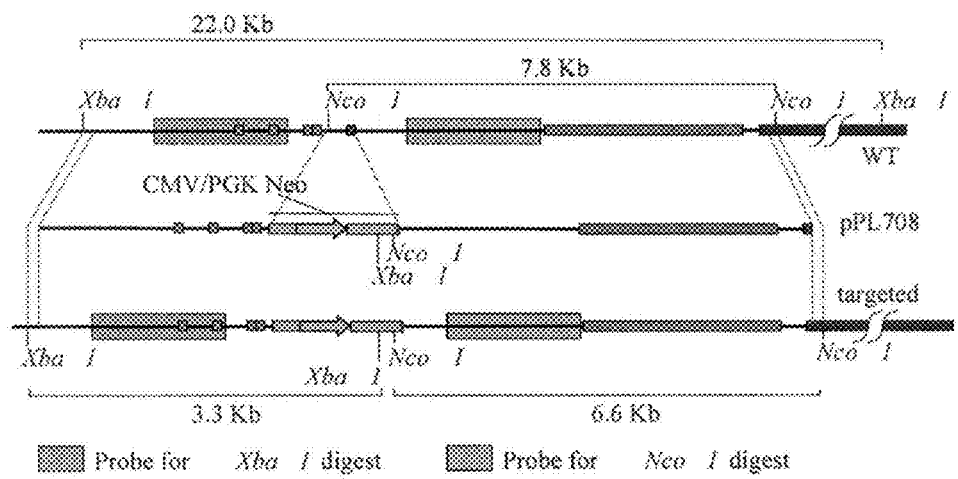
FIG. 2A shows two different Southern blots digested with either XbaI or NcoI enzyme and subsequent probed. The corresponding band sizes for a wild-type (WT) or targeted (K.O.) allele are shown on the top and bottom, respectively.

Animals, and in particular porcine animals are provided that have a homozygous gene targeted deletion that eliminates production of functional endogenous antibodies. In some embodiments, the animal includes a gene targeted deletion of the single functional J region of the porcine heavy chain (Hc) Ig gene.

Surprisingly, it was found that animals which have a Hc null (−/−) phenotype lack endogenous immunoglobulin expression (both cell surface and secreted) and lack B-cells. The animals of this invention are useful as immunocompromised large animal models, since they lack productive immunoglobulin rearrangement and subsequent Ig expression. Typically, these animals are devoid of B-cells, and, therefore, lack humoral responses. Presently, there are no large animal models lacking a humoral response. This is a major advance compared to rodent models, since rodent immunological models often do not translate to larger mammals, such as pigs and humans.

To the extent that a gene is "disrupted" for purposes of the present invention, the gene can be disrupted by deletion of all or a portion of an intron or exon or both, by mutation of one or more nucleotides within the gene, by interruption or insertion of one or more exogenous sequences within the gene or by inactivation of the gene, such as by mutation, deletion, insertion or interruption of a promoter or enhancer sequence within the genome.

Animals of the Invention

In one embodiment, the animals provided herein are useful as research animal models for infectious disease and immunology research. Typically, the animals, and particularly porcine animals described herein, lack immunoglobulin production. In some embodiments, the animals are immunocompromised by lacking B-cells.

Animals of the invention are typically ungulates. Ungulates are hoofed animals and include horse, zebra, donkey, cattle/bison, rhinoceros, camel, hippopotamus, goat, water buffalo, pig, sheep, giraffe, okapi, moose, deer, tapir, antelope, and gazelle. In particular embodiments, the animal is a pig. Because of its anatomic and physiological similarity to humans, the pig has become an important research animal (Book and Bustad 1974, Almond, 1996). Pigs share a higher sequence homology to human for most Ig genes than do mice. Furthermore, they are omnivorous like humans, have a similar gut flora, and are infected by closely-related viral and bacterial pathogens. For these reasons, they are often used to model human intestinal diseases.

In one embodiment, the animal, and in particular the porcine animal, lacks or has only a disrupted porcine heavy chain gene locus. In certain embodiments, the animal lacks a gene encoding a heavy chain joining region in its genome. In specific embodiments, the animal does not produce any heavy chain proteins. In one embodiment, the animal, and in particular the porcine animal, lacks or has a disrupted porcine light chain gene locus. In specific embodiments, the animal does not produce any light chain proteins.

Antibody molecules are assembled from combinations of variable gene elements, and the possibilities resulting from combining the many variable gene elements in the germline enable the host to synthesize antibodies to an extraordinarily large number of antigens. Each antibody molecule consists of two classes of polypeptide chains: light chains (L-chains), which can be either kappa (κ) or lambda (λ) L-chains; and heavy chains (H-chains). The H and L chains join together to define a binding region for an epitope on the antigen.

In nature, a single antibody molecule has two identical copies of the L chain and two of the H chain. Each of the chains includes a variable region (V) and a constant region (C). The variable region is the antigen-binding site of the molecule and therefore is specific to a particular epitope. To achieve diverse antigen recognition, the DNA that encodes the variable region undergoes gene rearrangement. The constant region amino acid sequence, on the other hand, is specific for a particular isotype of the antibody and for the host which produces the antibody, and thus does not undergo rearrangement.

The DNA sequence encoding a complete V region is generated by the somatic recombination of separate gene segments. The V domain of an immunoglobulin heavy or light chain is encoded by more than one gene segment. For the light chain, the V domain is encoded by two separate DNA segments. The first segment encodes the first 95-101 amino acids of the light chain and is termed a V gene segment because it encodes most of the V domain. The second segment encodes the remainder of the V domain (up to 13 amino acids) and is termed a joining or J gene segment. The joining of a V and a J gene segment creates a continuous exon that encodes the whole of the light-chain V region. To make a complete immunoglobulin light-chain messenger RNA, the V-region exon is joined to the C-region sequence by RNA splicing after transcription.

A heavy-chain V region is encoded in three gene segments. In addition to the V and J gene segments (denoted VH and JH to distinguish them from the light-chain VL and JL), there is a third gene segment called the diversity or DH gene segment, which lies between the VH and JH gene segments. The process of recombination that generates a complete heavy-chain V region occurs in two separate stages. In the first, a DH gene segment is joined to a JH gene segment; then a VH gene segment rearranges to DJH to make a complete VH-region exon. As with the light-chain genes, RNA splicing joins the assembled V-region sequence to the neighboring C-region gene.

Diversification of the antibody repertoire occurs in two stages: primarily by rearrangement ("V(D)J recombination") of Ig V, D and J gene segments in precursor B-cells resident in the bone marrow, and then by somatic mutation and class switch recombination of these rearranged Ig genes when mature B-cells are activated. Immunoglobulin somatic mutation and class switching are central to the maturation of the immune response and the generation of a "memory" response.

The mechanism of DNA rearrangement for variable domains to achieve antigen recognition is similar for the variable region of both the H and L-chain genomic loci, although only one joining event is needed to generate a L-chain gene whereas two are needed to generate a complete H-chain gene. The most common mechanism of rearrangement involves the looping-out and deletion of the DNA between two gene segments. This occurs when the coding sequences of the two gene segments are in the same orientation in the DNA. A second mode of recombination can occur between two gene segments that have opposite transcriptional orientations. This mode of recombination is less common, although for the V-κ and J-κ gene segments, up to half of which in humans have opposite orientations, such rearrangements can account for up to half of all joins.

The genomic loci of antibodies are very large and they are located on different chromosomes. The immunoglobulin gene segments are organized into three clusters or genetic loci: the κ, λ, and heavy-chain loci. Each is organized slightly differently. For example, in humans, immunoglobulin genes are organized as follows. The λ light-chain locus is located on chromosome 22 and a cluster of Vλ gene segments is followed by four sets of Jλ gene segments each linked to a single Cλ gene. The light-chain locus is on chromosome 2 and the cluster of Vκ gene segments is followed by a cluster of Jκ gene segments, and then by a single Cκ gene. The organization of the heavy-chain locus, on chromosome 14, resembles that of the κ locus, with separate clusters of VH, D H, and JH gene segments and of CH genes. The heavy-chain locus differs in one important way: instead of a single C-region, it contains a series of C regions arrayed one after the other, each of which corresponds to a different isotype. There are five immunoglobulin heavy chain isotypes: IgM, IgG, IgA, IgE and IgD. Generally, a cell expresses only one at a time, beginning with IgM. The expression of other isotypes, such as IgG, can occur through isotype switching.

The joining of various V, D and J genes is a random event that results in approximately 50,000 different possible combinations for VDJ(H) and approximately 1,000 for VJ(L). Subsequent random pairing of H and L chains brings the total number of antibody specificities to about $10^7$ possibilities. Diversity is further increased by the imprecise joining of different genetic segments. Rearrangements occur on both DNA strands, but only one strand is transcribed (due to allelic exclusion). Only one rearrangement occurs in the life of a B-cell because of irreversible deletions in DNA. Consequently, each mature B-cell maintains one immunologic specificity and is maintained in the progeny or clone. This constitutes the molecular basis of the clonal selection; i.e., each antigenic determinant triggers the response of the pre-existing clone of B lymphocytes bearing the specific receptor molecule. The primary repertoire of B-cells, which is established by V(D)J recombination, is primarily controlled by two closely linked genes, recombination activating gene (RAG)-1 and RAG-2.

Over the last decade, considerable diversity among vertebrates in both Ig gene diversity and antibody repertoire development has been revealed. Rodents and humans have five heavy chain classes, IgM, IgD, IgG, IgE and IgA, and each have four subclasses of IgG and one or two subclasses of IgA, while rabbits have a single IgG heavy chain gene but 13 genes for different IgA subclasses (Burnett, R. C et al. EMBO J 8:4047; Honjo, In Honjo, T, Alt. F. W. T. H. eds, Immunoglobulin Genes p. 123 Academic Press, New York). Swine have at least six IgG subclasses (Kacskovics, I et al. 1994 J Immunol 153:3565), but no IgD (Butler et al. 1996 Inter. Immunol 8:1897-1904). A gene encoding IgD has only been described in rodents and primates. Diversity in the mechanism of repertoire development is exemplified by contrasting the pattern seen in rodents and primates with that reported for chickens, rabbits, swine and the domesticated Bovidae. Whereas the former group have a large number of VH genes belonging to seven to 10 families (Rathbun, G. In Hongo, T. Alt. F. W. and Rabbitts, T. H., eds, Immunoglobulin Genes, p. 63, Academic press New York), the VH genes of each member of the latter group belong to a single VH gene family (Sun, J. et al. 1994 J. Immunol. 1553:56118; Dufour, V et al. 1996, J Immunol. 156:2163). With the exception of the rabbit, this family is composed of less than 25 genes. Whereas rodents and primates can utilize four to six JH segments, only a single JH is available for repertoire development in the chicken (Reynaud et al. 1989 Adv. Immunol. 57:353). Similarly, Butler et al. (1996 Inter. Immunol 8:1897-1904) hypothesized that swine may resemble the chicken in having only a single JH gene. These species generally have fewer V, D and J genes; in the pig and cow a single VH gene family exists, consisting of less than 20 gene segments (Butler et al, Advances in Swine in Biomedical Research, eds: Tumbleson and Schook, 1996; Sinclair et al, J. Immunol. 159: 3883, 1997). Together with lower numbers of J and D gene segments, this results in significantly less diversity being generated by gene rearrangement. However, there does appear to be greater number of light chain genes in these species. Similar to humans and mice, these species express a single K light chain but multiple λ light chain genes. However, these do not seem to affect the restricted diversity that is achieved by rearrangement. For a recent review on Ig, antibody repertoire and B-cell development in swine as compared to other species, see Butler Dev Comp Immunol. Sep. 17, 2008 (advance online publication, currently in press).

Since combinatorial joining of more than 100 VH, 20-30 DH and four to six JH gene segments is a major mechanism of generating the antibody repertoire in humans, species with fewer VH, DH or JH segments must either generate a smaller repertoire or use alternative mechanisms for repertoire development. Ruminants, pigs, rabbits and chickens utilize several mechanisms to generate antibody diversity. In these species there appears to be an important secondary repertoire development, which occurs in highly specialized lymphoid tissue such as ileal Peyer's patches (Binns and Licence, Adv. Exp. Med. Biol. 186: 661, 1985). Secondary repertoire development occurs in these species by a process of somatic mutation which is a random and not fully understood process. The mechanism for this repertoire diversification appears to be templated mutation, or gene conversion (Sun et al, J. Immunol. 153: 5618, 1994) and somatic hypermutation.

Gene conversion is important for antibody diversification in some higher vertebrates, such as chickens, rabbits and cows. In mice, however, conversion events appear to be infrequent among endogenous antibody genes. Gene conversion is a distinct diversifying mechanism characterized by transfers of homologous sequences from a donor antibody V gene segment to an acceptor V gene segment. If donor and acceptor segments have numerous sequence differences then gene conversion can introduce a set of sequence changes into a V region by a single event. Depending on the species, gene conversion events can occur before and/or after antigen exposure during B-cell differentiation (Tsai et al. International Immunology, Vol. 14, No. 1, 55-64, January 2002).

Somatic hypermutation achieves diversification of antibody genes in all higher vertebrate species. It is typified by the introduction of single point mutations into antibody V(D)J segments. Generally, hypermutation appears to be activated in B-cells by antigenic stimulation.

In specific embodiments, the animal lacks or only has a disrupted heavy chain gene locus in its genome but has no alterations of its T cell levels from an animal that does not have a disrupted heavy chain gene locus. In other embodiments, the animal further is deficient in T-cell production. The animal can have reduced T cells or lack T-cell production through a mutation in its genome, such as through a disruption or deletion of a RAG-1 or RAG-2 gene. RAG-1 deficient pigs are described in Patent Publication Nos. US 2005-0155094 and WO 03/066855. Porcine Rag-2 gene cDNA sequences can be found in GenBank accession numbers NM001128481 and AB091391. T cell defective animals, particularly pigs, can be made by disruption of the FOXN1 (also known as the whn) gene. In other embodiments, the animal lacks T cells through pharmacological or surgical intervention. Such an animal can lack or be deficient in both B and T cells.

A B-cell deficient animal is useful in scientific research, for example to study mechanisms of protective immunity or to investigate and test treatments against disorders in a veterinary context. For example, the B-cell deficient animals can be used to study whether a viral infection such as porcine reproductive and respiratory syndrome (PRRS) requires B-cells for virulence. Furthermore, these animals can be used to study diseases found in humans and to develop therapies in lieu of more commonly used rodent models. Large animals, such as ungulates, and most particularly pigs, are physiologically more similar to humans than are rodents, and thus provide a more effective model for studying disease mechanisms and for development and study of potential human therapeutics. For example, these model animals can be used to studies diseases including but not limited to Porcine Reproductive and Respiratory Syndrome (PRRS), influenza, HIV, CMV, hepatitis, malaria, the effect of toxins, and antibiotic resistant bacteria. Therefore, in one embodiment, a method of testing disease mechanisms is provided comprising exposing an animal deficient in B-cell production to an agent that causes a disease and analyzing a response in the animal. The response can be a cellular response or it can be a gross physiological response, such as lifespan.

In certain alternate embodiments, the animals are at least partially deficient in B-cells. In certain embodiments, the animals have less than 50% of normal levels of immunoglobulins. In other embodiments, the animals have less than 30%, less than 20% or less than 10% of the level of immunoglobulins in plasma from a wild type pig. In certain embodiments, the level of B-cells when compared to a wild type pig is reduced by 80%, or by 90%, or by 95% or by 98% or by 99% or by 100%.

In other embodiments, the animals express at least one immunoglobulin from a different species, but do not express immunoglobulin native to the animal. In particular embodiments, the animals express at least one human immunoglobulin. In other embodiments, the animals express at least one xenogenous immunoglobulin, but do not express an immunoglobulin native to the animal. In particular embodiments, the animals express at least one human immunoglobulin.

In other embodiments, the animals can be further genetically modified to express xenogenous immunoglobulin loci. In an alternative embodiment, porcine animals are provided that contain a xenogeous immunoglobulin locus. In one embodiment, the xenogeous immunoglobulin loci can be a heavy and/or light chain immunoglobulin or fragment thereof. In another embodiment, the xenogenous immunoglobulin loci can be a kappa chain locus or fragment thereof and/or a lambda chain locus or fragment thereof. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B-cells to produce xenogenous immunoglobulin in response to exposure to one or more antigens.

Further aspects of the present invention provide ungulates and ungulate cells that lack at least one allele of a functional region of an ungulate heavy chain, kappa light chain and/or lambda light chain locus produced according to the processes, sequences and/or constructs described herein, which are further modified to express at least part of a human antibody (i.e. immunoglobulin (Ig)) locus. In additional embodiments, porcine animals are provided that express xenogenous immunoglobulin. This human locus can undergo rearrangement and express a diverse population of human antibody molecules in the ungulate. These cloned, transgenic ungulates provide a replenishable supply of human antibodies (such as polyclonal antibodies), which can be used for therapeutic, diagnostic, purification, and other clinically relevant purposes. In one particular embodiment, artificial chromosomes (ACs), such as yeast or mammalian artificial chromosomes (YACS or MACS) can be used to allow expression of human immunoglobulin genes into ungulate cells and animals. All or part of human immunoglobulin genes, such as the Ig heavy chain gene (human chromosome 414), Ig kappa chain gene (human chromosome 2) and/or the Ig lambda chain gene (chromosome 22) can be inserted into the artificial chromosomes, which can then be inserted into ungulate cells. In further embodiments, ungulates and ungulate cells are provided that contain either part or all of at least one human antibody gene locus, which undergoes rearrangement and expresses a diverse population of human antibody molecules.

In some embodiments, animals and methods of their production and use are described that do not produce antibodies native to the animal species and are additionally deficient in at least one additional endogenous gene or gene product. In particular embodiments, the animals are also deficient in a glycosyltransferase enzyme. In particular embodiments, the enzyme is α(1,3)galactosyltransferase. Animals or cells lacking expression of functional immunoglobulin can be modified to eliminate the expression of at least one allele of the alpha-1,3-galactosyltransferase gene, the CMP-Neu5Ac hydroxylase gene (see, for example, U.S. Pat. No. 7,368,284), the iGb3 synthase gene (see, for example, U.S. Patent Publication No. 2005-0155095), and/or the Forssman synthase gene (see, for example, U.S. Patent Publication No. 2006-0068479). Because humans and old world primates lack this enzyme (as would α(1,3) galactosyltransferase deficient pigs), antibodies derived from animals that lack a functional α(1,3)galactosyltransferase enzyme could have a decreased clearance time or increased antibody half life. This would be an enhancement over other ungulate derived antibodies.

In yet other embodiments, the animals lacking production of antibodies native to the animal species additionally express at least one recombinant protein. In additional embodiments, the animals discloses herein can also contain genetic modifications to express fucosyltransferase and/or sialyltransferase.

Methods of Use

B cell-deficient mice have long been used in research, and multiple lines have been generated (Kitamura, D., Roes, J., Kuhn, R., & Rajewsky, K. (1991) Nature 350, 423-426; Jakobovits, A. et al. (1993) Proc. Natl. Acad. Sci. U.S.A 90, 2551-2555). In side-by-side studies with wild-type mice and T- and B cell-deficient mouse models, T cell (cellular) responses can be separately studied from B cell (humoral) responses for many diseases. For example, immune responses by B cell-deficient mice have been studied for the bacterial diseases *Salmonella* (Ugrinovic, S., Menager, N., Goh, N., & Mastroeni, P. (2003) Infect. Immun. 71, 6808-6819), Bodetella (Leef, M., Elkins, K. L., Barbic, J., & Shahin, R. D. (2000) J. Exp. Med. 191, 1841-1852) and Tularemia (Chen, W., KuoLee, R., Shen, H., & Conlan, J. W. (2004) Microb. Pathog. 36, 311-318), the viral diseases Smallpox (Wyatt, L. S., Earl, P. L., Eller, L. A., & Moss, B. (2004) Proc. Natl. Acad. Sci. U.S.A 101, 4590-4595) and rotavirus (Franco, M. A. & Greenberg, H. B. (1995) J. Virol. 69, 7800-7806), the parasitic diseases *Leishmania* (Ronet, C. et al. (2008) J. Immunol. 180, 4825-4835) and Malaria (Weidanz, W. P. et al. (2005) Exp. Parasitol. 111, 97-104), inflammatory diseases such as Inflammatory Bowel Disease (Ma, A. et al. (1995) J. Exp. Med. 182, 1567-1572), and autoimmune diseases such as lupus (Chan, O. T., Madaio, M. P., & Shlomchik, M. J. (1999) Immunol. Rev. 169, 107-121). In addition to studying the basic immune response to a pathogenic challenge, these animals have also been used to test vaccines for effectiveness (Wyatt, 2004, McNeal, M. M. et al. (2002) J. Virol. 76, 560-568). Unfortunately, results from rodent immunological models often do not translate to larger mammals, such as livestock and humans (Forsberg, E. J. (2005) Reprod. Fertil. Dev. 17, 59-68, Melo, E. O., Canavessi, A. M., Franco, M. M., & Rumpf, R. (2007) J. Appl. Genet. 48, 47-61, Butler, J. E. & Sinkora, M. (2007) Immunol. Res. 39, 33-51, Rogers, C. S. et al. (2008) J. Clin. Invest 118, 1571-1577, Butler, J. E. et al. (2009) Vet. Immunol. Immunopathol. 128, 147-170).

Pigs are much better models than mice for many research applications. They are monogastrics, with gastric physiology and dietary requirements similar to humans. Their mucosal immunity is also similar to humans. They are of sufficient size to ensure ample sampling of tissues and blood for analysis. They are able to be raised in germ free environments without colostrum, therefore lacking any confounding effects from passive maternal immunity. Because they are born in litters, there are enough animals to provide for age matched controls in study groups.

Unlike mouse models, there is no in utero transfer of maternal Ab in swine but due to some de novo synthesis, piglets are not born totally agammaglobulinemic (Butler, J. E. et al. (2001) J. Immunol. 167, 3239-3249). Since there are fetal models in this species for viral and immunological veterinary studies (see review Butler, et al., 2009) it would be beneficial if B cell-deficient fetal piglets were available for similar studies. Also unlike mice, piglets are precocial allowing them to be reared separated from their mothers in germ-free or gnotobiotic isolator facilities (Butler, J. E. & Sinkora, M. (2007) Gordon and Pesti, 1971). The isolator piglet is an in vivo model for the fetal immune system since piglets maintained under such conditions remain, immunologically, like fetal animals (Butler, J. E. et al. (2000) Immunology 100, 119-130, Butler, J. E. et al. (2005) Immunol. 175, 6772-6785, Sinkora, M. & Butler, J. E. (2009) Dev. Comp Immunol. 33, 273-283). Thus far, this model has proven valuable in: i) understanding the immunopathology caused by the pandemic PRRSV in which pathology is related to polyclonal B cell activation (Lemke, C. D. et al. (2004) J. Immunol. 172, 1916-1925, Butler, J. E., Wertz, N., Weber, P., & Lager, K. M. (2008) J. Immunol. 180, 2347-2356), ii) swine influenza research (Vincent, A. L. et al. (2006) Vet. Microbiol. 118, 212-222), iii) studying the pathology of colibacillosis (Erume, J. et al. (2008) Infect. Immun. 76, 3141-3149), and iv) understanding the intestinal absorption of maternal Igs (Butler et al., 2009). By rearing B cell-deficient piglets gnotobiotically, the relative roles of B cells and Ab production, versus T cells, in the control of postnatal viral and bacterial disease, might be better understood for veterinary and agricultural applications.

Anatomic, nutritional, physiological and immunological similarities to humans have made the pig an important biomedical research animal (Butler et al., 2009, Rogers, C. S. et al. (2008) Science 321, 1837-1841). For example, pigs are omnivorous like humans, have a similar gut flora and are infected by closely-related viral and bacterial pathogens. For most major enteropathogens, such as *Helicobactor pylori*, *Shigella flexneri* and *Salmonella enterica*, mouse animal models do not reproduce the tropism, immunopathology, or other hallmarks of the corresponding human infections (Goodwin, C. S., Armstrong, J. A., & Marshall, B. J. (1986) J. Clin. Pathol. 39, 353-365, Lecuit, M. & Cossart, P. (2002) Trends Mol. Med. 8, 537-542, Lecuit, M. (2007) Microbes. Infect. 9, 1216-1225). The dietary and mucosal similarity of humans and swine has resulted in their specific use as models for digestive, respiratory and/or infectious diseases, and allergies (Charley, B., Riffault, S., & Van, R. K. (2006) Ann. N. Y. Acad. Sci. 1081, 130-136, Saif, L. J. et al. (1996) Arch. Virol. Suppl 12, 153-161, Souza, M. et al. (2007) J. Virol. 81, 9183-9192, Krakowka, S., Eaton, K. A., Rings, D. M., & Morgan, D. R. (1991) Rev. Infect. Dis. 13 Suppl 8, S681-S685, Yuan, L. et al. (1996) J. Virol. 70, 3075-3083, Cheetham, S. et al. (2006) J. Virol. 80, 10372-10381, Dawson, H. et al. (2009) Infect. Immun. 77, 2576-2587, Helm, R. M. et al. (2002) J. Allergy Clin. Immunol. 109, 136-142). A prominent and recently described example of a porcine model that more fully recapitulated a human condition is the knock-out piglet model for cystic fibrosis (Rogers, C. S. et al. (2008) Science 321, 1837-1841).

Swine are infected by closely-related viral and bacterial pathogens often to the extent that they can serve as zoonotic reservoirs for human pathogens, and thus play a critical role in public health threats worldwide (Taylor, L. H., Latham, S. M., & Woolhouse, M. E. (2001) Philos. Trans. R. Soc. Lond B Biol. Sci. 356, 983-989). The H1N1 Influenza A virus (swine flu) is a current, relevant and prominent zoonotic example (Neumann, G., Noda, T., & Kawaoka, Y. (2009) Nature 459, 931-939). Many zoonotic agents have potential bioterrorism applications as well (Mattix, M. E. et al. (2006) Clin. Lab Med. 26, 445-89). Thus, the availability of Ab- and B cell-deficient piglets should serve as valuable as models for certain human diseases and would aid in vital vaccine development by helping to ascribe protective immunity to T or B cells, or both.

Prior to the present invention, no genetically modified pigs had been produced with an immune deficient phenotype. Therefore, there remained a need for a true B-cell deficient large animal model that lacks a humoral immune response and that can effectively model human infectious disease pathologies.

Ideally, to understand the pathology of human infection, an animal model in which the infectious agent has as much as possible the same cell and tissue tropism as in humans is required. In addition, the model should allow observation of the same direct effects and indirect immunopathological damage that occurs in humans (Lecuit, 2007). For most major human enteropathogens, such as *Heliobactor pylori*, *Shigella flexneri*, *Salmonella enterica*, mouse animal models reproducing all the hallmarks of the corresponding human infections are not available." (Lecuit and Cossart, 2002). Mizgerd and Skerrit (2008) detailed multiple concerns in using the mouse due to its differences from human. An infectious agent, such as a virus or bacteria, or an antigen of any sort, can be given to a pig as described herein and the immune response of that pig to the infectious agent can be compared to a wild type pig or a T cell-depleted pig. Methods include infusion of infectious agent by a variety of routes, including intranasal, inhalation, intravenous, parentaral, transdermal, intravaginal, and the like, over a variety of time period. The infections agent may be administered in combination or alternation with other agents including drugs or antibodies or cellular depleting reagents. To analyze the immune response of the pig, methods include histology and histopathology for course of disease progression, flow cytometry for relevant cell populations in relevant tissues (e.g. lymph node and spleen), molecular biological methods for gene expression studies such as expression of cytokines and chemokines and other immunological mediators such as coagulants and complement proteins, and immunoassays such as MLRs, cytotoxicity, proliferation or apoptosis assays to quantitatively measure effects on immune system in the host. To test the utility of a product, such as an antiviral or antibacterial agent against a pathogen, the product can be administered to the animal before, at the same time, or after the pathogen is administered, where the same analytical methods are utilized to determine utility of a product.

Many emerging infectious diseases, including those with potential bioterrorism applications, are zoonoses. Zoonoses are "diseases that can be transmitted from wild and domestic animals to humans and are public health threats worldwide." (Kahn, 2006). Taylor and others identified 1415 infectious agents and found that 868 (61%) could be transmitted between animals and humans (Taylor et al., (2001) Philos Trans R Soc Lond B Biol Sci 356, 983-989). They found that zoonotic diseases were twice as likely to be associated with emerging or newly discovered infections, as compared to non-zoonotic pathogens, and that viruses and protozoa were the zoonotic pathogens most likely to emerge. RNA viruses, in particular, have been identified as highly likely to emerge (Cleaveland et al., (2001) Philos Trans R Soc Lond B Biol Sci 356, 991-999). These agents include West Nile Virus, avian influenza virus, hantavirus, and severe acute respiratory syndrome (SARS)-associated coronavirus. Pigs are already a known reservoir for many of these emerging infectious agents, including influenza and SARS coronavirus (Charley et al., (2006) Ann N Y Acad Sci 1081, 130-136), and have been identified as a possible host reservoir for zoonotic transmission of noravirus and sapovirus (Wang et al., (2006) J Clin Microbiol 44, 2057-2062), and hepatitis E (Meng (2003) Curr Top Microbiol Immunol 278, 185-216). Therefore, the pig is likely the best model animal for studying emerging zoonotic diseases.

Pigs, unlike mice, give birth to precocial offspring and can therefore be separated from their birth mothers and put into germfree isolators. This allows for their exposure/supply of passive immunity, commensal bacteria, dietary antigen and pathogen exposure to be controlled by the experimenter (Butler and Sinkora, (2007) Immunol Res 39, 33-51). Specific definitions of these types of animals are provided and detailed in a review by Gordon and Pesti, (1971) Bacteriol Rev 35, 390-429 and include:

Gnotobiote (Gnotobiotic animal) are derived by aseptic cesarean section (or sterile hatching of eggs) and are reared and continuously maintained with germfree techniques under isolator conditions and in which the composition of any associated fauna and flora, if present, is fully defined by accepted current methodology. A gnotobiote maintained under isolator conditions in intentional association with one or more known types of microorganisms is considered of a 'defined flora'. A gnotobiote which is free from all demonstrable associated forms of life including bacteria, viruses, fungi, protozoa and other saprophytic or parasitic forms is considered 'germ free'.

Cesarean derived colostrum deprived (CDCD) piglets (which do not receive any maternally derived immunity), raised under specific pathogen free (SPF) conditions, have been used, for example, to test the pathogenicity of viral isolates (Halbur et al., (1996) J Vet Diagn Invest 8, 11-20) and to evaluate vaccines (Welter and Welter, (1990) Veterinary microbiology 22, 179-186). However, such CDCD pigs are not gnotobiotes.

Prior to the present invention, these types of pigs were the only models for infectious disease studies that could not be well modeled in mice. These models have associated problems. It is extremely difficult, labor intensive and expensive to maintain a gnotobiotic pig facility. Sterility of the germ free host cannot be assured by absolute criteria. Latent viruses may remain undetected. All feed must be sterilized and pathogen free. There is therefore possible confounding of scientific results due to the variations in feed quality, as rigorous steam sterilization can cause nutrients in the feed to become degraded. There also may be effects due to lack of gut flora in an animal that normally has gut flora involved in digestion. Animals may have a lower metabolic rate, experience diarrhea, and eat or drink more due to the missing microbial regulatory function (Gordon and Pesti, 1971).

Although a challenging research model to work with, several groups have done extensive research on human disease pathology using gnotobiotic pigs. Gnotobiotic pigs have been used as a model for human rotavirus infection. The advantages of using this model (over mouse and rabbit) are detailed by Saif et al., (1996) Arch Virol Suppl 12, 153-161 and include: infection in other species is usually only subclinical, gnotobiotic pigs remain susceptible to infection by human rotavirus for up to 6 weeks of age, pigs closely resemble humans in gastrointestinal physiology (they are both monogastric) and mucosal immune development, and confounding of the research results by the presence of other pathogens can be prevented in the gnotobiotic environment. Major advances from these studies include: 1) the adaption of the first human rotavirus to cell culture after passage and amplification in piglets, 2) delineation of the independent roles of the two rotavirus outer capsid proteins (VP4 and VP7) in induction of neutralizing antibodies and cross-protection; and 3) recognition of a potential role for a nonstructural protein in addition to VP4 and VP7, in rotavirus virulence (Saif et al., (1996) Arch Virol Suppl 12, 153-161). In another study intestinal IgA antibody secreting cells were identified as a correlate of protective active immunity in this animal model (Yuan et al., (1996) J Virol 70, 3075-3083).

Noravirus is the leading cause of food-borne illness in the United States (Mead et al., (1999) Emerg Infect Dis 5, 607-625). Strains of porcine noravirus that are genetically and antigenically related to those which infect humans have recently been found to occur in swine, raising concerns that swine may be potential reservoirs for this virus (Wang et al., (2006) J Clin Microbiol 44, 2057-2062). Due to the lack of an animal model for human noravirus infection (previous studies utilized samples from infected human volunteers), and difficulties growing it in cell cultures, research on immunity and vaccines for this virus has been hampered in the past. Gnotobiotic pigs, infected with a human noravirus strain were recently found to be capable of infection by human rotavirus strains (Cheetham et al., (2006) J Virol 80, 10372-10381), and have been used as a model to study intestinal and systemic antibody responses and cytokine profiles (Souza et al., (2007) J Virol 81, 9183-9192). Findings from such studies should be useful to researchers designing vaccination strategies for this virus in humans.

Gnotobiotic piglets were used as an animal model for gastritis induced by *Heliobactor pylori* (Krakowka et al., (1991) Rev Infect Dis 13 Suppl 8, S681-685). Previously, oral challenge experiments in conventional animal species, including rabbits, rats, mice, guinea pigs, and hamsters failed to provide an appropriate model for the human pathology of *H. pylori* (Goodwin et al., (1986) J Clin Pathol 39, 353-365; Morgan et al., (1988) Abstracts of the annual meeting of the American Society for Microbiology, B195, 162). Gnotobioitic piglets colonized with a bacterial strain of human origin were found to closely mimic acute infection and inflammation seen in humans. The complexity of the immune response was studied in the infected piglets. In addition this animal model allowed for the identification of bacterial virulence factors and the evaluation of chemotherapeutic drugs for this condition.

Although gnotobiotic and germ free pigs have been useful models in immunologic studies of human disease, there remains the limitation that although these animals are immunologically naïve, they are not immune-deficient, and therefore cannot be utilized to study the various components of the immune response (such as B and T cell responses) separately. B cell-deficient large animal models are a valuable tool for studies aimed at determining whether protection from veterinary or human infectious agents is mediated by humoral or cellular immunity, or both. In infectious disease research and vaccine development, it is important to study the cellular and humoral immune response, both together and separately.

The only large animal which has been generated with an Ig heavy chain gene "knocked out" was the disruption of the Heavy mu gene in cattle produced by sequential nuclear transfer (Kuriowa et al., (2004) Nat Genet 36, 775-780). Although these animals were shown by RT-PCR to lack expression of the mu heavy chain, there was no information reported on their immunological phenotype; whether they were B-cell deficient or immune-deficient in any way due to their specified disruption of the mu gene. More recently, the same group reported that cows express two functional HC loci (Kuroiwa, Y. et al. (2009) Nat. Biotechnol. 27, 173-181) in contrast to the one functional locus expressed in mice (Kitamura, D., Roes, J., Kuhn, R., & Rajewsky, K. (1991)), pigs (Butler et al., 2009, Butler, J. E. et al. (2009) Dev. Comp Immunol. 33, 321-333) and humans (Yel, L. et al. (1996) N. Engl. J. Med. 335, 1486-1493). They showed that both bovine loci (four alleles in total) must be targeted for the cattle to become Ab- and B cell-deficient (Kuroiwa, Y. et al. (2009)).

It should be noted that in homozygous mice with a similar targeted disruption of an exon of the mu gene (Kitamura et al., (1991) Nature 350, 423-426), some mice are reported to produce some B-cells using a constant (C) gene other than Ig mu (Infectious Disease Research and the Laboratory Mouse, A Jackson Laboratory Resource Manual, available online at http://jaxmice.jax.org/manual/infectious_disease_manual.pdf, p 20.

Before the pigs provided by the present invention, there was no way to model many disease pathologies and effectively study the cellular and humoral immune responses separately post challenge and/or following therapeutic treatment. Although B-cell deficient mice are available, mice cannot model many human diseases as effectively as pigs. In addition, currently available immuno-deficient mouse models may produce some B-cells. The increased emphasis on the threat and study of emerging zoonotic disease, and in developing countermeasures to infectious pathogens used in bioterrorism, driven by the public, governments and worldwide agencies such as the World Heath Organization (WHO), has created a need for better animal models for studying infectious human disease pathology, and for development and testing of vaccines. In addition, the increase in the number of humans with partially suppressed immune systems, from things such as HIV infection, and the aging of the "baby boomer" population, has created a need to study the ability of vaccines to effectively protect these high-risk groups. Large animal models to study in vivo immune responses in fields such as autoimmune disease and transplant rejection are also needed. The Hc null B-cell deficient pigs produced and described herein, and methods of their use for infectious disease and immunology research provided herein will fulfill these needs.

Heavy chain joining region deficient (JH −/−) pig models can have special applications in veterinary research on such agents as PRRSV, and other infections. PRRSV is a worldwide pandemic pig disease, which causes over a billion dollar per year impact on the commercial pig industry. Since PRRSV seems to cause virulence by subverting humoral immunity through polyclonal activation of the pre-immune B cell repertoire (Lemke, C. D. et al. (2004) J. Immunol. 172, 1916-1925, Butler, J. E et al. (2008) J. Immunol. 180, 2347-2356), the B-cell deficient pig model will likely be of significant value in disease etiology. Theoretically, if B cell-deficient piglets are reared in isolator units to protect them from bacterial infection, the degree to which polyclonal B cell activation contributes to PRRSV-induced immune dysregulation could be assessed. These same piglets could serve as a model to determine the relative role of cell-mediated and Ab-mediated viral immunity not only to PRRSV but other troublesome neonatal swine viruses such as influenza, parvovirus, and circovirus, which would have valuable agricultural applications (Butler, J. E. & Sinkora, M. (2007)). These include aiding in vaccination strategies for pigs (Halbur, P. G. et al. (1996) J. Vet. Diagn. Invest 8, 11-20, Welter, M. W. & Welter, C. J. (1990) Vet. Microbiol. 22, 179-186).

There are also a number of human diseases that cannot be properly modeled in rodents. For example, cystic fibrosis (CFTR) knockout mice fail to develop any clinically relevant form of cystic fibrosis (Rogers et al., 2008). In the case of cystic fibrosis, there are always questions of whether bacterial infections like *Pseudomonas* that are often associated are primary or secondary effects. Indeed, it is yet unclear whether some CF pathology or CF protection is Ab mediated, a question that could be answered in a pig model that is both CFTR −/− and JH −/−. Since pigs resemble humans in gastrointestinal physiology, dietary requirements and mucosal immunity, they have also been utilized as gnotobiotic models in studies involving rotavirus (Saif, L. J. et al. (1996), Yuan, L. et al. (1996) J. Virol. 70, 3075-3083, Yuan, L. et al. (2008) Vaccine 26, 3322-3331), norovirus (Souza, M. et al. (2007) J. Virol. 81, 9183-9192, Cheetham, S. et al. (2006) J. Virol. 80, 10372-10381) and sapovirus (Wang, Q. H. et al. (2006) J. Clin. Microbiol. 44, 2057-2062), and both *Heliobacter pylori* (Krakowka, S., Eaton, K. A., Rings, D. M., & Morgan, D. R. (1991) Rev. Infect. Dis. 13 Suppl 8, S681-S685) and *Escherichia coli* infections (Gunzer, F., et al. (2003) Methods Mol. Med. 73, 307-327). Therefore, the roles of humoral immunity in these and other infections, as well as in potential zoonotic infections (e.g. swine flu (Neumann, G., Noda, T., & Kawaoka, Y), Hepatitis E (Meng, X. J. (2003)), can be addressed with the JH −/− pigs (Butler, J. E. & Sinkora, M. (2007), Butler et al., 2009).

The Hc null pigs may be used in side by side experimental studies with porcine animal models which are T-cell deficient or defective, such as animals with a disruption or mutation of the nude gene (also known as whn or FOXN1), and/or in combination with animal models which are both B and T-cell deficient, such as animals with a disruption or mutation of the RAG-1 or RAG-2 gene, which are termed SCID animals. These animal models have been described in the mouse and used widely in research (Pantelouris, 1968, Nehls et al., (1994) Nature 372, 103-107, Mombaerts et al., (1992) Cell 68, 869-877, Shinkai, et al., (1992) Cell 68, 855-867).

Pig animal models such as nude and SCID are produced using techniques as described herein. In addition, animals may be made T-cell deficient using surgical methods, by treatment with immunosuppressive agents, or a combination of methods. Methods of T-cell depletion (TCD) include, for example, surgical removal of thymus, physical methods such as lectin agglutination, and treatment with monoclonal antibodies. TCD methods have been described in the literature, and are commonly used to suppress cellular immune responses in human clinical transplantation (Hertenstein et al., (1998) BioDrugs 9, 105-123). For example the drug Campath® (alemtuzumab, Bayer HealthCare Pharmaceuticals Inc., Wayne, N.J.) is a monoclonal antibody which recognizes >95% of human T cells, B-cells, and monocytes, and fixes human complement causing lysis of lymphocytes (Hale et al., (1986) Transplantation 42, 308-311). Another drug used clinically is Thymoglobulin®, a gamma immune globulin obtained from rabbits immunized with T-cells (Genzyme Corp., Cambridge Mass.). Agents with similar biologic activity and T cell depleting function can be used in pigs. A Hc null pig, subsequently treated to deplete it's T-cells, will have a SCID phenotype. As an alternative, drugs can also be administered which prevent T-cell activation, such as CTLA4-Ig (commercially available as Orencia® (abatacept, Bristol-Myers Squib Company, NY).

Use of the Hc null pigs in side by side comparison studies with other pig models, such as nude and SCID pigs, or pigs treated to lack a T-cell response, or which have a compromised T-cell response (such as CTLA4-Ig transgenic pigs) allow cellular and humoral immune responses to be studied separately. Studies comparing T and B-cell deficient (SCID and RAG-1 or RAG-2 null) mice with T cell deficient nude mice in preconditiong, transplantation and pathogen challenge protocols have been widely conducted (Croy et al., (2001) Comp Med 51, 300-313). The pig animal models provided herein are an improvement over the mouse models currently available in many research areas, and will provide opportunity for advanced immunological study in a large animal model; a more appropriate model for human pathological conditions.

In certain embodiments, the invention provides a use of animals lacking a heavy chain gene locus to test responses to pathogenic challenge or prophylactic or therapeutic treatment comprising challenging an animal lacking a heavy chain gene locus, and in particular a heavy chain joining region, with a pathogen and comparing a response of such animal to the pathogen with a response of an animal with a disruption of a FOXN1 and/or RAG-1 or RAG-2 gene challenged by the same pathogen. These studies can be useful as side-by-side studies to elucidate the roles of the various parts of the immune response (B and T cells) following a pathogenic challenge and/or following prophylactic treatments.

To the extent that a medicament is provided prophylactically, the medicament is provided to a host or animal at risk of a symptom or disorder who is not yet suffering from or exhibiting the symptom or disorder. The medicaments being tested can include small molecule therapeutics or biologics. In the context of the invention, to test prophylactic use of a therapeutic, the therapeutic is typically administered prior to administration of a pathogenic agent or initiation of a disease or disorder by other means to the animal lacking immunoglobulin expression. To the extent that a medicament is administered therapeutically, the medicament is administered to a host suffering from a symptom or disorder. In the context of the invention, to the extent that an agent is tested for therapeutic use, the agent is typically administered concurrently with or subsequent to administration of a pathogenic agent or initiation of a disease or disorder by other means.

In certain instances, the invention provides a model to test a vaccine. In certain embodiments, the vaccine can be a DNA based vaccine, an antibody or antibody fragment, or a live, attenuated or dead virus. The vaccine can include an immunostimulatory sequence.

In additional embodiments, methods of producing xenogenous antibodies are provided, wherein the method can include: (a) administering one or more antigens of interest to an animal, particularly an ungulate and most particularly a pig, whose cells comprise one or more artificial chromosomes and lack any expression of functional endogenous immunoglobulin, each artificial chromosome comprising one or more xenogenous immunoglobulin loci that undergo rearrangement, resulting in production of xenogenous antibodies against the one or more antigens; and/or (b) recovering the xenogenous antibodies from the ungulate. In one embodiment, the immunoglobulin loci can undergo rearrangement in a B-cell.

In other embodiments, the animals express at least one immunoglobulin from a different species, but do not express immunoglobulin native to the animal, i.e., endogenous immunoglobulin. In particular embodiments, the animals express at least one human immunoglobulin. In some embodiments, the animals are useful for the production of therapeutic intravenous immunoglobulin (IVIG) for use in treatment of human disorders. In some embodiments, blood products derived from animals described herein are provided, and in particular embodiments, IVIG derived from an animal described herein is provided. IVIG derived from the animals of the invention typically contains pooled antibodies not native to the species of animal of the invention that are extracted from the plasma of a donor animal. IVIG's can be used as treatment in primary immune deficiencies such as, in a non-limiting example, X-linked gammaglobulinemia, hypogammaglobulinemia and acquired compromised immunity conditions (secondary immune deficiencies), featuring low antibody levels; in treatment of inflammatory and autoimmune diseases; and in treatment of acute infections. IVIG is given as a plasma protein replacement therapy (IgG) for immune deficient patients, such as people with cystic fibrosis or lupus, who have decreased or abolished antibody production capabilities. In these immune deficient patients, IVIG derived from the animals of the invention can be administered to maintain adequate antibodies levels to prevent infections and confers a passive immunity.

In some embodiments, an IVIG specific to a particular antigen or selection of antigens is provided. In certain embodiments, such an IVIG is provided in a dose at least sufficient to provide passive immunity for one week, or for at least two weeks, or for at least three weeks, or for at least four weeks. In certain embodiments, the IVIG is a fully human IVIG. In some embodiments, only a cell or tissue or organ of the animal is utilized.

Methods of Preparation of Genetically Modified Animals
Preparation of Genetically Modified Cells In one aspect of the present invention, an ungulate, such as a pig or a cow, can be prepared by a method in accordance with any aspect of the present invention. To produce the immunodeficient animals described herein, the present invention provides cells that have been genetically modified to inactivate at least one immunoglobulin locus, and in particular an immunoglobulin locus in the heavy chain, and most particularly an immunoglobulin locus in a joining region of a heavy chain. In particular embodiments, the cells are provided in which both alleles of the heavy chain joining region have been disrupted.

Animal cells that can be genetically modified can be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus, or adult animal. In one embodiment of the invention, cells can be selected from the group consisting of, but not limited to, epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islets of Langerhans cells, blood cells, blood precursor cells, bone cells, bone precursor cells, neuronal stem cells, primordial stem cells, adult stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B-cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, squamous epithelial cells, osteocytes, osteoblasts, and osteoclasts. In one alternative embodiment, embryonic stem cells can be used.

In a particular embodiment, the cells can be fibroblasts or fibroblast-like cells having a morphology or a phenotype that is not distinguishable from fibroblasts, or a lifespan before senescense of at least 10 or at least 12 or at least 14 or at least 18 or at least 20 days, or a lifespan sufficient to allow homologous recombination and nuclear transfer of a non-senescent nucleus; in one specific embodiment, the cells can be fetal fibroblasts. Fibroblast cells are a suitable somatic cell type because they can be obtained from developing fetuses and adult animals in large quantities. These cells can be easily propagated in vitro with a rapid doubling time and can be clonally propagated for use in gene targeting procedures.

In one embodiment, immunoglobulin genes can be genetically targeted in cells through homologous recombination. Homologous recombination permits site-specific modifications in endogenous genes and thus novel alterations can be engineered into the genome. In homologous recombination, the incoming DNA interacts with and integrates into a site in the genome that contains a substantially homologous DNA sequence. In non-homologous ("random" or "illicit") integration, the incoming DNA is not found at a homologous sequence in the genome but integrates elsewhere, at one of a large number of potential locations. In general, studies with higher eukaryotic cells have revealed that the frequency of homologous recombination is far less than the frequency of random integration. The ratio of these frequencies has direct implications for "gene targeting" which depends on integration via homologous recombination (i.e. recombination between the exogenous "targeting DNA" and the corresponding "target DNA" in the genome). A number of papers describe the use of homologous recombination in mammalian cells. Illustrative of these papers are Kucherlapati et al., Proc. Natl. Acad. Sci. USA 81:3153-3157, 1984; Kucherlapati et al., Mol. Cell. Bio. 5:714-720, 1985; Smithies et al, Nature 317:230-234, 1985; Wake et al., Mol. Cell. Bio. 8:2080-2089, 1985; Ayares et al., Genetics 111:375-388, 1985; Ayares et al., Mol. Cell. Bio. 7:1656-1662, 1986; Song et al., Proc. Natl. Acad. Sci. USA 84:6820-6824, 1987; Thomas et al. Cell 44:419-428, 1986; Thomas and Capecchi, Cell 51:503-512, 1987; Nandi et al., Proc. Natl. Acad. Sci. USA 85:3845-3849, 1988; and Mansour et al., Nature 336:348-352, 1988. Evans and Kaufman, Nature 294:146-154, 1981; Doetschman et al., Nature 330:576-578, 1987; Thomas and Capecchi, Cell 51:503-512, 4987; Thompson et al., Cell 56:316-321, 1989.

The present invention can use homologous recombination to inactivate an immunoglobulin gene in cells, such as the cells described above. The DNA can comprise at least a portion of the gene(s) at the particular locus with introduction of an alteration into at least one, optionally both copies, of the native gene(s), so as to prevent expression of functional immunoglobulin. The alteration can be an insertion, deletion, replacement or combination thereof. When the alteration is introduced into only one copy of the gene being inactivated, the cells having a single unmutated copy of the target gene are amplified and can be subjected to a second targeting step, where the alteration can be the same or different from the first alteration, usually different, and where a deletion, or replacement is involved, can be overlapping at least a portion of the alteration originally introduced. In this second targeting step, a targeting vector with the same arms of homology, but containing a different mammalian selectable markers can be used. The resulting transformants are screened for the absence of a functional target antigen and the DNA of the cell can be further screened to ensure the absence of a wild-type target gene.

Nucleic acid targeting vector constructs can be designed to accomplish homologous recombination in cells. In one embodiment, a targeting vector is designed using a "poly(A) trap". Unlike a promoter trap, a poly(A) trap vector captures a broader spectrum of genes including those not expressed in the target cell (i.e fibroblasts or ES cells). A polyA trap vector includes a constitutive promoter that drives expression of a selectable marker gene lacking a polyA signal. Replacing the polyA signal is a splice donor site designed to splice into downstream exons. In this strategy, the mRNA of the selectable marker gene can be stabilized upon trapping of a polyA signal of an endogenous gene regardless of its expression status in the target cells. In one embodiment, a targeting vector is constructed including a selectable marker that is deficient of signals for polyadenylation. One targeting or recombination arm of the vector (flanking one side of the selectable marker) includes at least a portion of an intron of the JH (such as the JH to Cµ intron).

These targeting vectors can be introduced into mammalian cells by any suitable method including, but not limited, to transfection, transformation, virus-mediated transduction, or infection with a viral vector to target the ungulate heavy chain, kappa light chain or lambda light chain genes via homologous recombination. In one embodiment, the targeting vectors can contain a 3' recombination arm and a 5' recombination arm (i.e. flanking sequence) that is homologous to the genomic sequence of ungulate region of interest, and in particular, the heavy chain joining region. The 3' and 5' recombination arms can be designed such that they flank the 3' and 5' ends of at least one functional variable, joining, diversity, and/or constant region of the genomic sequence. The targeting of a functional region can render it inactive, which results in the inability of the cell to produce functional immunoglobulin molecules. In another embodiment, the homologous DNA sequence can include one or more intron and/or exon sequences. In addition to the nucleic acid sequences, the expression vector can contain selectable marker sequences, such as, for example, enhanced Green Fluorescent Protein (eGFP) gene sequences, initiation and/or enhancer sequences, poly A-tail sequences, and/or nucleic acid sequences that provide for the expression of the construct in prokaryotic and/or eukaryotic host cells. The selectable marker can be located between the 5' and 3' recombination arm sequence.

Modification of a targeted locus of a cell can be produced by introducing DNA into the cells, where the DNA has homology to the target locus and includes a marker gene, allowing for selection of cells comprising the integrated construct. The homologous DNA in the target vector will recombine with the chromosomal DNA at the target locus. The marker gene can be flanked on both sides by homologous DNA sequences, a 3' recombination arm and a 5' recombination arm. Methods for the construction of targeting vectors have been described in the art, see, for example, Dai et al., Nature Biotechnology 20: 251-255, 2002; WO 00/51424.

Various constructs can be prepared for homologous recombination at a target locus. The construct can include at least about 50 bp, 100 bp, 500 bp, 1 kbp, 2 kbp, 4 kbp, 5 kbp, 10 kbp, 15 kbp, 20 kbp, or 50 kbp of sequence homologous with the target locus. The sequence can include any contiguous sequence of an immunoglobulin gene.

Various considerations can be involved in determining the extent of homology of target DNA sequences, such as, for example, the size of the target locus, availability of sequences, relative efficiency of double cross-over events at the target locus and the similarity of the target sequence with other sequences. The targeting DNA can include a sequence in which DNA substantially isogenic flanks the desired sequence modifications with a corresponding target sequence in the genome to be modified. The substantially isogenic sequence can be at least about 95%, or at least about 97% or at least about 98% or at least about 99% or between 95 and 100%, 97-98%, 99.0-99.5%, 99.6-99.9%, or 100% identical to the corresponding target sequence (except for the desired sequence modifications). In a particular embodiment, the targeting DNA and the target DNA can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

In particular embodiments of the present invention, targeting vectors are provided to target the porcine heavy chain locus. In one particular embodiment, the targeting vector can contain 5' and 3' recombination arms that contain homologous sequence to the 3' and 5' flanking sequence of the J6 region of the porcine immunoglobulin heavy chain locus. Since the J6 region is the only functional joining region of the porcine immunoglobulin heavy chain locus, this will prevent the expression of a functional porcine heavy chain immunoglobulin. In a specific embodiment, the targeting vector can contain a 5' recombination arm that contains sequence homologous to genomic sequence 5' of the J6 region, optionally including J1-4 and a 3' recombination arm that contains sequence homologous to genomic sequence 3' of the J6 region, including the mu constant region (a "J6 targeting construct"). Further, this J6 targeting construct can also contain a selectable marker gene that is located between the 5' and 3' recombination arms. In another embodiments, the 5' targeting arm can contain sequence 5' of J1, J2 and/or J3. In a further embodiment, the 5' targeting arm can contain sequence 5' of the constant region. In another embodiment, the 3' targeting arm can contain sequence 3' of the constant region and/or including the constant region. In other embodiments, the targeting vector can contain a 5' recombination arm that contains sequence homologous to genomic sequence 5' of the diversity region, and a 3' recombination arm that contains sequence homologous to genomic sequence 3' of the diversity region of the porcine heavy chain locus. In a further embodiment, the targeting vector can contain a 5' recombination arm that contains sequence homologous to genomic sequence 5' of the mu constant region and a 3' recombination arm that contains sequence homologous to genomic sequence 3' of the mu constant region of the porcine heavy chain locus.

In other embodiments, targeting vectors designed to disrupt the expression of porcine heavy chain genes can contain recombination arms, for example, the 3' or 5' recombination arm, that target the constant region of heavy chain. In one embodiment, the recombination arm can target the mu constant region, for example, the C mu sequences described above or as disclosed in Sun & Butler Immunogenetics (1997) 46: 452-460. In another embodiment, the recombination arm can target the delta constant region, such as the sequence disclosed in Zhao et al. (2003) J immunol 171: 1312-1318, or the alpha constant region, such as the sequence disclosed in Brown & Butler (1994) Molec Immunol 31: 633-642.

Cells that have been transfected or otherwise received an appropriate targeting vector can then be selected or identified via genotype or phenotype analysis. In one embodiment, cells are transfected, grown in appropriately-selected medium to identify cells providing the appropriate integration. The presence of the selectable marker gene inserted into the immunoglobulin gene establishes the integration of the target construct into the host genome. Those cells which show the desired phenotype can then be further analyzed by restriction analysis, electrophoresis, Southern analysis, polymerase chain reaction, etc to analyze the DNA in order to establish whether homologous or non-homologous recombination occurred. This can be determined by employing probes for the insert and then sequencing the 5' and 3' regions flanking the insert for the presence of the immunoglobulin gene extending beyond the flanking regions of the construct or identifying the presence of a deletion, when such deletion is introduced. Primers can also be used which are complementary to a sequence within the construct and complementary to a sequence outside the construct and at the target locus. In this way, one can only obtain DNA duplexes having both of the primers present in the complementary chains if homologous recombination has occurred. By demonstrating the presence of the primer sequences or the expected size sequence, the occurrence of homologous recombination is supported.

The polymerase chain reaction used for screening homologous recombination events is known in the art, see, for example, Kim and Smithies, Nucleic Acids Res. 16:8887-8903, 1988; and Joyner et al., Nature 338:153-156, 1989. The specific combination of a mutant polyoma enhancer and a thymidine kinase promoter to drive the neomycin gene has been shown to be active in both embryonic stem cells and EC cells by Thomas and Capecchi, supra, 1987; Nicholas and Berg (1983) in Teratocarcinoma Stem Cell, eds. Siver, Martin and Strikland (Cold Spring Harbor Lab., Cold Spring Harbor, N.Y. (pp. 469-497); and Linney and Donerly, Cell 35:693-699, 1983.

Cells that have undergone homologous recombination can be identified by a number of methods. In one embodiment, the selection method can detect the depletion of the immunoglobulin gene directly, whether due to targeted knockout of the immunoglobulin gene by homologous recombination, or a mutation in the gene that results in a nonfunctioning or nonexpressed immunoglobulin. Selection via antibiotic resistance has been used most commonly for screening (see above). This method can detect the presence of the resistance gene on the targeting vector, but does not directly indicate whether integration was a targeted recombination event or a random integration. Alternatively, the marker can be a fluorescent marker gene such as GFP or RFP, or a gene that is detectable on the cell surface via cell sorting or FACs analysis. Certain technology, such as Poly A and promoter trap technology, increase the probability of targeted events, but again, do not give direct evidence that the desired phenotype, a cell deficient in immunoglobulin gene expression, has been achieved. In addition, negative forms of selection can be used to select for targeted integration; in these cases, the gene for a factor lethal to the cells (e.g. Tk or diptheria A toxin) is inserted in such a way that only targeted events allow the cell to avoid death. Cells selected by these methods can then be assayed for gene disruption, vector integration and, finally, immunoglobulin gene depletion. In these cases, since the selection is based on detection of targeting vector integration and not at the altered phenotype, only targeted knockouts, not point mutations, gene rearrangements or truncations or other such modifications can be detected.

Animal cells believed to lacking expression of functional immunoglobulin genes can be further characterized. Such characterization can be accomplished by the following techniques, including, but not limited to: PCR analysis, Southern blot analysis, Northern blot analysis, specific lectin binding assays, and/or sequencing analysis. Phenotypic characterization can also be accomplished, including testing for porcine IgG, IgM or IgA expression by binding of anti-mouse antibodies in various assays including immunofluroescence, immunocytochemistry, ELISA assays, flow cytometry, western blotting, testing for transcription of Ig in cells such as by RT-PCR.

PCR analysis as described in the art can be used to determine the integration of targeting vectors. In one embodiment, amplimers can originate in the antibiotic resistance gene and extend into a region outside the vector sequence. Southern analysis can also be used to characterize gross modifications in the locus, such as the integration of a targeting vector into the immunoglobulin locus. Whereas, Northern analysis can be used to characterize the transcript produced from each of the alleles. Further, sequencing analysis of the cDNA produced from the RNA transcript can also be used to determine the precise location of any mutations in the immunoglobulin allele.

Production of Genetically Modified Animals

Animals that contain the genetic modifications described herein can be produced by any method known to one skilled in the art, but are typically produced using cells such as those described above. Methods to produce animals with genetic modifications include, but are not limited to: nuclear transfer, intracytoplasmic sperm injection, modification of zygotes directly, (e.g., by pronuclear microinjection), blastocyst injection using embryonic stem cells, and sperm mediated gene transfer. In a typical embodiment, a method to produced such animals by nuclear transfer, for example, pigs, includes: enucleating an oocyte, fusing the oocyte with a donor nucleus from a cell in which at least one allele of at least one immunoglobulin gene has been inactivated, and implanting the nuclear transfer-derived embryo into a surrogate mother.

Alternatively, a method is provided for producing viable animals that lack any expression of functional immunoglobulin by inactivating both alleles of the immunoglobulin gene in embryonic stem cells, which can then be used to produce offspring. In another aspect, the present invention provides a method for producing viable animals, such as pigs, in which both alleles of the immunoglobulin gene have been rendered inactive. In one embodiment, the animals are produced by cloning using a donor nucleus from a cell in which both alleles of the immunoglobulin gene have been inactivated. In one embodiment, both alleles of the immunoglobulin gene are inactivated via a genetic targeting event.

Genetically altered animals that can be created by modifying zygotes directly. For mammals, the modified zygotes can be then introduced into the uterus of a pseudopregnant female capable of carrying the animal to term. For example, if whole animals lacking an immunoglobulin gene are desired, then embryonic stem cells derived from that animal can be targeted and later introduced into blastocysts for growing the modified cells into chimeric animals. For embryonic stem cells, either an embryonic stem cell line or freshly obtained stem cells can be used. In one embodiment of the invention, the totipotent cells are embryonic stem (ES) cells. The isolation of ES cells from blastocysts, the establishing of ES cell lines and their subsequent cultivation are carried out by conventional methods as described, for example, by Doetchmann et al., J. Embryol. Exp. Morph. 87:27-45 (1985); Li et al., Cell 69:915-926 (1992); Robertson, E. J. "Tetracarcinomas and Embryonic Stem Cells: A Practical Approach," ed. E. J. Robertson, IRL Press, Oxford, England (1987); Wurst and Joyner, "Gene Targeting: A Practical Approach," ed. A. L. Joyner, IRL Press, Oxford, England (1993); Hogen et al., "Manipulating the Mouse Embryo: A Laboratory Manual," eds. Hogan, Beddington, Costantini and Lacy, Cold Spring Harbor Laboratory Press, New York (1994); and Wang et al., Nature 336:741-744 (1992). In another suitable embodiment of the invention, the totipotent cells are embryonic germ (EG) cells. Embryonic Germ cells are undifferentiated cells functionally equivalent to ES cells, that is they can be cultured and transfected in vitro, then contribute to somatic and germ cell lineages of a chimera (Stewart et al., Dev. Biol. 161:626-628 (1994)). EG cells are derived by culture of primordial germ cells, the progenitors of the gametes, with a combination of growth factors: leukemia inhibitory factor, steel factor and basic fibroblast growth factor (Matsui et al., Cell 70:841-847 (1992); Resnick et al., Nature 359:550-551 (1992)). The cultivation of EG cells can be carried out using methods described in the article by Donovan et al., "Transgenic Animals, Generation and Use," Ed. L. M. Houdebine, Harwood Academic Publishers (1997), and in the original literature cited therein.

Tetraploid blastocysts for use in the invention may be obtained by natural zygote production and development, or by known methods by electrofusion of two-cell embryos and subsequently cultured as described, for example, by James et al., Genet. Res. Camb. 60:185-194 (1992); Nagy and Rossant, "Gene Targeting: A Practical Approach," ed. A. L. Joyner, IRL Press, Oxford, England (1993); or by Kubiak and Tarkowski, Exp. Cell Res. 157:561-566 (1985).

The introduction of the ES cells or EG cells into the blastocysts can be carried out by any method known in the art. A suitable method for the purposes of the present invention is the microinjection method as described by Wang et al., EMBO J. 10:2437-2450 (1991).

In other embodiments, sperm mediated gene transfer can be used to produce the genetically modified ungulates described herein. The methods and compositions described herein to either eliminate expression of endogenous immunoglobulin genes or insert xenogenous immunoglobulin genes can be used to genetically modify the sperm cells via any technique described herein or known in the art. The genetically modified sperm can then be used to impregnate a female recipient via artificial insemination, intracytoplasmic sperm injection or any other known technique. In one embodiment, the sperm and/or sperm head can be incubated with the exogenous nucleic acid for a sufficient time period. Sufficient time periods include, for example, about 30 seconds to about 5 minutes, typically about 45 seconds to about 3 minutes, more typically about 1 minute to about 2 minutes. In particular embodiments, the expression of xenogenous, such as human, immunoglobulin genes in ungulates as described herein, can be accomplished via intracytoplasmic sperm injection. The potential use of sperm cells as vectors for gene transfer was first suggested by Brackett et al., Proc., Natl. Acad. Sci. USA 68:353-357 (1971). This was followed by reports of the production of transgenic mice and pigs after in vitro fertilization of oocytes with sperm that had been incubated by naked DNA (see, for example, Lavitrano et al., Cell 57:717-723 (1989) and Gandolfi et al. Journal of Reproduction and Fertility Abstract Series 4, 10 (1989)), although other laboratories were not able to repeat these experiments (see, for example, Brinster et al. Cell 59:239-241 (1989) and Gavora et al., Canadian Journal of Animal Science 71:287-291 (1991)). Since then, there have been several reports of successful sperm mediated gene transfer in chicken (see, for example, Nakanishi and Iritani, Mol. Reprod. Dev. 36:258-261 (1993)); mice (see, for example, Maionc, Mol. Reprod. Dev. 59:406 (1998)); and pigs (see, for example, Lavitrano et al. Transplant. Proc. 29:3508-3509 (1997); Lavitrano et al., Proc. Natl. Acad. Sci. USA 99:14230-5 (2002); Lavitrano et al., Mol. Reprod. Dev. 64-284-91 (2003)). Similar techniques are also described in U.S. Pat. No. 6,376,743; issued Apr. 23, 2002; U.S. Patent Publication Nos. 20010044937, published Nov. 22, 2001, and 20020108132, published Aug. 8, 2002.

In other embodiments, intracytoplasmic sperm injection can be used to produce the genetically modified ungulates described herein. This can be accomplished by co-inserting an exogenous nucleic acid and a sperm into the cytoplasm of an unfertilized oocyte to form a transgenic fertilized oocyte, and allowing the transgenic fertilized oocyte to develop into a transgenic embryo and, if desired, into a live offspring. The sperm can be a membrane-disrupted sperm head or a demembranated sperm head. The co-insertion step can include the substep of preincubating the sperm with the exogenous nucleic acid for a sufficient time period, for example, about 30 seconds to about 5 minutes, typically about 45 seconds to about 3 minutes, more typically about 1 minute to about 2 minutes. The co-insertion of the sperm and exogenous nucleic acid into the oocyte can be via microinjection. The exogenous nucleic acid mixed with the sperm can contain more than one transgene, to produce an embryo that is transgenic for more than one transgene as described herein. The intracytoplasmic sperm injection can be accomplished by any technique known in the art, see, for example, U.S. Pat. No. 6,376,743. In particular embodiments, the expression of xenogenous, such as human, immunoglobulin genes in ungulates as described herein, can be accomplished via intracytoplasmic sperm injection.

Any additional technique known in the art, or a combination of various techniques known in the art, may be used to introduce transgenes into animals or cells. Such techniques include, but are not limited to pronuclear microinjection (see, for example, Hoppe, P. C. and Wagner, T. E., 1989, U.S. Pat. No. 4,873,191); retrovirus mediated gene transfer into germ lines (see, for example, Van der Putten et al., 1985, Proc. Natl. Acad. Sci., USA 82:6148-6152); gene targeting in embryonic stem cells (see, for example, Thompson et al., 1989, Cell 56:313-321; Wheeler, M. B., 1994, WO 94/26884); electroporation of embryos (see, for example, Lo, 1983, Mol Cell. Biol. 3:1803-1814); cell gun; transfection; transduction; retroviral infection; adenoviral infection; lentivirus infection; adenoviral-associated infection; liposome-mediated gene transfer; naked DNA transfer; and sperm-mediated gene transfer (see, for example, Lavitrano et al., 1989, Cell 57:717-723); etc. For a review of such techniques, see, for example, Gordon, 1989, Transgenic Animals, Intl. Rev. Cytol. 115:171-229. In particular embodiments, the expression of xenogenous, such as human, immunoglobulin genes in ungulates as described herein, can be accomplished via these techniques or a combination thereof.

In a specific aspect of the present invention, ungulate, such as porcine or bovine, cells lacking one allele, optionally both alleles of an ungulate heavy chain, kappa light chain and/or lambda light chain gene can be used as donor cells for nuclear transfer into recipient cells to produce cloned, transgenic animals. Alternatively, ungulate heavy chain, kappa light chain and/or lambda light chain gene knockouts can be created in embryonic stem cells, which are then used to produce offspring.

The present invention provides a method for cloning an animal, such as a pig, lacking a functional immunoglobulin gene via somatic cell nuclear transfer. Such animals can be bred with other genetically modified animals, and/or gametes or cells from these animals can be used to further modify or genetically engineer the Ig locus. For example, heterozygous genetically modified animals can be bred together to produce homozygous genetically modified animals, or heterozygous genetically modified cells can be further modified to produce cells with a homozygous genetic modification. The cells can subsequently used in SCNT to produce a homozygous genetically modified animal. In general, the animal can be produced by a nuclear transfer process comprising the following steps: obtaining desired differentiated cells to be used as a source of donor nuclei; obtaining oocytes from the animal; enucleating said oocytes; transferring the desired differentiated cell or cell nucleus into the enucleated oocyte, e.g., by fusion or injection, to form NT units; activating the resultant NT unit; and transferring said cultured NT unit to a host animal such that the NT unit develops into a fetus. Nuclear transfer techniques or nuclear transplantation techniques are known in the art (Dai et al. Nature Biotechnology 20:251-255; Polejaeva et al Nature 407:86-90 (2000); Campbell et al, Theriogenology, 43:181 (1995) Campbell, et al., *Theriogenology* 68 Suppl 1: S214-31 (2007); Vajta, et al., *Reprod Fertil Dev* 19(2): 403-23 (2007), Collas et al, Mol. Report Dev., 38:264-267 (1994); Keefer et al, Biol. Reprod., 50:935-939 (1994); Sims et al, Proc. Natl. Acad. Sci., USA, 90:6143-6147 (1993); WO 94/26884; WO 94/24274, and WO 90/03432, U.S. Pat. Nos. 4,944,384 and 5,057,420), Vatja G, Trends Biotechnol. June; 25(6):250-3 (2007)). A donor cell nucleus, which has been modified to alter the immunoglobulin gene, is transferred to a recipient oocyte. The use of this method is not restricted to a particular donor cell type. The donor cell can be as described herein, see also, for example, Wilmut et al Nature 385 810 (1997); Campbell et al Nature 380 64-66 (1996); Dai et al., Nature Biotechnology 20:251-255, 2002 or Cibelli et al Science 280 1256-1258 (1998). All cells of normal karyotype, including embryonic, fetal and adult somatic cells which can be used successfully in nuclear transfer can be employed. Fetal fibroblasts are a particularly useful class of donor cells. Generally suitable methods of nuclear transfer are described in Campbell et al Theriogenology 43 181 (1995), Campbell, et al., *Theriogenology* 68 Suppl 1: S214-31 (2007); Vajta, et al., *Reprod Fertil Dev* 19(2): 403-23 (2007), Dai et al. Nature Biotechnology 20:251-255, Polejaeva et al Nature 407:86-90 (2000), Collas et al Mol. Reprod. Dev. 38 264-267 (1994), Keefer et al Biol. Reprod. 50 935-939 (1994), Sims et al Proc. Nat'l. Acad. Sci. USA 90 6143-6147 (1993), WO-A-9426884, WO-A-9424274, WO-A-9807841, WO-A-9003432, U.S. Pat. No. 4,994,384 and U.S. Pat. No. 5,057,420. Differentiated or at least partially differentiated donor cells can also be used. Donor cells can also be, but do not have to be, in culture and can be quiescent. Nuclear donor cells which are quiescent are cells which can be induced to enter quiescence or exist in a quiescent state in vivo. Prior art methods have also used embryonic cell types in cloning procedures (Campbell et al (Nature, 380:64-68, 1996) and Stice et al (Biol. Reprod., 20 54:100-110, 1996). Somatic nuclear donor cells may be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus, or adult animal. In a suitable embodiment of the invention, nuclear donor cells are selected from the group consisting of epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, extended cells, cumulus cells, epidermal cells or endothelial cells. In another embodiment, the nuclear donor cell is an embryonic stem cell. In a particular embodiment, fibroblast cells can be used as donor cells. In another embodiment of the invention, the nuclear donor cells of the invention are germ cells of an animal. Any germ cell of an animal species in the embryonic, fetal, or adult stage may be used as a nuclear donor cell. In a suitable embodiment, the nuclear donor cell is an embryonic germ cell.

Nuclear donor cells may be arrested in any phase of the cell cycle (G0, G1, G2, S, M) so as to ensure coordination with the acceptor cell. Any method known in the art may be used to manipulate the cell cycle phase. Methods to control the cell cycle phase include, but are not limited to, G0 quiescence induced by contact inhibition of cultured cells, G0 quiescence induced by removal of serum or other essential nutrient, G0 quiescence induced by senescence, G0 quiescence induced by addition of a specific growth factor; G0 or G1 quiescence induced by physical or chemical means such as heat shock, hyperbaric pressure or other treatment with a chemical, hormone, growth factor or other substance; S-phase control via treatment with a chemical agent which interferes with any point of the replication procedure; M-phase control via selection using fluorescence activated cell sorting, mitotic shake off, treatment with microtubule disrupting agents or any chemical which disrupts progression in mitosis (see also Freshney, R. I., "Culture of Animal Cells: A Manual of Basic Technique," Alan R. Liss, Inc, New York (1983).

Methods for isolation of oocytes are well known in the art. Essentially, this can comprise isolating oocytes from the ovaries or reproductive tract of an animal. A readily available source of oocytes is slaughterhouse materials. For the combination of techniques such as genetic engineering, nuclear transfer and cloning, oocytes must generally be matured in vitro before these cells can be used as recipient cells for nuclear transfer, and before they can be fertilized by the sperm cell to develop into an embryo. This process generally requires collecting immature (prophase I) oocytes from mammalian ovaries, e.g., bovine or porcine ovaries obtained at a slaughterhouse, and maturing the oocytes in a maturation medium prior to fertilization or enucleation until the oocyte attains the metaphase II stage, which in the case of bovine oocytes generally occurs about 18-24 hours post-aspiration, and in the case of porcine oocytes generally occurs between 30-48 hours post-aspiration. This period of time is known as the "maturation period". In certain embodiments, the oocyte is obtained from a gilt. A "gilt" is a female pig that has never had offspring. In other embodiments, the oocyte is obtained from a sow. A "sow" is a female pig that has previously produced offspring. A metaphase II stage oocyte can be the recipient oocyte, at this stage it is believed that the oocyte can be or is sufficiently "activated" to treat the introduced nucleus as it does a fertilizing sperm. Metaphase II stage oocytes, which have been matured in vivo have been successfully used in nuclear transfer techniques. Essentially, mature metaphase II oocytes can be collected surgically from either non-superovulated or superovulated animal 35 to 48, or 39-41, hours past the onset of estrus or past the injection of human chorionic gonadotropin (hCG) or similar hormone. The oocyte can be placed in an appropriate medium, such as a hyaluronidase solution.

After a fixed time maturation period, which ranges from about 30 to 60 hours, or from about 35 to 55 hours or from about 40 to 55 hours or about 40 about 45, about 50, about 55 hours, the oocytes can be enucleated. Prior to enucleation the oocytes can be removed and placed in appropriate medium, such as HECM containing 1 milligram per milliliter of hyaluronidase prior to removal of cumulus cells. The stripped oocytes can then be screened for polar bodies, and the selected metaphase II oocytes, as determined by the presence of polar bodies, are then used for nuclear transfer. Enucleation follows.

Enucleation can be performed by known methods, such as described in U.S. Pat. No. 4,994,384. For example, metaphase II oocytes can be placed in either HECM, optionally containing 7.5 micrograms per milliliter cytochalasin B, for immediate enucleation, or can be placed in a suitable medium, for example an embryo culture medium such as CR1aa, plus 10% estrus cow serum, and then enucleated later, such as not more than 24 hours later, or not more than 16-18 hours later. Enucleation can be accomplished microsurgically using a micropipette to remove the polar body and the adjacent cytoplasm. The oocytes can then be screened to identify those of which have been successfully enucleated. One way to screen the oocytes is to stain the oocytes with 1 microgram per milliliter 33342 Hoechst dye in HECM, and then view the oocytes under ultraviolet irradiation for less than 10 seconds. The oocytes that have been successfully enucleated can then be placed in a suitable culture medium, for example, CR1aa plus 10% serum, or hepes buffered TCM199 or NCSU23.

A single mammalian cell of the same species as the enucleated oocyte can then be transferred into the perivitelline space of the enucleated oocyte used to produce the NT unit. The mammalian cell and the enucleated oocyte can be used to produce NT units according to methods known in the art. For example, the cells can be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels can open between the two cells. Due to the thermodynamic instability of such a small opening, it enlarges until the two cells become one. See, for example, U.S. Pat. No. 4,997,384 by Prather et al. A variety of electrofusion media can be used including, for example, sucrose, mannitol, sorbitol and phosphate buffered solution. Fusion can also be accomplished using Sendai virus as a fusogenic agent (Graham, Wister Inot. Symp. Monogr., 9, 19, 1969). Also, the nucleus can be injected directly into the oocyte rather than using electroporation fusion. See, for example, Collas and Barnes, Mol. Reprod. Dev., 38:264-267 (1994). After fusion, the resultant fused NT units are then placed in a suitable medium until activation, for example, CR1aa medium, hepes buffered TCM199, or NCSU23. In some embodiments, activation can be effected shortly thereafter, for example less than 24 hours later, or about 4-9 hours later, or optimally 1-2 hours after fusion. In a particular embodiment, activation occurs at least one hour post fusion and at 40-41 hours post maturation.

The NT unit can be activated by known methods. Such methods include, for example, culturing the NT unit at sub-physiological temperature, in essence by applying a cold, or actually cool temperature shock to the NT unit. This can be most conveniently done by culturing the NT unit at room temperature, which is cold relative to the physiological temperature conditions to which embryos are normally exposed. Alternatively, activation can be achieved by application of known activation agents. For example, penetration of oocytes by sperm during fertilization has been shown to activate prefusion oocytes to yield greater numbers of viable pregnancies and multiple genetically identical calves after nuclear transfer. Also, treatments such as electrical and chemical shock can be used to activate NT embryos after fusion. See, for example, U.S. Pat. No. 5,496,720, to Susko-Parrish et al. Fusion and activation can be induced by application of an AC pulse of 5 V for 5 s followed by two DC pulses of 1.5 kV/cm for 60 .mu.s each using an ECM2001 Electrocell Manipulator (BTX Inc., San Diego, Calif.). Additionally, activation can be effected by simultaneously or sequentially by increasing levels of divalent cations in the oocyte, and reducing phosphorylation of cellular proteins in the oocyte. This can generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators. Phosphorylation can be reduced by known methods, for example, by the addition of kinase inhibitors, e.g., serine-threonine kinase inhibitors, such as 6-dimethyl-aminopurine, staurosporine, 2-aminopurine, and sphingosine. Alternatively, phosphorylation of cellular proteins can be inhibited by introduction of a phosphatase into the oocyte, e.g., phosphatase 2A and phosphatase 2B.

The activated NT units, or "fused embryos", can then be cultured in a suitable in vitro culture medium until the generation of cell colonies. Culture media suitable for culturing and maturation of embryos are well known in the art. Examples of known media, which can be used for embryo culture and maintenance, include Ham's F-10+10% fetal calf serum (FCS), Tissue Culture Medium-199 (TCM-199)+ 10% fetal calf serum, Tyrodes-Albumin-Lactate-Pyruvate (TALP), Dulbecco's Phosphate Buffered Saline (PBS), Eagle's and Whitten's media, and, in one specific example, the activated NT units can be cultured in NCSU-23 medium for about 1-4 h at approximately 38.6.degree. C. in a humidified atmosphere of 5% CO2. Afterward, the cultured NT unit or units can be washed and then placed in a suitable media contained in well plates which can contain a suitable confluent feeder layer. Suitable feeder layers include, by way of example, fibroblasts and epithelial cells. The NT units are cultured on the feeder layer until the NT units reach a size suitable for transferring to a recipient female, or for obtaining cells which can be used to produce cell colonies. These NT units can be cultured until at least about 2 to 400 cells, about 4 to 128 cells, or at least about 50 cells. In a preferred embodiment, the NT units are transferred directly to a recipient female, without any further in vitro culture.

Activated NT units can then be transferred (embryo transfers), 0-144 hours post activation, to the oviduct of an female pigs. In one embodiment, the female pigs can be an estrus-synchronized recipient gilt. Crossbred gilts (large white/Duroc/Landrace) (280-400 lbs) can be used. The gilts can be synchronized as recipient animals by oral administration of 18-20 mg Regu-Mate (Altrenogest, Hoechst, Warren, N.J.) mixed into the feed. Regu-Mate can be fed for 14 consecutive days. One thousand units of Human Chorionic Gonadotropin (hCG, Intervet America, Millsboro, Del.) can then be administered i.m. about 105 h after the last Regu-Mate treatment. Embryo transfers can then be performed about 22-26 h after the hCG injection. To improve embryo transfer outcomes, various strategies, for example, administration of hormones to the recipient, or co-transfer of parthenogenic embryos, can be employed (see King, T. J., et al.). *Reproduction* 123(4): 507-15 (2002). In one embodiment, the pregnancy can be brought to term and result in the birth of live offspring. In another embodiment, the pregnancy can be terminated early and embryonic or fetal cells can be harvested.

The animals can also be further manipulated. For example, the animals can be bred with animals of the same or different genotype, and the resulting animals are deficient in B cells. The animals can also be used to derive nuclear donors for additional nuclear transfer. In certain embodiments, the animals are used to develop cells that can be further genetically manipulated and then be used as nuclear donors. In certain embodiments, these are somatic cells such as fibroblast.

Additional Genetic Modifications

Animals or cells lacking expression of functional immunoglobulin produced according to the process, sequences and/or constructs described herein, can contain additional genetic modifications to eliminate the expression of xenoantigens. Such animals can further be modified to eliminate the expression of at least one allele of the alpha-1,3-galactosyltransferase gene, the CMP-Neu5Ac hydroxylase gene (see, for example, U.S. Patent Publication. 2005-0223418), the iGb3 synthase gene (see, for example, U.S. Patent Publication 2005-0155095), and/or the Forssman synthase gene (see, for example, U.S. Patent Publication 2006-0068479). In additional embodiments, the animals discloses herein can also contain genetic modifications to express fucosyltransferase and/or sialyltransferase, complement pathway inhibitor genes (CD55, CD59, CD46), genes expressing T-cell modulating effects such as CTLA4-Ig, or a dominant negative inhibitor of class II MHC (CIITA), or other genes that modulate the expression of B-cell or T cell mediated immune function. In further embodiments, such animals can be further modified to eliminate the expression of genes which effect immune function. For example, genes which have been inactivated in mice to produce an immuno compromised phenotype, can be cloned and disrupted by gene targeting in pigs. Some genes which have been targeted in mice and may be targeted to produce immuno compromised pigs include beta 2-microglobulin (MHC class I deficiency, Koller et al., Science, 248:1227-1230), TCR Alpha, TCR Beta (Mombaerts et al., Nature, 360:225-231), RAG-1 and RAG-2 (Mombaerts et al., (1992) Cell 68, 869-877, Shinkai, et al., (1992) Cell 68, 855-867, U.S. Pat. No. 5,859,307). To achieve these additional genetic modifications, in one embodiment, cells can be modified to contain multiple genetic modifications. In other embodiments, animals can be bred together to achieve multiple genetic modifications. In one specific embodiment, animals, such as pigs, lacking expression of functional immunoglobulin, produced according to the process, sequences and/or constructs described herein, can be bred with animals, such as pigs, lacking expression of α-1,3-galactosyltransferase (for example, as described in WO 04/028243).

In certain embodiments, animals or cells lacking expression of functional immunoglobulin can contain additional genetic modifications. In one embodiment, the additional genetic modification eliminates the expression of a gene (null − phenotype) In another embodiment, the additional genetic modification (null + phenotype).

In another embodiment, the present invention provides a method for producing viable pigs that lack any expression of functional alpha-1,3-GT by breeding a male pig heterozygous for the alpha-1,3-GT gene with a female pig heterozygous for the alpha-1,3-GT gene. In one embodiment, the pigs are heterozygous due to the genetic modification of one allele of the alpha-1,3-GT gene to prevent expression of that allele. In another embodiment, the pigs are heterozygous due to the presence of a point mutation in one allele of the alpha-1,3-GT gene. In another embodiment, the point mutation can be a T-to-G point mutation at the second base of exon 9 of the alpha-1,3-GT gene. In one specific embodiment, a method to produce a porcine animal that lacks any expression of functional alpha-1,3-GT is provided wherein a male pig that contains a T-to-G point mutation at the second base of exon 9 of the alpha-1,3-GT gene is bred with a female pig that contains a T-to-G point mutation at the second base of exon 9 of the alpha-1,3-GT gene, or vise versa.

Genetic modifications can include more than just homologous targeting, but can also include random integrations of exogenous genes, mutations, deletions and insertions of genes of any kind. The additional genetic modifications can be made by further genetically modifying cells obtained from the transgenic cells and animals described herein or, in certain cases, by breeding the animals described herein with animals that have been further genetically modified.

Non-limiting examples of additional genetic modifications according to the present invention include modifications to eliminate the expression of at least one allele of the alpha-1,3-galactosyltransferase gene, the CMP-Neu5Ac hydroxylase gene (see, for example, U.S. Pat. No. 7,368, 284), the iGb3 synthase gene (see, for example, U.S. Patent Publication No. 2005/0155095), and/or the Forssman synthase gene (see, for example, U.S. Patent Publication No. 2006/0068479). In another embodiment, the expression of additional genes responsible for xenograft rejection can be eliminated or reduced. Such genes include, but are not limited to the CMP-NEUAc Hydroxylase Gene, the isoGloboside 3 Synthase gene, and the Forssman synthase gene. In addition, genes or cDNA encoding complement related proteins, which are responsible for the suppression of complement mediated lysis can also be expressed in the animals and tissues of the present invention. Such genes include, but are not limited to CD59, DAF, MCP and CD46 (see, for example, WO 99/53042; Chen et al. Xenotransplantation, Volume 6 Issue 3 Page 194-August 1999, which describes pigs that express CD59/DAF transgenes; Costa C et al, *Xenotransplantation*. 2002 January; 9(1):45-57, which describes transgenic pigs that express human CD59 and H-transferase; Zhao L et al.; Diamond L E et al. *Transplantation*. 2001 Jan. 15; 71(1):132-42, which describes a human CD46 transgenic pigs.

Non-limiting examples of additional genetic modifications according to the present invention include modifications to express fucosyltransferase, sialyltransferase and/or any member of the family of glucosyltransferases.

Additional modifications can include expression of compounds, such as antibodies, which down-regulate the expression of a cell adhesion molecule by the cells, such as described in WO 00/31126, entitled "Suppression of xenograft rejection by down regulation of a cell adhesion molecules" and compounds in which costimulation by signal 2 is prevented, such as by administration to the organ recipient of a soluble form of CTLA-4 from the xenogeneic donor organism, for example as described in WO 99/57266, entitled "Immunosuppression by blocking T cell costimulation signal 2 (B7/CD28 interaction)". T-cell activation requires at least two sets of signaling events. The first is initiated by the specific recognition through the T-cell receptor of an antigenic peptide combined with major histocompatibility complex (MHC) molecules on antigen presenting cells (APCs). The second set of signals is antigen nonspecific and is delivered by T-cell costimulatory receptors interacting with their ligands on APCs. In the absence of costimulation, T-cell activation is impaired or aborted, which may result in an antigen specific unresponsive state of clonal anergy, or in deletion by apoptotic death. Of several T-cell costimulatory pathways, the most prominent is the CD28 pathway. CD28, a cell surface molecule expressed on T-cells, and its counter receptors, the B7.1 (CD80) and B7.2(CD86) molecules, present on dendritic cells, macrophages, and B-cells, have been characterized and identified as attractive targets for interrupting T-cell costimulatory signals.

Cytotoxic T lymphocyte-associated antigen 4 (CTLA4), a T cell surface antigen that is upregulated following CD28/B7 interaction, shares affinity for the B7 ligands with CD28, and can actually bind CD80 and CD86 with greater affinity and avidity than does CD28. CTLA4 successfully competes with CD28 in binding B7 on APCs and, in so doing, downregulates the T cell response. This co-stimulatory blockade by CTLA4 offers a strategy for downregulation of the CD4+T cell response. Human CTLA4-Ig (hCTLA4-Ig) has been shown to successfully inhibit CD4+T cell proliferation by blocking costimulatory CD28/B7 activation of allo CD4+T cells in vitro and in vivo in mice (Engelhardt et al., J Immunology, 177:1052-1061, 2006) and non-human primates (Levisetti, et al., J Immunology, 159:5187-5191, 1997).

In one embodiment, the animals or cells lacking expression of functional immunoglobulin, produced according to the present invention, can be further modified to transgenically express a cytoxic T-lymphocyte associated protein 4-immunoglobin (CTLA4), or these animals lacking functional Ig can be bred to animals which transgenically express CTLA4. The animals or cells can be modified to express CTLA4 peptide or a biologically active fragment (e.g., extracellular domain, truncated form of the peptide in which at least the transmembrane domain has been removed) or derivative thereof. The peptide may be, e.g., human or porcine. The CTLA4 peptide can be mutated. Mutated peptides may have higher affinity than wildtype for porcine and/or human B7 molecules. In one specific embodiment, the mutated CTLA4 can be CTLA4 (Glu104, Tyr29). The CTLA4 peptide can be modified such that it is expressed intracellularly. Other modifications of the CTLA4 peptide include addition of a endoplasmic reticulum retention signal to the N or C terminus. The endoplasmic reticulum retention signal may be, e.g., the sequence KDEL. The CTLA4 peptide can be fused to a peptide dimerization domain or an immunoglobulin (Ig) molecule. The CTLA4 fusion peptides can include a linker sequence that can join the two peptides. In another embodiment, animals lacking expression of functional immunoglobulin, produced according to the present invention, can be administered a CTLA4 peptide (pCTLA4-Ig, or hCTLA4-Ig (Orencia) as a drug to suppress their T-cell response.

To achieve these additional genetic modifications, in one embodiment, cells can be modified to contain multiple genetic modifications. In other embodiments, animals can be bred together to achieve multiple genetic modifications. In one specific embodiment, animals, such as pigs, lacking expression of functional immunoglobulin, produced according to the process, sequences and/or constructs described herein, can be bred with animals, such as pigs, lacking expression of alpha-1,3-galactosyl transferase (for example, as described in WO 04/028243).

Xenogenous Immunoglobulin Expression

One aspect of the present invention provides animals and cells that lack native immunoglobulin expression and are further modified to express at least part of a xenogenous, and in particular a human, antibody (i.e. immunoglobulin (Ig)) locus. This human locus can undergo rearrangement and express a diverse population of human antibody molecules in the ungulate. These cloned, transgenic ungulates provide a replenishable, theoretically infinite supply of human antibodies (such as polyclonal antibodies), which can be used for therapeutic, diagnostic, purification, and other clinically relevant purposes.

In one particular embodiment, artificial chromosome (ACs) can be used to accomplish the transfer of human immunoglobulin genes into ungulate cells and animals. ACs permit targeted integration of megabase size DNA fragments that contain single or multiple genes. The ACs, therefore, can introduce heterologous DNA into selected cells for production of the gene product encoded by the heterologous DNA. In a one embodiment, one or more ACs with integrated human immunoglobulin DNA can be used as a vector for introduction of human Ig genes into ungulates (such as pigs). First constructed in yeast in 1983, ACs are man-made linear DNA molecules constructed from essential cis-acting DNA sequence elements that are responsible for the proper replication and partitioning of natural chromosomes (Murray et al. (1983), Nature 301:189-193). A chromosome requires at least three elements to function. Specifically, the elements of an artificial chromosome include at least: (1) autonomous replication sequences (ARS) (having properties of replication origins—which are the sites for initiation of DNA replication), (2) centromeres (site of kinetochore assembly that is responsible for proper distribution of replicated chromosomes at mitosis and meiosis), and (3) telomeres (specialized structures at the ends of linear chromosomes that function to both stabilize the ends and facilitate the complete replication of the extreme termini of the DNA molecule).

In one embodiment, the human Ig can be maintained as an independent unit (an episome) apart from the ungulate chromosomal DNA. For example, episomal vectors contain the necessary DNA sequence elements required for DNA replication and maintenance of the vector within the cell. Episomal vectors are available commercially (see, for example, Maniatis, T. et al., Molecular Cloning, A Laboratory Manual (1982) pp. 368-369). The AC can stably replicate and segregate along side endogenous chromosomes. In an alternative embodiment, the human IgG DNA sequences can be integrated into the ungulate cell's chromosomes thereby permitting the new information to be replicated and partitioned to the cell's progeny as a part of the natural chromosomes (see, for example, Wigler et al. (1977), Cell 11:223). The AC can be translocated to, or inserted into, the endogenous chromosome of the ungulate cell. Two or more ACs can be introduced to the host cell simultaneously or sequentially.

ACs, furthermore, can provide an extra-genomic locus for targeted integration of megabase size DNA fragments that contain single or multiple genes, including multiple copies of a single gene operatively linked to one promoter or each copy or several copies linked to separate promoters. ACs can permit the targeted integration of megabase size DNA fragments that contain single or multiple human immunoglobulin genes. The ACs can be generated by culturing the cells with dicentric chromosomes (i.e., chromosomes with two centromeres) under such conditions known to one skilled in the art whereby the chromosome breaks to form a minichromosome and formerly dicentric chromosome.

ACs can be constructed from humans (human artificial chromosomes: "HACs"), yeast (yeast artificial chromosomes: "YACs"), bacteria (bacterial artificial chromosomes: "BACs"), bacteriophage P1-derived artificial chromosomes: "PACs") and other mammals (mammalian artificial chromosomes: "MACs"). The ACs derive their name (e.g., YAC, BAC, PAC, MAC, HAC) based on the origin of the centromere. A YAC, for example, can derive its centromere from *S. cerevisiae*. MACs, on the other hand, include an active mammalian centromere while HACs refer to chromosomes that include human centromeres. Furthermore, plant artificial chromosomes ("PLACs") and insect artificial chromosomes can also be constructed. The ACs can include elements derived from chromosomes that are responsible for both replication and maintenance. ACs, therefore, are capable of stably maintaining large genomic DNA fragments such as human Ig DNA.

In one embodiment, ungulates containing YACs are provided. YACs are genetically engineered circular chromosomes that contain elements from yeast chromosomes, such as *S. cerevisiae*, and segments of foreign DNAs that can be much larger than those accepted by conventional cloning vectors (e.g., plasmids, cosmids). YACs allow the propagation of very large segments of exogenous DNA (Schlessinger, D. (1990), Trends in Genetics 6:248-253) into mammalian cells and animals (Choi et al. (1993), Nature Gen 4:117-123). YAC transgenic approaches are very powerful and are greatly enhanced by the ability to efficiently manipulate the cloned DNA. A major technical advantage of yeast is the ease with which specific genome modifications can be made via DNA-mediated transformation and homologous recombination (Ramsay, M. (1994), Mol Biotech 1:181-201). In one embodiment, one or more YACs with integrated human Ig DNA can be used as a vector for introduction of human Ig genes into ungulates (such as pigs).

The YAC vectors contain specific structural components for replication in yeast, including: a centromere, telomeres, autonomous replication sequence (ARS), yeast selectable markers (e.g., TRP1, URA3, and SUP4), and a cloning site for insertion of large segments of greater than 50 kb of exogenous DNA. The marker genes can allow selection of the cells carrying the YAC and serve as sites for the synthesis of specific restriction endonucleases. For example, the TRP1 and URA3 genes can be used as dual selectable markers to ensure that only complete artificial chromosomes are maintained. Yeast selectable markers can be carried on both sides of the centromere, and two sequences that seed telomere formation in vivo are separated. Only a fraction of one percent of a yeast cell's total DNA is necessary for replication, however, including the center of the chromosome (the centromere, which serves as the site of attachment between sister chromatids and the sites of spindle fiber attachment during mitosis), the ends of the chromosome (telomeres, which serve as necessary sequences to maintain the ends of eukaryotic chromosomes), and another short stretch of DNA called the ARS which serves as DNA segments where the double helix can unwind and begin to copy itself. In one embodiment, YACs can be used to clone up to about 1, 2, or 3 Mb of immunoglobulin DNA. In another embodiment, at least 25, 30, 40, 50, 60, 70, 75, 80, 85, 90, or 95 kilobases.

Yeast integrating plasmids, replicating vectors (which are fragments of YACs), can also be used to express human Ig. The yeast integrating plasmid can contain bacterial plasmid sequences that provide a replication origin and a drug-resistance gene for growth in bacteria (e.g., *E. coli*), a yeast marker gene for selection of transformants in yeast, and restriction sites for inserting Ig sequences. Host cells can stably acquire this plasmid by integrating it directly into a chromosome. Yeast replicating vectors can also be used to express human Ig as free plasmid circles in yeast. Yeast or ARS-containing vectors can be stabilized by the addition of a centromere sequence. YACs have both centromeric and telomeric regions, and can be used for cloning very large pieces of DNA because the recombinant is maintained essentially as a yeast chromosome. YACs are provided, for example, as disclosed in U.S. Pat. Nos. 6,692,954, 6,495,318, 6,391,642, 6,287,853, 6,221,588, 6,166,288, 6,096,878, 6,015,708, 5,981,175, 5,939,255, 5,843,671, 5,783,385, 5,776,745, 5,578,461, and 4,889,806; European Patent Nos. 1 356 062 and 0 648 265; PCT Publication Nos. WO 03/025222, WO 02/057437, WO 02/101044, WO 02/057437, WO 98/36082, WO 98/12335, WO 98/01573, WO 96/01276, WO 95/14769, WO 95/05847, WO 94/23049, and WO 94/00569.

In another embodiment, ungulates containing BACs are provided. BACs are F-based plasmids found in bacteria, such as *E. Coli*, that can transfer approximately 300 kb of foreign DNA into a host cell. Once the Ig DNA has been cloned into the host cell, the newly inserted segment can be replicated along with the rest of the plasmid. As a result, billions of copies of the foreign DNA can be made in a very short time. In a particular embodiment, one or more BACs with integrated human Ig DNA are used as a vector for introduction of human Ig genes into ungulates (such as pigs).

The BAC cloning system is based on the *E. coli* F-factor, whose replication is strictly controlled and thus ensures stable maintenance of large constructs (Willets, N., and R. Skurray (1987), Structure and function of the F-factor and mechanism of conjugation. In *Escherichia coli and Salmonella Typhimurium*: Cellular and Molecular Biology (F. C. Neidhardt, Ed) Vol. 2 pp 1110-1133, Am. Soc. Microbiol., Washington, D.C.). BACs have been widely used for cloning of DNA from various eukaryotic species (Cai et al. (1995), Genomics 29:413-425; Kim et al. (1996), Genomics 34:213-218; Misumi et al. (1997), Genomics 40:147-150; Woo et al. (1994), Nucleic Acids Res 22:4922-4931; Zimmer, R. and Gibbins, A. M. V. (1997), Genomics 42:217-226). The low occurrence of the F-plasmid can reduce the potential for recombination between DNA fragments and can avoid the lethal overexpression of cloned bacterial genes. BACs can stably maintain the human immunoglobulin genes in a single copy vector in the host cells, even after 100 or more generations of serial growth. BAC (or pBAC) vectors can accommodate inserts in the range of approximately 30 to 300 kb pairs. One specific type of BAC vector, pBeloBac11, uses a complementation of the lacZ gene to distinguish insert-containing recombinant molecules from colonies carrying the BAC vector, by color. When a DNA fragment is cloned into the lacZ gene of pBeloBac11, insertional activation results in a white colony on X-Gal/IPTG plates after transformation (Kim et al. (1996), Genomics 34:213-218) to easily identify positive clones. For example, BACs can be provided such as disclosed in U.S. Pat. Nos. 6,713,281, 6,703,198, 6,649,347, 6,638,722, 6,586,184, 6,573,090, 6,548,256, 6,534,262, 6,492,577, 6,492,506, 6,485,912, 6,472,177, 6,455,254, 6,383,756, 6,277,621, 6,183,957, 6,156,574, 6,127,171, 5,874,259, 5,707,811, and 5,597,694; European Patent Nos. 0 805 851; PCT Publication Nos. WO 03/087330, WO 02/00916, WO 01/39797, WO 01/04302, WO 00/79001, WO 99/54487, WO 99/27118, and WO 96/21725.

In another embodiment, ungulates containing bacteriophage PACs are provided. In a particular embodiment, one or more bacteriophage PACs with integrated human Ig DNA are used as a vector for introduction of human Ig genes into ungulates (such as pigs). For example, PACs can be provided such as disclosed in U.S. Pat. Nos. 6,743,906, 6,730,500, 6,689,606, 6,673,909, 6,642,207, 6,632,934, 6,573,090, 6,544,768, 6,489,458, 6,485,912, 6,469,144, 6,462,176, 6,413,776, 6,399,312, 6,340,595, 6,287,854, 6,284,882, 6,277,621, 6,271,008, 6,187,533, 6,156,574, 6,153,740, 6,143,949, 6,017,755, and 5,973,133; European Patent Nos. 0 814 156; PCT Publication Nos. WO 03/091426, WO 03/076573, WO 03/020898, WO 02/101022, WO 02/070696, WO 02/061073, WO 02/31202, WO 01/44486, WO 01/07478, WO 01/05962, and WO 99/63103.

In a further embodiment, ungulates containing MACs are provided. MACs possess high mitotic stability, consistent and regulated gene expression, high cloning capacity, and non-immunogenicity. Mammalian chromosomes can be comprised of a continuous linear strand of DNA ranging in size from approximately 50 to 250 Mb. The DNA construct can further contain one or more sequences necessary for the DNA construct to multiply in yeast cells. The DNA construct can also contain a sequence encoding a selectable marker gene. The DNA construct can be capable of being maintained as a chromosome in a transformed cell with the DNA construct. MACs provide extra-genomic specific integration sites for introduction of genes encoding proteins of interest and permit megabase size DNA integration so that, for example, genes encoding an entire metabolic pathway, a very large gene [e.g., such as the cystic fibrosis (CF) gene (~600 kb)], or several genes [e.g., a series of antigens for preparation of a multivalent vaccine] can be stably introduced into a cell.

Methods using the MACs to construct artificial chromosomes from other species, such as insect and fish species are also provided. The artificial chromosomes are fully functional stable chromosomes. Two types of artificial chromosomes are provided. One type, herein referred to as SATACs [satellite artificial chromosomes] are stable heterochromatic chromosomes, and the another type are minichromosomes based on amplification of euchromatin. As used herein, a formerly dicentric chromosome is a chromosome that is produced when a dicentric chromosome fragments and acquires new telomeres so that two chromosomes, each having one of the centromeres, are produced. Each of the fragments can be replicable chromosomes.

In one embodiment, artificial chromosomes can be generated by culturing the cells with the dicentric chromosomes under conditions whereby the chromosome breaks to form a minichromosome and formerly dicentric chromosome. In one embodiment, the SATACs can be generated from the minichromosome fragment, see, for example, in U.S. Pat. No. 5,288,625. In another embodiment, the SATACs can be generated from the fragment of the formerly dicentric chromosome. The SATACs can be made up of repeating units of short satellite DNA and can be fully heterochromatic. In one embodiment, absent insertion of heterologous or foreign DNA, the SATACs do not contain genetic information. In other embodiments, SATACs of various sizes are provided that are formed by repeated culturing under selective conditions and subcloning of cells that contain chromosomes produced from the formerly dicentric chromosomes. These chromosomes can be based on repeating units 7.5 to 10 Mb in size, or megareplicons. These megareplicons can be tandem blocks of satellite DNA flanked by heterologous non-satellite DNA. Amplification can produce a tandem array of identical chromosome segments [each called an amplicon] that contain two inverted megareplicons bordered by heterologous ["foreign"] DNA. Repeated cell fusion, growth on selective medium and/or BrdU [5-bromodeoxyuridine] treatment or other genome destabilizing reagent or agent, such as ionizing radiation, including X-rays, and subcloning can result in cell lines that carry stable heterochromatic or partially heterochromatic chromosomes, including a 150-200 Mb "sausage" chromosome, a 500-1000 Mb gigachromosome, a stable 250-400 Mb megachromosome and various smaller stable chromosomes derived therefrom. These chromosomes are based on these repeating units and can include human immunoglobulin DNA that is expressed. (See also U.S. Pat. No. 6,743,967

In other embodiments, MACs can be provided, for example, as disclosed in U.S. Pat. Nos. 6,743,967, 6,682,729, 6,569,643, 6,558,902, 6,548,287, 6,410,722, 6,348,353, 6,297,029, 6,265,211, 6,207,648, 6,150,170, 6,150,160, 6,133,503, 6,077,697, 6,025,155, 5,997,881, 5,985,846, 5,981,225, 5,877,159, 5,851,760, and 5,721,118; PCT Publication Nos. WO 04/066945, WO 04/044129, WO 04/035729, WO 04/033668, WO 04/027075, WO 04/016791, WO 04/009788, WO 04/007750, WO 03/083054, WO 03/068910, WO 03/068909, WO 03/064613, WO 03/052050, WO 03/027315, WO 03/023029, WO 03/012126, WO 03/006610, WO 03/000921, WO 02/103032, WO 02/097059, WO 02/096923, WO 02/095003, WO 02/092615, WO 02/081710, WO 02/059330, WO 02/059296, WO 00/18941, WO 97/16533, and WO 96/40965.

In another aspect of the present invention, ungulates and ungulate cells containing HACs are provided. In a particular embodiment, one or more HACs with integrated human Ig DNA are used as a vector for introduction of human Ig genes into ungulates (such as pigs). In a particular embodiment, one or more HACs with integrated human Ig DNA are used to generate ungulates (for example, pigs) by nuclear transfer which express human Igs in response to immunization and which undergo affinity maturation. Various approaches may be used to produce ungulates that express human antibodies ("human Ig"). These approaches include, for example, the insertion of a HAC containing both heavy and light chain Ig genes into an ungulate or the insertion of human B-cells or B-cell precursors into an ungulate during its fetal stage or after it is born (e.g., an immune deficient or immune suppressed ungulate) (see, for example, WO 01/35735, filed Nov. 17, 2000, US 02/08645, filed Mar. 20, 2002). In either case, both human antibody producing cells and ungulate antibody-producing B-cells may be present in the ungulate. In an ungulate containing a HAC, a single B-cell may produce an antibody that contains a combination of ungulate and human heavy and light chain proteins. In still other embodiments, the total size of the HAC is at least to approximately 1, 2, 3, 4, 5, 6, 7, 8, 9 or 10 Mb. For example, HACs can be provided such as disclosed in U.S. Pat. Nos. 6,642,207, 6,590,089, 6,566,066, 6,524,799, 6,500,642, 6,485,910, 6,475,752, 6,458,561, 6,455,026, 6,448,041, 6,410,722, 6,358,523, 6,277,621, 6,265,211, 6,146,827, 6,143,566, 6,077,697, 6,025,155, 6,020,142, and 5,972,649; U.S. Pat. Application No. 2003/0037347; PCT Publication Nos. WO 04/050704, WO 04/044156, WO 04/031385, WO 04/016791, WO 03/101396, WO 03/097812, WO 03/093469, WO 03/091426, WO 03/057923, WO 03/057849, WO 03/027638, WO 03/020898, WO 02/092812, and WO 98/27200.

Additional examples of ACs into which human immunoglobulin sequences can be inserted for use in the invention include, for example, BACs (e.g., pBeloBAC11 or pBAC108L; see, e.g., Shizuya et al. (1992), Proc Natl Acad Sci USA 89(18):8794-8797; Wang et al. (1997), Biotechniques 23(6):992-994), bacteriophage PACs, YACs (see, e.g., Burke (1990), Genet Anal Tech Appl 7(5):94-99), and MACs (see, e.g., Vos (1997), Nat. Biotechnol. 15(12):1257-1259; Ascenzioni et al. (1997), Cancer Lett 118(2):135-142), such as HACs, see also, U.S. Pat. Nos. 6,743,967, 6,716,608, 6,692,954, 6,670,154, 6,642,207, 6,638,722, 6,573,090, 6,492,506, 6,348,353, 6,287,853, 6,277,621, 6,183,957, 6,156,953, 6,133,503, 6,090,584, 6,077,697, 6,025,155, 6,015,708, 5,981,175, 5,874,259, 5,721,118, and 5,270,201; European Patent Nos. 1 437 400, 1 234 024, 1 356 062, 0 959 134, 1 056 878, 0 986 648, 0 648 265, and 0 338 266; PCT Publication Nos. WO 04/013299, WO 01/07478, WO 00/06715, WO 99/43842, WO 99/27118, WO 98/55637, WO 94/00569, and WO 89/09219. Additional examples include those AC provided in, for example, PCT Publication No. WO 02/076508, WO 03/093469, WO 02/097059; WO 02/096923; US Publication Nos US 2003/0113917 and US 2003/003435; and U.S. Pat. No. 6,025,155.

In other embodiments of the present invention, ACs transmitted through male gametogenesis in each generation. The AC can be integrating or non-integrating. In one embodiment, the AC can be transmitted through mitosis in substantially all dividing cells. In another embodiment, the AC can provide for position independent expression of a human immunogloulin nucleic acid sequence. In a particular embodiment, the AC can have a transmittal efficiency of at least 10% through each male and female gametogenesis. In one particular embodiment, the AC can be circular. In another particular embodiment, the non-integrating AC can be that deposited with the Belgian Coordinated Collections of Microorganisms—BCCM on Mar. 27, 2000 under accession number LMBP 5473 CB. In additional embodiments, methods for producing an AC are provided wherein a mitotically stable unit containing an exogenous nucleic acid transmitted through male gametogenesis is identified; and an entry site in the mitotically stable unit allows for the integration of human immunoglobulin genes into the unit.

In other embodiments, ACs are provided that include: a functional centromere, a selectable marker and/or a unique cloning site. In other embodiments, the AC can exhibit one or more of the following properties: it can segregate stably as an independent chromosome, immunoglobulin sequences can be inserted in a controlled way and can expressed from the AC, it can be efficiently transmitted through the male and female germline and/or the transgenic animals can bear the chromosome in greater than about 30, 40, 50, 60, 70, 80 or 90% of its cells.

In particular embodiments, the AC can be isolated from fibroblasts (such as any mammalian or human fibroblast) in which it was mitotically stable. After transfer of the AC into hamster cells, a lox (such as loxP) site and a selectable marker site can be inserted. In other embodiments, the AC can maintain mitotic stability, for example, showing a loss of less than about 5, 2, 1, 0.5 or 0.25 percent per mitosis in the absence of selection. See also, US 2003/0064509 and WO 01/77357.

In another aspect of the present invention, transgenic ungulates are provided that expresses a xenogenous immunoglobulin loci or fragment thereof. In certain embodiments, the xenogenous immunoglobulin can be expressed from an immunoglobulin locus that is integrated within an endogenous ungulate chromosome. In other embodiments, the xenogenous immunoglobulin is not integrated with an endogenous chromosome. In one embodiment, ungulate cells derived from the transgenic animals are provided. In one embodiment, the xenogenous immunoglobulin locus can be inherited by offspring. In another embodiment, the xenogenous immunoglobulin locus can be inherited through the male germ line by offspring. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B-cells to produce xenogenous immunoglobulin in response to exposure to one or more antigens.

Human immunoglobulin genes, such as the Ig heavy chain gene (human chromosome 14), Ig kappa chain gene (human chromosome #2) and/or the Ig lambda chain gene (chromosome #22) can be inserted into ACs, as described above. In a particular embodiment, any portion of the human heavy, kappa and/or lambda Ig genes can be inserted into ACs. In one embodiment, the nucleic acid can be at least 70, 80, 90, 95, or 99% identical to the corresponding region of a naturally-occurring nucleic acid from a human. In other embodiments, more than one class of human antibody is produced by the ungulate. In various embodiments, more than one different human Ig or antibody is produced by the ungulate. In one embodiment, an AC containing both a human Ig heavy chain gene and Ig light chain gene, such as an automatic human artificial chromosome ("AHAC," a circular recombinant nucleic acid molecule that is converted to a linear human chromosome in vivo by an endogenously expressed restriction endonuclease) can be introduced. In one embodiment, the human heavy chain loci and the light chain loci are on different chromosome arms (i.e., on different side of the centromere). In one embodiments, the heavy chain can include the mu heavy chain, and the light chain can be a lambda or kappa light chain. The Ig genes can be introduced simultaneously or sequentially in one or more than one ACs.

In particular embodiments, the ungulate or ungulate cell expresses one or more nucleic acids encoding all or part of a human Ig gene which undergoes rearrangement and expresses more than one human Ig molecule, such as a human antibody protein. Thus, the nucleic acid encoding the human Ig chain or antibody is in its unrearranged form (that is, the nucleic acid has not undergone V(D)J recombination). In particular embodiments, all of the nucleic acid segments encoding a V gene segment of an antibody light chain can be separated from all of the nucleic acid segments encoding a J gene segment by one or more nucleotides. In a particular embodiment, all of the nucleic acid segments encoding a V gene segment of an antibody heavy chain can be separated from all of the nucleic acid segments encoding a D gene segment by one or more nucleotides, and/or all of the nucleic acid segments encoding a D gene segment of an antibody heavy chain are separated from all of the nucleic acid segments encoding a J gene segment by one or more nucleotides. Administration of an antigen to a transgenic ungulate containing an unrearranged human Ig gene is followed by the rearrangement of the nucleic acid segments in the human Ig gene locus and the production of human antibodies reactive with the antigen.

In one embodiment, the AC can express a portion or fragment of a human chromosome that contains an immunoglobulin gene. In one embodiment, the AC can express at least 300 or 1300 kb of the human light chain locus, such as described in Davies et al. 1993 Biotechnology 11:911-914.

The human immunoglobulin genes can be first inserted into ACs and then the human-immunoglobulin-containing ACs can be inserted into the ungulate cells. Alternatively, the ACs can be transferred to an intermediary mammalian cell, such as a CHO cell, prior to insertion into the ungulate call. In one embodiment, the intermediary mammalian cell can also contain and AC and the first AC can be inserted into the AC of the mammalian cell. In particular, a YAC containing human immunoglobulin genes or fragments thereof in a yeast cell can be transferred to a mammalian cell that harbors an MAC. The YAC can be inserted into the MAC. The MAC can then be transferred to an ungulate cell. The human Ig genes can be inserted into ACs by homologous recombination. The resulting AC containing human Ig genes, can then be introduced into ungulate cells. One or more ungulate cells can be selected by techniques described herein or those known in the art, which contain an AC containing a human Ig.

In particular embodiments of the present invention, the transfer of ACs containing human immunoglobulin genes to porcine cells, such as those described herein or known in the art, can be accomplished via site specific recombinase mediated transfer. In one particular embodiment, the ACs can be transferred into porcine fibroblast cells. In another particular embodiment, the ACs can be YACs. In other embodiments of the present invention, the circularized DNA, such as an AC, that contain the site specific recombinase target site can be transferred into a cell line that has a site specific recombinase target site within its genome. In one embodiment, the cell's site specific recombinase target site can be located within an exogenous chromosome. The exogenous chromosome can be an artificial chromosome that does not integrate into the host's endogenous genome. In one embodiment, the AC can be transferred via germ line transmission to offspring. In one particular embodiment, a YAC containing a human immunoglobulin gene or fragment thereof can be circularized via a site specific recombinase and then transferred into a host cell that contains a MAC, wherein the MAC contains a site specific recombinase site. This MAC that now contains human immunoglobulin loci or fragments thereof can then be fused with a porcine cell, such as, but not limited to, a fibroblast. The porcine cell can then be used for nuclear transfer.

In other embodiments, methods to circularize at least 100 kb of DNA are provided wherein the DNA can then be integrated into a host genome via a site specific recombinase. In one embodiment, at least 100, 200, 300, 400, 500, 1000, 2000, 5000, 10,000 kb of DNA can be circularized. In another embodiment, at least 1000, 2000, 5000, 10,000, or 20,000 megabases of DNA can be circularized. In one embodiment, the circularization of the DNA can be accomplished by attaching site specific recombinase target sites at each end of the DNA sequence and then applying the site specific recombinase to result in circularization of the DNA. In one embodiment, the site specific recombinase target site can be lox. In another embodiment, the site specific recombinase target site can be Flt. In certain embodiments, the DNA can be an artificial chromosome, such as a YAC or any AC described herein or known in the art. In another embodiment, the AC can contain human immunoglobulin loci or fragments thereof.

Site-specific recombinases include enzymes or recombinases that recognize and bind to a short nucleic acid site or sequence-specific recombinase target site, i.e., a recombinase recognition site, and catalyze the recombination of nucleic acid in relation to these sites. These enzymes include recombinases, transposases and integrases. Examples of sequence-specific recombinase target sites include, but are not limited to, lox sites, att sites, dif sites and frt sites. Non-limiting examples of site-specific recombinases include, but are not limited to, bacteriophage P1 Cre recombinase, yeast FLP recombinase, Inti integrase, bacteriophage lamda, phi 80, P22, P2, 186, and P4 recombinase, Tn3 resolvase, the Hin recombinase, and the Cin recombinase, *E. coli* xerC and xerD recombinases, *Bacillus thuringiensis* recombinase, TpnI and the β-lactamase transposons, and the immunoglobulin recombinases. In one embodiment, the recombination site can be a lox site that is recognized by the Cre recombinase of bacteriophage P1. Lox sites refer to a nucleotide sequence at which the product of the cre gene of bacteriophage P1, the Cre recombinase, can catalyze a site-specific recombination event. A variety of lox sites are known in the art, including the naturally occurring loxP, loxB, loxL and loxR, as well as a number of mutant, or variant, lox sites, such as loxP511, loxP514, loxdelta86, loxdelta117, loxC2, loxP2, loxP3 and lox P23. Additional example of lox sites include, but are not limited to, loxB, loxL, loxR, loxP, loxP3, loxP23, lo-delta-86, lox-delta-117, loxP511, and loxC2. In another embodiment, the recombination site is a recombination site that is recognized by a recombinases other than Cre. In one embodiment, the recombinase site can be the FRT sites recognized by FLP recombinase of the 2 pi plasmid of *Saccharomyces cerevisiae*. FRT sites refer to a nucleotide sequence at which the product of the FLP gene of the yeast 2 micron plasmid, FLP recombinase, can catalyze site-specific recombination. Additional examples of the non-Cre recombinases include, but are not limited to, site-specific recombinases include: att sites recognized by the Int recombinase of bacteriophage lambda (e.g. att1, att2, att3, attP, attB, attL, and attR), the recombination sites recognized by the resolvase family, and the recombination site recognized by transposase of *Bacillus thruingiensis*.

EXAMPLES

Example 1: Construction and Design of Hc KO Vector

A portion of the genomic porcine Ig Hc locus was cloned and characterized. FIG. 1 illustrates the architecture of the porcine Hc locus. The single functional JH was found to reside within 6 kb upstream of the coding sequence for the Mu constant (Cμ region). The porcine JH was identified as an 'Achilles heel' that could be deleted to produce only non-functional VDJ rearrangement and, thus, prevent B-cell survival.

A poly (A) trap targeting vector was constructed (pPL708, FIG. 1) by flanking a CMV enhancer-pgk-neoR cassette that lacked polyA signal sequences, with a 2 kb upstream arm and a 5.8 kb downstream arm of homology. The downstream arm retained the complete JH to Cμ intron, and a few by of 3' JH sequence, to insure normal splicing between the neoR transcript and the poly(A) signals found downstream of the Cμ coding region.

Vector Construction.

Hc sequence data required for construction of a porcine Hc gene-targeting vector was generated using a bacterial artificial chromosome (BAC) carrying a major portion of the porcine Ig Hc (J. E. Butler, J. Sun and P. Chardon, unpublished). Subsequent steps involved amplification of relevant porcine Hc sequences from a PPFF cell line using primer sequences based on BAC sequence analysis (see FIG. 1). The PPFF cell line used to generate the targeting vector was the same as that used for SCNT. Long range PCR was used to generate a 9.2 kb amplimer that included the JH region along with flanking sequences of porcine Ig Hc. It was done so that both homologous arms of the targeting vector could be generated from a contiguous fragment. A 2.0 kb amplimer served as the 5' arm of the knockout vector, with a Sal1 site at the 5' end introduced by PCR. It's comprised of sequences within the intron between the DH and JH regions as well as the 4 pseudo JH's located upstream of the functional JH. This fragment was cloned into the TOPO XL plasmid (Invitrogen, Carlsbad, Calif.). A 5.9 kb amplimer served as the 3' homologous arm of the knockout vector. It's comprised of the 3'end of the functional JH (the fifth JH) coding region and extends just beyond the poly A signal of the C ?1 coding region. This fragment was then cloned into TOPO XL. The pKOTKneo vector (Lexicon Genetics, The Woodlands, Tex.) from which the poly A signal had been excised was used to generate the pPL708 targeting construct. A Xba1/BamH1 fragment containing the 5.8 kb 3' homologous arm sequence was ligated into the Xba1/BglII digested pKOTKneo vector, downstream of the PGK promoter-neomycin resistance (pgk-neoR) gene cassette. A Sal1/BamH1 fragment containing the 2.0 kb 5' homologous arm sequence was ligated into this same vector digested with Sal1/BamH1, upstream of the PGK-neoR gene cassette. A 0.4 kb CMV enhancer sequence was inserted into the BamH1 site of this vector, between the 5' homologous arm and the PGK-neoR cassette, making a CMV-PGK-neoR cassette to complete the pPL708 Hc targeting vector. PCR reagents were obtained from Takara, Japan and restriction enzymes from NEB, Ipswich, Mass.

Example 2: Heterozygous Hc KO in Porcine Cells

Isolation and Transfection of Primary Porcine Fetal Fibroblasts.

PCFF4-1 to PCFF4-10 PPFF cells were isolated from 10 fetuses of the same pregnancy at day 33 of gestation. After removing the head and viscera, fetuses were washed with Hanks' Balanced Salt Solution (HBSS, Invitrogen), placed in 20 ml of HBSS and diced with small surgical scissors. The tissue pellet was resuspended in 50 ml tubes with 40 ml of DMEM+100 U/ml collagenase (Invitrogen) per fetus. Tubes were incubated for 40 min in a shaking water bath at 37° C. The digested tissue was allowed to settle for 3-4 min and the cell-rich supernatant was transferred to a new 50 ml tube and spun down. The cells were then resuspended in 40 ml of DMEM, 10% Fetal Calf Serum, lx non-essential amino acids, 1 mM sodium pyruvate (Invitrogen) and 2 ng/ml basic fibroblast growth factor (Roche Molecular Biochemicals, Indianapolis, Ind.), then seeded into 10 cm dishes. All cells were cryopreserved upon reaching confluence. A male fetus (PCFF4-3) and two female fetuses (PCFF4-6, PCFF4-8) were used for transfection. Linearized vector DNA pPL708 (0.5-10 µg) was introduced into 0.5-2 million cells by electroporation using a ECM2001 Electrocell Manipulator (BTX Inc., San Diego, Calif.). Forty-eight hours post transfection, the transfected cells were seeded into 48-well plates at a density of 2,000 cells per well and were selected with 250 ng/ml of G418 (Invitrogen, Carlsbad, Calif.). Cells from confluent wells were harvested from plates and split into two for PCR screening and cryopreservation for SCNT.

Transfections were performed to produce G418 resistant colonies, which were then screened for presence of the targeting event. Three colonies were determined to harbor the desired targeting event by PCR and Southern blot (screening strategy as depicted in FIG. 2).

PCR Screening of Resistant Fibroblast Clones.

PPFF cells were lysed with of 40 mM Tris pH8.9, 0.9% Triton X100, 0.9% Nonidet P40, 400 ug/ml Proteinase K Invitrogen or Sigma, St. Louis, Mo.) at 60 C for 30 minutes. Forward and reverse primers used to detect 5' targeting were: HCKOXba5'2: tctagaagacgctggagagaggccag; 5'armS: taaagcgcatgctccagactgcctt, respectively. PCR conditions were 65° C. 15 minutes and 95° C. 10 minutes then a cocktail was added to all samples containing water, primers, Takara 10x buffer, dNTPs, and Taq. PCR conditions continued as 94° C. 2 minutes, (94° C. 30 seconds, 66° C. 30 seconds, 72° C. 5 minutes (35 cycles)), 68° C. 7 minutes. Forward and reverse primers used to detect 3' targeting were: Neo442S: catcgccttctatcgccttctt; 650+ca: aagtacttgccgc-ctctcagga, respectively. PCR conditions were similar except denaturation was for 10 seconds, annealing temperature was 65 C, and extension was at 68° C. for 10 minutes all for 30 cycles. Primers were made by Sigma.

Example 3: Somatic Cell Nuclear Transfer to Produce Heterozygous Hc KO Pigs

Somatic Cell Nuclear Transfer (SCNT) Procedure.

Cells from one of the three correctly targeted colonies obtained from transfection of pPL708 into female cell line PCFF4-8 were used as nuclear donors for SCNT. SCNT procedures were performed on in vitro matured oocytes (BoMed, Madison, Wis. and/or TransOVA, IA) using techniques described in the literature (Polejaeva, et al., (2000) Nature 407, 86-90, Dai et al., (2002) Nature biotechnology 20, 251-255, Campbell et al., (2007) Theriogenology 68 Suppl 1, S214-231, Vatja et al., (2007) Reprod Fertil Dev 19, 403-423). Electrical fusion and activation of reconstructed oocytes was performed using an ECM2001 Electrocell Manipulator (BTX Inc., San Diego). Fused nuclear transfer embryos were cultured in NCSU-23 medium for 1-4 h at 38.5° C., and then transferred to the oviduct of an estrus-synchronized recipient gilt. Crossbred gilts (large white/Duroc/Landrace) (280-400 lbs) were synchronized as recipient animals by oral administration of 18-20 mg Regu-Mate (Altrenogest, Hoechst, Warren, N.J.) mixed into their feed. Regu-Mate was fed for 14 consecutive days. Human Chorionic Gonadotropin (hCG, 1000 units; Intervet America, Millsboro, Del.) was administered intramuscularly 105 h after the last Regu-Mate treatment. Embryo transfers were done 22-26 h after the hCG injection. Pregnant Mare Serum Gonadotropin (PMSG, 1000 IU) and hCG (500 IU) we used on day 10 and 13 post transfer for maintenance of pregnancy. Pregnancy was confirmed via ultrasonography 28 days post-transfer. Pregnancies were monitored thereafter on a weekly basis. All piglets were born via natural parturition.

A total of 682 oocytes were reconstructed and transferred to 3 recipient gilts. All 3 gilts were pregnant post-embryo transfer. One recipient was euthanized to collect day 45 fetuses, and primary fetal fibroblasts were isolated for further analysis, future re-cloning, and/or additional genetic modification. The remaining two recipients carried their pregnancies to term and produced nine female piglets. Five of the nine piglets were confirmed to be Hc +/− by Southern blot (data not shown). All Hc +/− piglets were healthy, reached puberty and were used for breeding, and subsequent production of mature male Hc+/− pigs. Additional Hc +/− pigs were produced using cells from a second Hc targeted colony in SCNT, and also by re-cloning using cells derived from fetus 708C4:1-4 (collection detailed above) in SCNT.

Figure 2B:
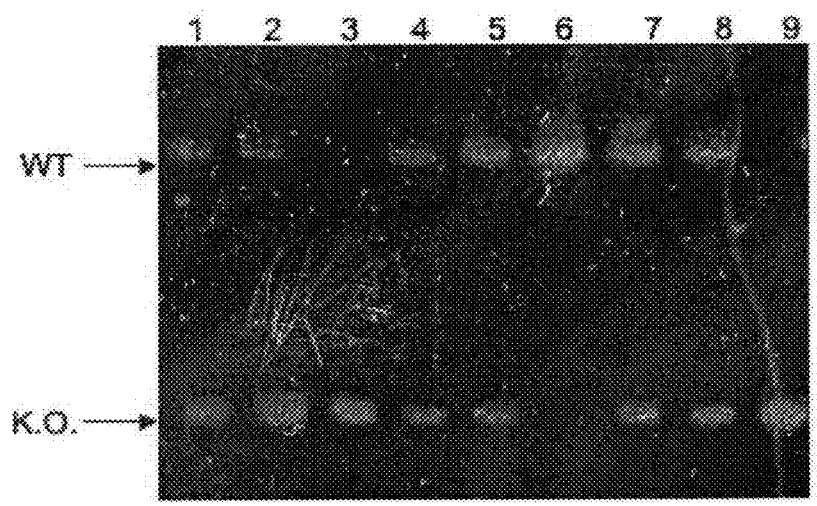
FIG. 2B shows an image of a southern blot analysis of DNA digested with XbaI, a non-targeted allele shows a band at 22 kb, as described in FIG. 2A. A targeted allele shows a band at 3.3 kb. The lane numbers correspond to the piglet numbers and their genotypes shown in Table 1.

Example 4: Breeding of Heterozygous Hc KO Pigs to Produce Homozygous Hc KO Neonatal Piglets As discussed, the only functional JH within the Hc locus was deleted by gene targeting, and should effectively prevent proper VDJ rearrangement of the Hc locus. To confirm the hypothesis that the absence of productive VDJ rearrangement is predicted to abolish Ig expression, B-cell survival and follicular development in Hc −/− pigs, phenotypical characterization was performed on the first litter of 9 piglets, obtained from a Hc +/− cross Hc +/− breeding, on the day of farrowing, before any suckling by the piglets was allowed, in order to prevent any Ig cross-contamination from sow to neonatal piglet. Such a mating should generate one of 4 different genotypes, which under classical Mendelian genetics are expected to follow the 1 Hc +/+ WT: 2 Hc +/− heterozygotes: 1 Hc −/− homozygote ratio. Genotyping was performed by Southern blot analysis as shown in FIG. 2B and listed in Table 1.

TABLE 1

Ig levels in the sera of littermates of various genotypes.

| | | Conc. [µg/ml]$^a$ | | |
| --- | --- | --- | --- | --- |
| Piglet # | Hc | IgM | IgG | IgA |
| 1 | +/− | 1.88 + 0.08 | 9.04 + 0.9 | 1.57 + 0.15 |
| 2 | +/− | 1.91 + 0.04 | 15.28 + 1.1 | 2.25 + 0.18 |
| 3 | −/− | ND | ND | ND |
| 4 | +/− | 1.01 + 0.06 | 5.61 + 0.2 | 2.78 + 0.21 |
| 5 | +/− | 1.48 + 0.1 | 7.48 + 0.3 | 1.27 + 0.19 |
| 6 | +/+ | 1.28 + 0.15 | 18.42 + 1.2 | 2.58 + 0.37 |

TABLE 1-continued

Ig levels in the sera of littermates of various genotypes.

| | | Conc. [µg/ml][a] | | |
|---|---|---|---|---|
| Piglet # | Hc | IgM | IgG | IgA |
| 7 | +/− | NA | NA | NA |
| 8 | +/− | 3.84 + 0.13 | 9.47 + 0.5 | 2.91 + 0.39 |
| 9 | −/− | ND | ND | ND |

[a]ND = below the detection limit of 0.4-0.6 ng/ml;
NA = serum not available for testing;
+ = Standard Error of the Mean.

FIG. 2B shows Southern blot results from this litter following Hc +/− cross Hc +/− breeding. Among 9 piglets, piglet 6 was Hc +/+ (wild-type, WT), piglets 1, 2, 4, 5, 7, and 8 were Hc +/−, and piglets 3 and 9 were Hc −/−. The percentage of Hc −/− piglets obtained from this litter (22.2%) is close to what would be expected under Mendelian genetics (25%). Phenotypic characterization of this litter is detailed in example 6.

Example 5: Genotyping of Homozygous Hc KO Piglets

Southern Blot Analysis of Pigs.

Pig tissues were lysed overnight at 60° C. in a shaking incubator in lysis solution (50 mM Tris, pH 8.0, 0.15M NaCl, 10 mM EDTA, 1% SDS, 25% sodium perchlorate, 1% 2-mercaptoethanol and 200 ug/ml proteinase K (20 mg/ml)). DNA was extracted with phenol/chloroform and precipitated with isopropyl alcohol. Resolubilized DNA was treated with RNase A (1 mg/ml) and RNase T1 (1,000 U/ul) at 37 C for 1 h, then with Proteinase K (20 mg/ml) at 55 C for 1 h, followed by extraction with phenol/chloroform and then precipitated with ethanol and resuspended in TE buffer. 20 ug of DNA was digested with NcoI or Xba I. Digested DNA was precipitated with ethanol, resuspended in TE, and separated on a 0.8% agarose gel. After electrophoresis the DNA was transferred to a nylon membrane using standard procedures and probed with a digoxigenin labeled Hc Cµ probe for the NcoI digest:

GGCTGAAGTCTGAGGCCTGGCAGATGAGCTTGGACGTGCGCTGGGGAGTA

CTGGAGAAGGACTCCCGGGTGGGGACGAAGATGTTCAAGACGGGGGGCT

GCTCCTCTACGACTGCAGGCAGGAACGGGGCGTCACTGTGCCGGCGGCAC

CCGGCCCCGCCCCCGCCACAGCCACAGGGGGAGCCCAGCTCACCTGGCCC

AGAGATGGACACGGACTTGGTGCCACTGGGGTGCTGGACCTCGCACACCA

GGAAGGCCTCTGGGTCCTGGGGGATGCTCACAGAGGGTAGGAGCACCCG

GGAGGAGGCCAAGT;

or probed with a digoxigenin labeled JH probe for the XbaI digest:

CTCTGCACTCACTACCGCCGGACGCGCACTGCCGTGCTGCCCATGGACCA

CGCTGGGGAGGGGTGAGCGGACAGCACGTTAGGAAGTGTGTGTGTGCGC

GTGGGTGCAAGTCGAGCCAAGGCCAAGATCCAGGGGCTGGGCCCTGTGCC

CAGAGGAGAATGGCAGGTGGAGTGTAGCTGGATTGAAAGGTGGCCTGAA

GGGTGGGGCATCCTGTTTGGAGGCTCACTCTCAGCCCCAGGGTCTCTGGTT

CCTGCCGGGTGGGGGCGCAAGGTGCCTACCACACCCTGCTAGCCCCTC

GTCCAGTCCCGGGCCTGCCTCTTCACCACGGAAGAGGATAAGCCAGGCTG

CAGGCTTCATGTGCGCCGTGGAGAACCCAGTTCGGCCCTTGGAGG.

Bands were detected using a chemiluminescent substrate system (Roche Molecular Biochemicals, Indianapolis, Ind.).

FIG. 2B shows the XbaI digested and probed Southern blot performed on litter 150-4 following Hc +/−×Hc +/− breeding. Hc +/+ (wild-type, WT, number 6), Hc +/− (heterozygous, numbers 1, 2, 4, 5, 7, and 8), and Hc −/− (homozygous, numbers 3 and 9) piglets were born.

Example 6: Phenotypic Characterization of Homozygous Hc KO Pigs

Handling of Piglets Phenotypically Characterized.

Litters from interbred Hc +/− pigs were genotyped by Southern blot (see FIG. 2B and Table 1). For all experiments, litter 150-4 containing wild-type (WT), Hc +/−, and Hc −/− piglets were not allowed to suckle to prevent Ig cross-contamination from sow colostrum and were sampled for phenotypic analysis on the day of farrowing. Other litters produced from interbreeding of Hc +/− pigs were reared using standard procedures and were subsequently weaned at approximately 4 weeks of age. Some of these Hc −/− pigs were also tested at 8 weeks of age in some assays. Necropsy was also performed on some piglets post-weaning that were euthanized, based on veterinarian recommendations, for health considerations, in order to determine cause of death and gross and histological findings. Animals were handled in accordance with reviewed and approved IACUC protocols.

Flow Cytometry.

Piglets were bled by venous puncture and collected in 20 U/ml of heparin (Baxter, Deerfield, Ill.). Platelets were washed away and red blood cells were lysed with BD Pharm Lyse (BD biosciences, San Jose, Calif.) using standard procedures. One million white blood cells (WBCs) were stained per tube. For single staining, primary Abs included mouse anti-porcine IgM (M160; mouse IgG1, a kind gift from K. Nielsen, ADRI, Canada), and a mouse IgG1 isotype control (MOPC-31C, BD Biosciences). The secondary Ab was goat anti-mouse IgG1 conjugated to RPE (Jackson ImmunoResearch, West Grove, Pa.). Primary Abs were incubated for 45 min at 4° C. and secondary Abs for 30 min at 4° C. Samples were washed with BSA staining buffer (BD biosciences) between Ab incubations. Samples were analyzed on the FACSaria flow cytometer using BD FACSdiva software (BD). The lymphocyte gate was determined by scatter plot using standard protocol. At least 10,000 lymphocytes were counted per run.

Figure 3:
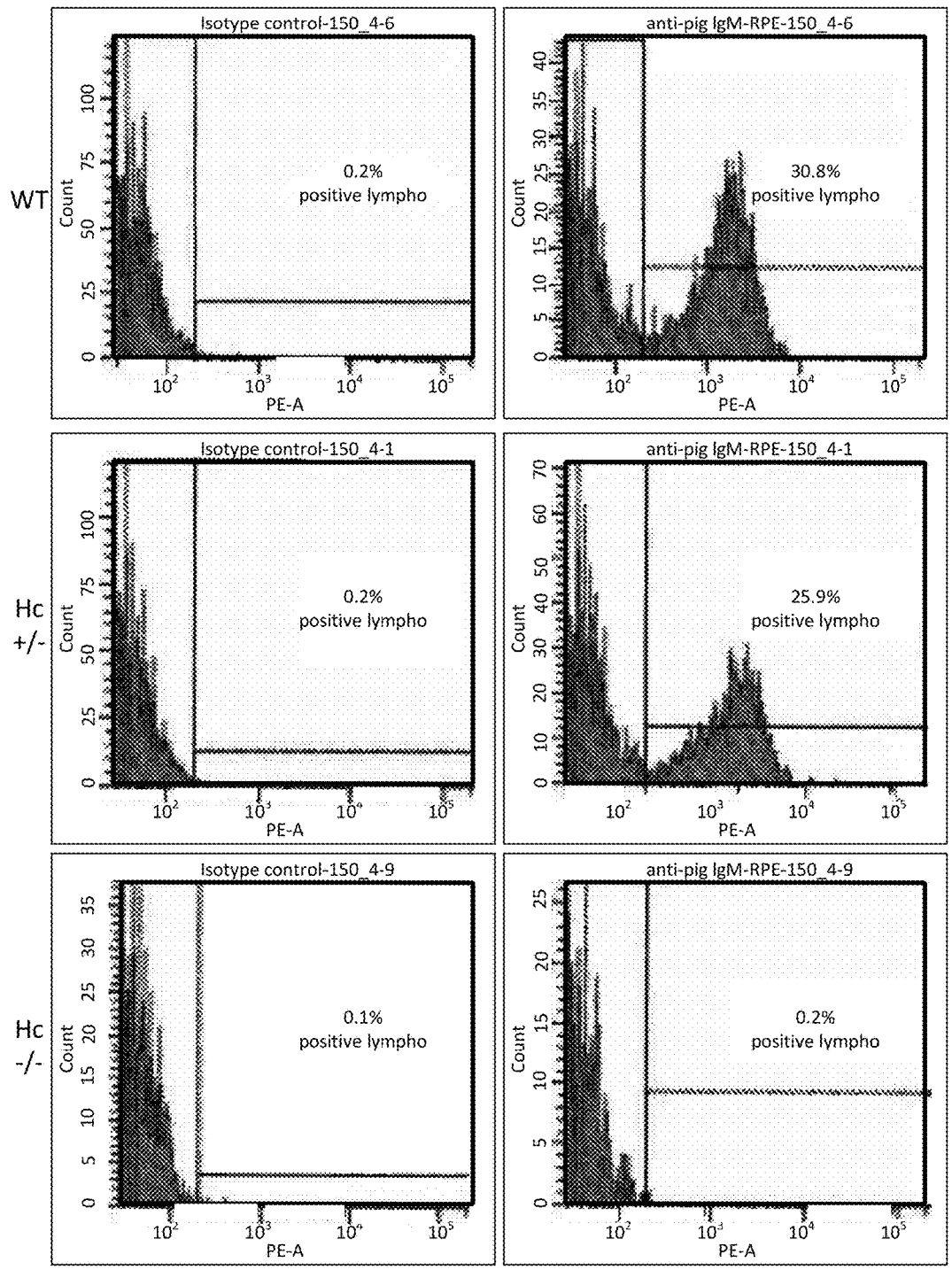
FIG. 3 shows a flow cytometry analysis of pig blood samples devoid of red blood cells stained with either anti-porcine Hc Ab (clone M160) or mouse IgG1 isotype control and analyzed by flow cytometry. Pig WBCs were stained with mouse anti-porcine Hc (clone M160) Ab or mouse IgG1 isotype control. Cells were washed and stained with fluorescently labeled goat anti-mouse IgG1. Shown is a representative histogram of a WT littermate pig (piglet number 6, top row), which had 30.8% IgM+ cells (PE-A) in the gated lymphocyte population determined on the scatter plot. A representative heterozygous Hc KO (Hc +/−) pig (piglet number 1, middle row) had a less IgM+ percentage in the same gate (25.9%). Also shown is a representative Hc −/− pig (piglet number 9, bottom row), which had nearly nil IgM expression (just like the isotype control).
Figure 8:
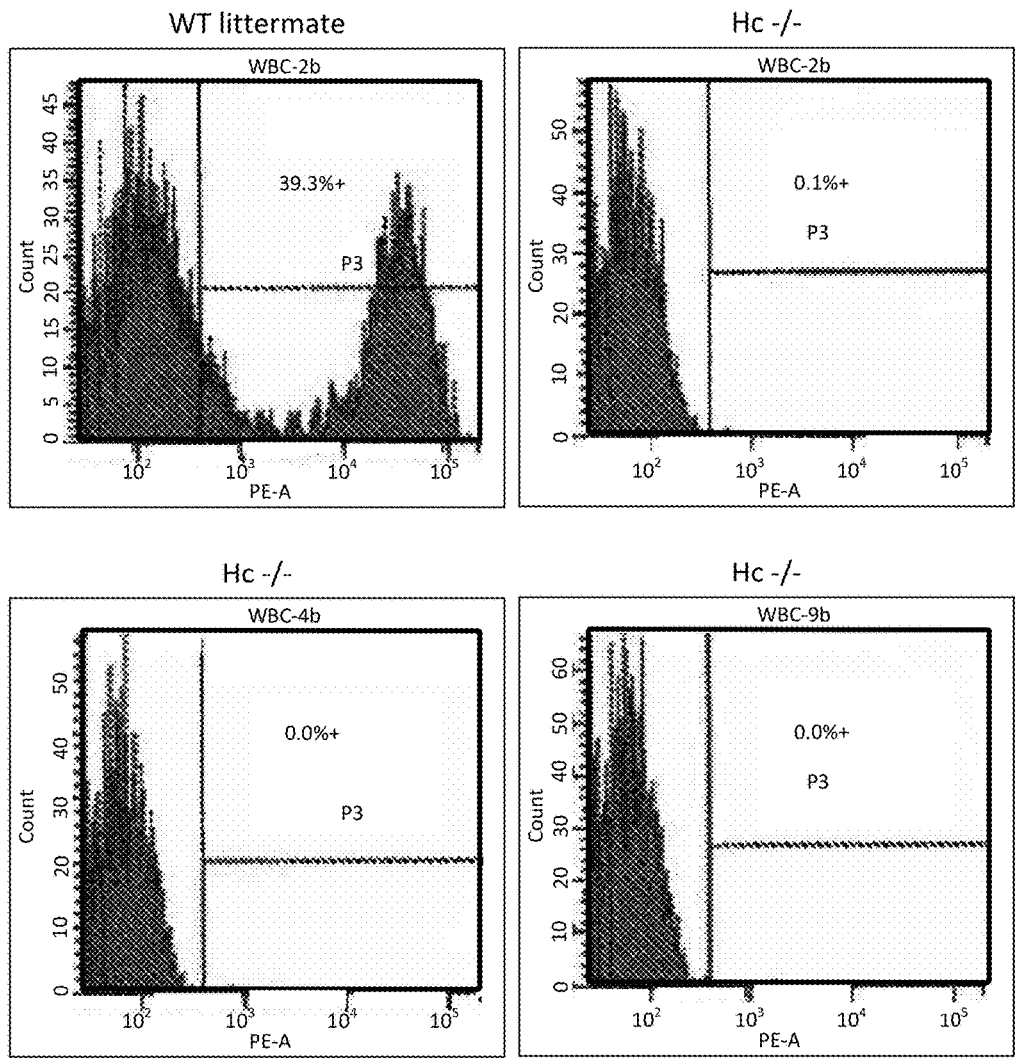
FIG. 8 shows immunofluorescence staining of IgM+ lymphocytes isolated from one WT (Hc +/+) and three Hc −/− piglets. Piglets were sampled at 8 weeks of age, after they had been weaned (weaned at 4 weeks of age). The Hc −/− piglets had no detectable IgM+ lymphocytes.

Porcine white blood cells (WBCs) were stained with either anti-porcine Hc Ab (clone M160) or mouse IgG1 isotype control and analyzed by flow cytometry. No lymphocytes expressing IgM on their surface were found in the Hc −/− pigs (FIG. 3). In contrast at the Hc +/+ piglet showed 30.8% IgM+ lymphocytes, and the six Hc +/− piglets had a range of 16.8% to 25.9% IgM+lymphocytes (data not shown). Similar data was obtained in subsequent litters that were allowed to suckle, reared normally, and weaned at 4 weeks of age. Flow cytometry was performed on piglets from these littersat 8 weeks of age and no Hc −/− pigs had any detectable IgM+ lymphocytes (FIG. 8)

Measurement of Hc, Light Chain and T Cell Transcription.

Transcripts encoding porcine IgM, IgG and IgA were amplified by RT-PCR from splenic RNA using the primer sets described in Table 2 and previously (Butler et al (2001) J Immunol 167, 3239-3249).

TABLE 2

Primers used for amplification of Ig Hc and TcR sequences by PCR

| Isotype | First round PCR Forward | Second round PCR Forward | Reverse |
|---|---|---|---|
| Cμ | gaggagaagctggtggagt | tctcctgtgttggctctgg | ggggacgaagatgttcaagac* |
| Cγ | gaggagaagctggtggagt | tctcctgtgttggctctgg | ccaccaccacgcacgtga |
| Cα | gaggagaagctggtggagt | tctcctgtgttggctctgg | gagccccggagcaggtct* |
| TCRβ3 | leader mix # | | tctccgcttccgatggttca |

*The two round Hc PCR was hemi-nested and used the same reverse primer.
The leader mix consists of a mixture of three primers that will together amplify all TCRβ families. These leader sequences are atgkgcatcggggtkctctg, atgsgctccakgctcctttg, and atgctcaccgggaacctttg.

These primer sets generated diagnostic PCR products that have been confirmed by sequence analyses. Those used for amplification of T cell Receptor (TcR)β were also used. Primer sequences can be found in Table 2.

Figure 4A:
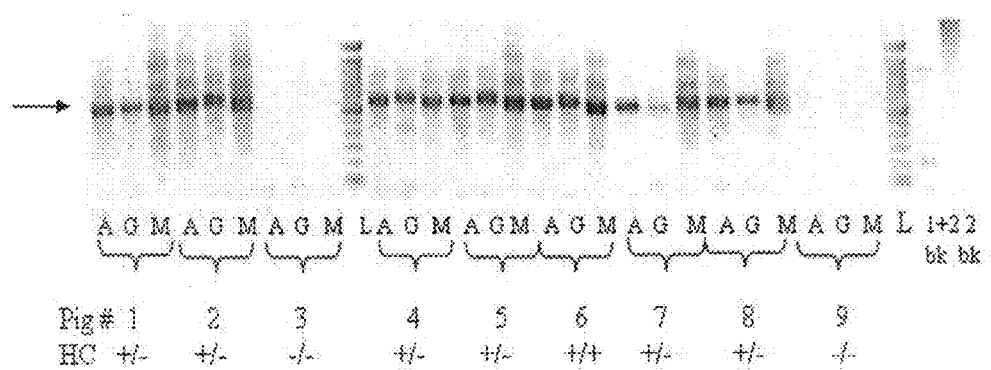
FIG. 4A is an image showing RT-PCR recovery of splenic transcripts encoding IgA (A), IgG (G) and IgM (M) in piglets 1-9 of various genotypes. The Hc genotype is indicated, which corresponds to piglets 1-9 as listed in Table 1. Negative controls for the first round PCR (bk 1+2) and the second round (bk 2) are indicated together with a polynucleotide length ladder (L).
Figure 4B:
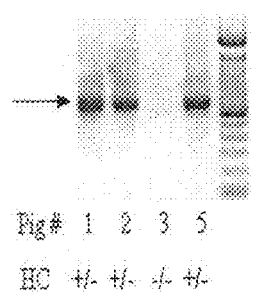
FIG. 4B is an image showing RT-PCR recovery of transcripts for IgM in the WBCs of chosen piglets.
Figure 4C:
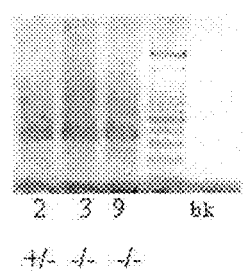
FIG. 4C shows RT-PCR recovery of TCRβ transcripts from chosen piglets.

Analysis of transcription of different Ig isotypes have shown that piglets of the Hc −/− genotype lack transcripts for IgA, IgG and IgM in spleen (FIG. 4A) and lymph node (LN; data not shown). The transcripts for IgM are also lacking from the Hc −/− animals but not in Hc +/− WBCs. Since transcription and expression of IgG and IgA depend on B-cells initially expressing IgM in order to undergo isotype class switching, only IgM transcription was tested in pig blood cells. RT-PCR results also show that disruption of the Hc locus did not result in any detectable differences in the transcription of TCRβ (FIG. 4C). Due to the vast number of TcRβ family members and the multiple primer sequences used here for TcRβ RT-PCR, many bands with different sizes were expected, preventing the formation of a distinctly sharp banding pattern.

Measurement of Plasma Ig.

Sandwich ELISAs were performed on heparinized plasma samples from the piglets to quantify levels of porcine IgM, IgG and IgA using well-established procedures (Butler et al (2000) Immunology 100, 119-130), These procedures have low limits of detection of 0.4, 0.4 and 0.6 ng/ml, respectively for the porcine Igs.

The level of serum IgM, IgG, and IgA was determined by ELISA in Hc +/+, Hc +/−, and Hc −/− piglets. Data in table 1 confirmed that pigs of the Hc −/− genotype failed to synthesize Ig for secretion, corroborating the lack of IgM+ cell surface expression by flow cytometry. Hc +/− pigs showed a range of Ig serum levels (Table 1). Variability in Ig production levels has previously been observed within standard WTpiglets used in agriculture (J. E. Butler, personal communication).

Histology, Immunohistochemistry, and Immunofluorescence.

Mesenteric LNs were removed and were either fixed in 10% formalin or frozen down in blocks of OCT (Electron Microscopy Sciences, Hatfield, Pa.). Formalin fixed tissues were blocked in paraffin and cut at 5 μm for staining with Hematoxylin and Eosin (H+E) staining or automated immunohistochemistry (IHC). H and E staining was performed using standard procedures. Automated IHC staining using alkaline phosphatase as the substrate was performed for pig B and T markers using the Ventana™ system following manufacturer's instructions. Pig B-cells were stained using a mouse anti-human CD79 alpha Ab (mouse IgG1; clone HM57; DakoCytomation, Carpinteria, Calif.). Pig T cells were stained with a rabbit anti-human CD3 (rabbit IgG; DakoCytomation). Both markers cross-react with the homologous proteins in the pig. Frozen sections were cut at 5 μm on a cryostat and were stained with anti-porcine kappa light chain 27.2.1, anti-porcine lambda light chain 27.7.1 (Sinkora et al., (2001) Veterinary immunology and immunopathology 80, 79-91) and anti-porcine IgM M160. All were mouse IgG1 isotype monoclonal Abs. Mouse IgG1 (mouse IgG1; clone MOPC-31C) was used as an isotype control. Immunofluorescent (IF) staining was performed using a 3-step procedure. Frozen sections were dried and fixed in cold acetone (Sigma), followed by avidin-biotin blocking (Invitrogen). Secondary Ab host species serum blocking steps were also included (Jackson ImmunoResearch). Primary Abs were diluted in antibody diluent (Invitrogen) and incubations were performed for 1 h at room temperature in a humidified chamber. The secondary Ab used was biotinylated donkey anti-mouse IgG (Jackson ImmunoResearch). The tertiary Ab used was fluorescein-conjugated strep avidin (Jackson ImmunoResearch). Slides were washed in PBS between steps, were cover slipped using 22×30 mm coverslips (VWR, West Chester, Pa.) and were preserved using Slowfade with DAPI (Invitrogen). Representative histological and IHC pictures were taken using a Nikon Digital Sight DS-L1 camera on a Nikon Eclipse E400 microscope, and analyzed using Nikon ACT-1 software (Nikon, Melville, N.Y.). Representative IF pictures were taken using an Olympus DP71 camera on a Provis microscope, and analyzed using DP controller software (Olympus, Center Valley, Pa.).

Figure 5:
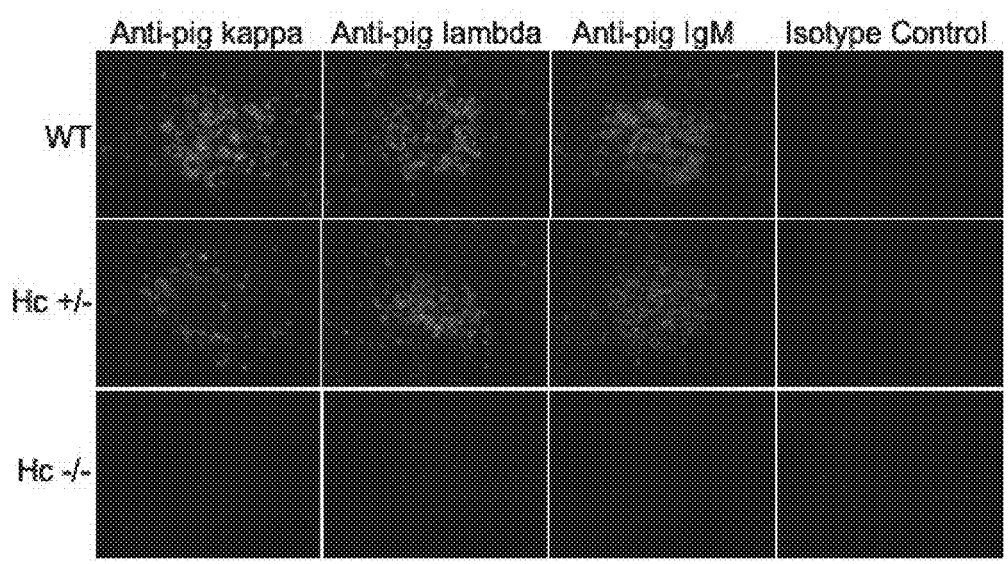
FIG. 5 shows representative immunofluorescence staining of mesenteric lymph nodes (LNs) of WT, Hc +/−, and Hc −/− piglets within a litter. Mesenteric LNs were removed and stained with anti-porcine kappa light chain, anti-porcine lambda light chain, anti-porcine IgM, or an isotype control. In the WT piglet (top row), staining for either light chain and for IgM are positive in LN follicles. In Hc +/− piglets (middle row), a similar staining pattern can be found. In Hc −/− piglets (bottom row), there is no staining for either light chain or IgM. Magnification 200×. All primary Abs were mouse IgG1 isotype.

Immunofluorescence (IF) staining was subsequently performed on LNs, to confirm that the lack of any secondary lymphoid tissue-bound B-cells expressing any Hc or light chain Ig in Hc −/− pigs. This was done by staining for porcine IgM, and by staining for each of the two possible light chains, namely kappa and lambda. WT and Hc +/− LNs showed similar staining patterns in LN follicles. Hc −/− LNs showed negative staining for pig IgM, as well as, pig kappa or lambda light chain (FIG. 5).

The Hc −/− piglets showed no secreted Ig of any isotype (Table 1), no transcription of any Ig isotype (FIG. 4), and no kappa or lambda light chain-containing Ig (FIG. 5), proving that the Hc −/− are completely devoid of all isotypes of Tg, and all Tg protein chains (heavy or light chain), both surface and secreted.

Figure 6:
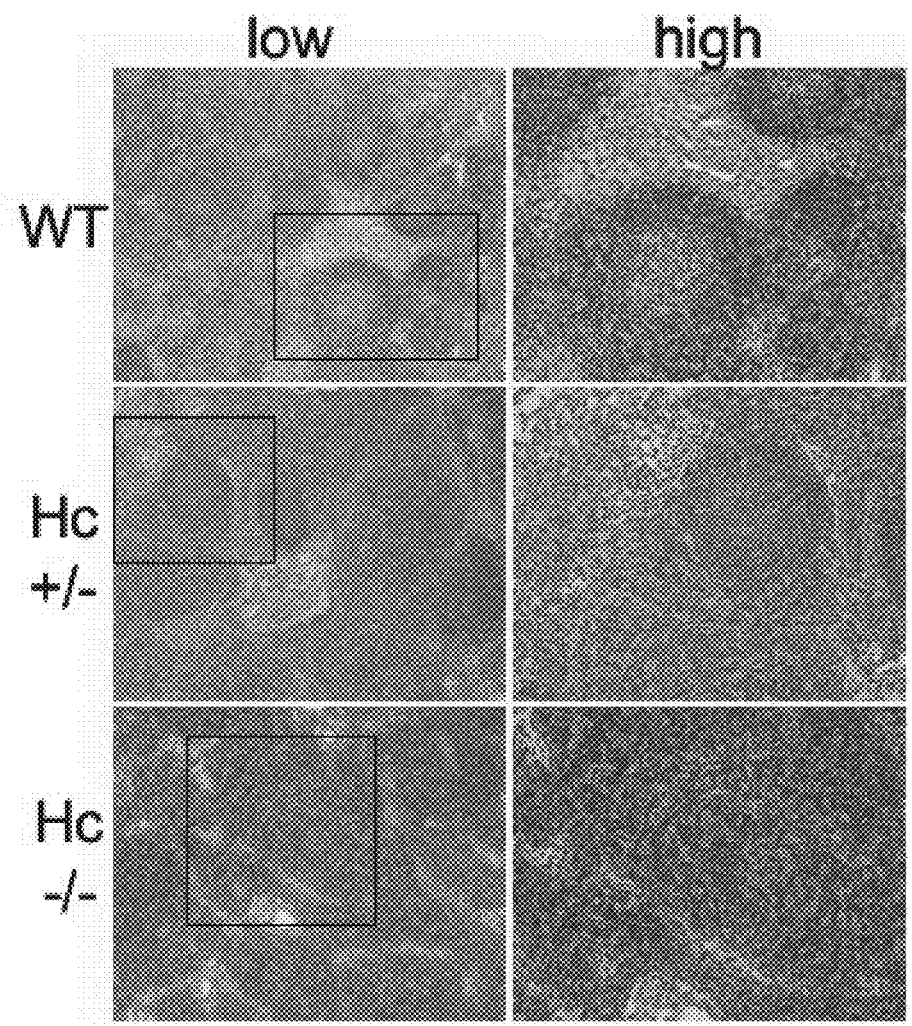
FIG. 6 shows representative H and E stains of mesenteric LNs of WT, Hc +/−, and Hc −/− piglets within a litter. Mesenteric LNs were removed and stained by H and E, and areas of follicular development were analyzed. In WT piglets (top row), follicles were developed and have a distinct germinal center. This is most visible at the higher magnification (high, 200×, right-hand side), which is shown in the lower magnification (low, 100×, left-hand side) in the black box. In Hc +/− piglets (middle row), follicles have structure but are not fully developed, and lack an intact germinal center. In Hc −/− piglets (bottom row), there is no distinguishable follicular or germinal center development.

Histologically, as shown in FIG. 6, many normal follicles were observed in the HC +/+ piglet. Follicles can be identified as organized structures in the medulla, predominately made up of a dense population of lymphocytes surrounding a less dense population of interspersed and centrally located antigen presenting cells (i.e. follicular dendritic cells in the germinal centerin contrast, a range of follicular structure organization and morphology was observed in the LNs of the Hc +/− piglets, including some nearly normally developed follicles and germinal centers, some follicular structures with seemingly underdeveloped germinal centers (as shown in FIG. 6), and some with scattered dense regions of lymphocyte populations showing little resemblance to follicles at all. In general, the diameter of the average follicle and size of the average germinal center is smaller in the Hc +/− piglets than in the Hc +/+ piglet. Significantly, no follicle formation or germinal center organization was observed in any of the Hc −/− piglets (FIG. 6).

Figure 7:
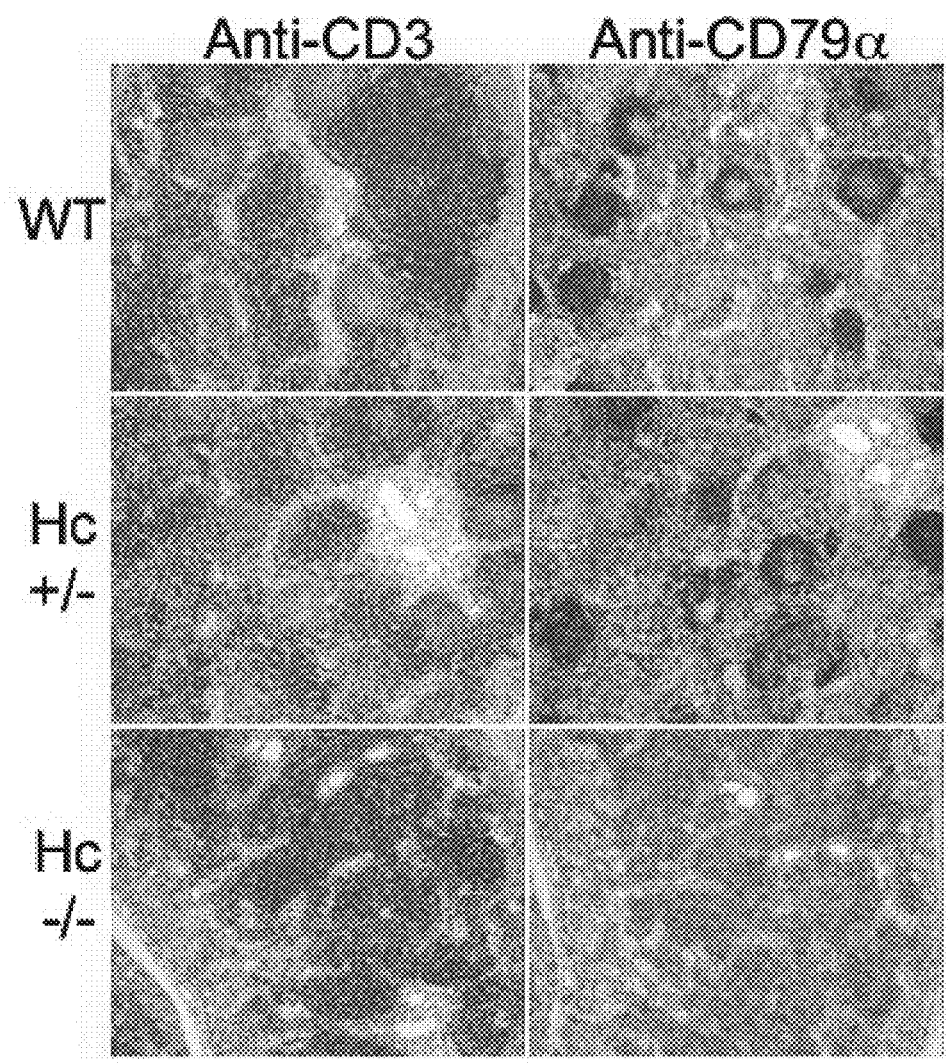
FIG. 7 shows representative immunohistochemisty (IHC) of LNs from WT, Hc +/−, and Hc −/− piglets within a litter. Mesenteric LNs were removed and stained with anti-human CD3 or anti-human CD79α, respectively, which cross react to the porcine CD3 and CD79α on T and B-cells respectively. In the WT piglet (top row), T cells surround the follicles. B-cells are found in the follicles, surrounding the follicular dendritic cells in the germinal centers. In Hc +/− piglets (middle row), a similar pattern of expression is found. In Hc −/− piglets (bottom row) piglets, there are no B-cells. T cell numbers look normal, but lack the structure of the follicular and germinal center development as shown in WT and Hc +/− LNs. Magnification 100×.

Immunohistochemistry (IHC) for T and B-cell markers was performed (FIG. 7). Clear, well defined follicular structures were observed in Hc +/+ LN, with B-cells tightly packed in and around the germinal centers, and T cells dominating the paracortical region between follicles. LN from Hc +/+ and Hc +/− LNs showed similar T and B-cell zone features. On the contrary, Hc −/− LNs were completely devoid of B-cells. T cell numbers appeared largely unaffected in the Hc −/− piglets, as compared to the other genotypes.

Hc −/− piglets also showed significantly altered lymphoid morphology (FIG. 6). In Hc +/+ LNs, B-cells become clustered into follicles, comprised primarily of B-cells and a specialized stromal cell, the follicular dendritic cell. Primary follicles have a complex network of these specialized antigen presenting cells, which form germinal centers that are known to make a central contribution to the selective events that underlie the Ab response. For B-cells to be activated they surround the germinal center, and T cells within zones present on the opposite side of the follicle, provide T cell help after antigen stimulation. The follicular structure was found to be impaired in Hc +/− piglets, and totally absent in Hc −/− piglets. The lack of B-cells in the Hc −/− piglets (FIG. 7) suggests that development of follicular structure is B-cell-dependent.

In addition, analysis of five of the Hc−/− piglets generated from breeding, allowed to suckle, and weaned at five weeks of age, which were necropsied one to eight weeks post-weaning showed the presence of opportunistic bactierial infections, no follicles or germinal centers in lymph nodes or spleen, and a paucity of Peyer's patches in the intestinal sub-mucosa.

Summary Phenotypic Analysis of HC −/− Pigs.

Hc −/− piglets had no serum Ig, and no IgM or Ig light chains expressed on circulating lymphocytes, or in lymphoid tissue. In addition, these Hc null pigs did not have transcripts for any major Ig isotype in LN or spleen, and no transcripts for IgM in WBCs. Hc −/− piglets were demonstrated to be devoid of B-cells, and had no observable follicular development in lymphoid tissue. Our results also showed that targeted deletion of both alleles in the Hc locus had no negative effect on transcription of the T cell receptor (specifically TcRß). Furthermore, Hc −/− LNs contained approximately the same proportion of T cells as WT littermate LNs by IHC, which indicates that Hc −/− pigs have an apparently normal T cell compartment.

Example 7: Production of Nude Pigs

The gene which is mutated in the mouse to cause the nude phenotype has been characterized and named whn or FOXN1 which stands for winged helix in nude or forkhead box N1 (Nehls et al., (1994) Nature 372, 103-107, Segre et al., (1995) Genomics 28, 549-559). It is also commonly referred to as the "nude" gene. The whn gene product is a transcription factor involved in the initiation and maintenance of the differentiated phenotype of thymic epithelial cells. It is also required for proper keratinization of the hair shaft (Schorpp et al., (1997) Immunogenetics 46, 509-515).

In the mouse the nude gene mutation is characterized as a one base pair (bp) deletion (of base G) in Exon 3 of the FOXN1/whn gene which causes a frameshift, such that transcription is terminated prematurely by a resulting stop codon in exon 6 (Nehls et al., (1994) Nature 372, 103-107). The exon 6 region of the mouse gene encodes the DNA binding domain of this transcription factor, therefore the point mutation causes a loss of the DNA binding domain therefore yielding a non-functional transcription factor. Similar mutations of the FOXN1 gene have also been described in the rat and human genes. The result of these mutations (in all species) is a hairless, athymic, immune-compromised phenotype (Coffer et al., (2004) Nature reviews 4, 889-899).

Mouse sequences for the FOXN1 (nude) gene are available in GeneBank (representative sequences include accession # X81593, mouse mRNA; accession # AL591131, mouse genomic DNA gene sequence). In addition, the mouse, rat and human FOXN1 (a.k.a. whn or nude) genes and their structure have been fully characterized, and the authors determined that the exon/intron structure of the human nude gene is in complete concordance with the mouse nude gene (Schorpp et al., (1997) Immunogenetics 46, 509-515). Thus it is expected that the porcine FOXN1/whn gene would share similar homology to the mouse gene as to human. Results from a BLAST analysis show the mouse mRNA is 85% homologous to mRNA isolated from a porcine (sus scrofa) skin cDNA library (GeneBank accession DB803240). Therefore using homologous DNA sequences as probes and published gene sequences, the porcine genomic FOXN1 (pFOXN1) gene can be cloned.

Using published mouse and human FOXN1 sequences and the porcine sequences identified by the BLAST search, PCR primers are designed and used to amplify porcine genomic DNA to produce genomic clones encompassing the areas of the porcine gene desired for gene targeting, to create a disruption or mutation in the pFOXN1 gene. The genomic clones are restriction mapped and used to design recombination arms for use in building the pFOXN1 targeting vector. A marker gene is built into the targeting design to allow for selection of targeted cells. These vectors are used in homologous recombination to disrupt or inactivate the pFOXN1 gene in primary porcine cells. Methods of cloning genes, designing gene targeting vectors, and gene targeting by homologous recombination in cells, and for production of gene targeted animals are known in the art (see e.g. Maniatis, et al. Molecular Cloning: A Laboratory Manual ($3^{rd}$ Ed.), Dai et al., (2002) Nature biotechnology 20, 251-255, U.S. Publication No. 2003-0024002).

In one method, the porcine gene is targeted with a replacement type targeting vector, such that following homologous recombination, the porcine genome has a mutant sequence comprising a one by (G) deletion in Exon 3 homologous to the mutation found in the nude mouse genome. In another method, the pFOXN1 gene is targeted such that areas of exons 5-7 which encode the DNA binding domain for the FOXN1 transcription factor (Schorpp et al., (1997) Immunogenetics 46, 509-515) are disrupted or deleted. As a result of these modifications to the porcine genome, no functional pFOXN1 transcription factor protein is transcribed, resulting in the mutant nude phenotype.

Porcine cells are transfected with the targeting vector(s) in vitro, to produce cells with disruptions of the pFOXN1 gene. Cells are isolated which have the correct targeting events using known techniques. Cells which are positive for the gene targeting event, are then used as nuclear donors in porcine nuclear transfer procedures (as detailed in Example 3) to produce pigs with the pFOXN1 gene deleted on one allele (heterozygous pFOXN1 KO) or both alleles (homozygous pFOXN1 KO). Heterozygous pFOXN1 KO (pFOXN1 (+/−)) pigs are bred to each other to produce homozygous pFOXN1 null pigs (pFOXN1(−/−)).

In certain cases, pFOXN1(+/−) cells, or cells isolated from pFOXN1(+/−) pigs or fetuses, can be utilized in a second round of gene targeting to target the other pFOXN1 allele, thus generating pFOXN1(−/−) porcine cells. These pFOXN1(−/−) cells are used as donors in nuclear transfer to produce pFOXN1(−/−) pigs.

Any of the pFOXN1 gene targeted porcine cells, or cells derived from heterozygous and homozygous pFOXN1 KO pigs, can be used for further rounds of genetic modification and nuclear transfer to introduce other desired genetic modifications. Alternatively, pFOXN1 KO pigs can be bred with other lines of genetically modified pigs in order to combine desired genotypes and/or phenotypes. For example, pigs such as RAG-1 KO pigs, described in US patent applications US20050155094 and WO03066855A1, can be crossed to the Hc KO pigs and/or pFOXN1 KO pigs. In another embodiment, the Hc KO pigs can be used with the pFOXN1 KO pigs and RAG-1 KO pigs in side-by-side studies to elucidate the roles of the various parts of the immune response (B and T cells) following a pathogenic challenge and/or following prophylactic treatments.

Example 8: Production and Characterization of Transgenic Pigs Expressing pCTLA4-Ig Transgenic pigs expressing a pCTLA4 transgene were produced. These pigs, which have a diminished T-cell response and an immunocompromised phenotype can serve as research animal models. A vector was constructed to produce pigs in which a secreted form of pCTLA4-Ig was constitutively over-expressed. There was robust expression and functionality of the transgene, which resulted in an immunocompromised phenotype in these animals.

Vector Construction

Figure 9:
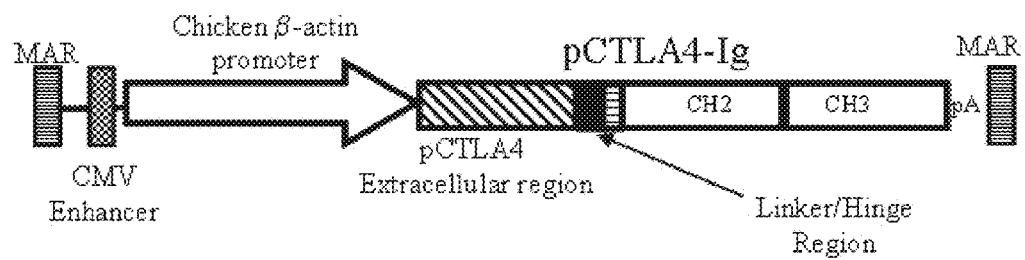
FIG. 9 is a diagram of the pCTLA4-Ig expression vector used to produce pCTLA4-Ig transgenic pigs. The extracellular region of pCTLA4, fused to the CH2/CH3 regions of human IgG1 was inserted into an expression cassette containing a CMV enhancer/chicken ß-actin promoter/rabbit globin intron as well as flanking insulator sequences.

An Asc1/Mlu1 restriction fragment coding for a pCTLA4-Ig fusion protein (Vaughn, et al., J Immunology, 165:3175-3181, 2000) that consisted of the extracellular region of pCTLA4 cDNA joined with the hinge and CH2 and CH3 regions of human IgG1 was inserted into a mammalian expression vector containing a CMV enhancer, chicken B-actin promoter, rabbit globin splice site, and insulator regions consisting of two matrix attachment regions (MARS) 21q21 MAR and ß globin MAR (FIG. 9).

Transfection

Primary fetal fibroblasts from wildtype (WT) or GTKO pigs were co-transfected by electroporation with 1 µg of linearized pCTLA4-Ig construct and either 0.1 µg pgkpuromycinr or pgkneomycinr vector. At 48 h, cells were seeded in 48-well plates at a concentration of 100-500 cells/cm2, and selected with either 250 µg/ml G418 (Gibco BRL, Grand Island, N.Y.) or 0.5 µg/ml puromycin (InvivoGen, San Diego, Calif.). Selected clones were screened for the pCTLA4-Ig transgene by polymerase chain reaction (PCR), and positive clones were pooled and used for nuclear transfer.

Nuclear Transfer

The nuclear transfer procedure used has been described (Dai, et al., (2002) Nature biotechnology 20, 251-255). Briefly, in vitro matured oocytes were enucleated at metaphase II and a single fibroblast cell of WT large white crossbred lineage or GTKO of large white origin, was placed between the zona pellucida and the cytoplasm of each enucleated oocyte. Fusion and activation were induced with an electric pulse (1.4 kV/cm). Embryos were transferred to the oviduct of an estrus-synchronized recipient gilt within 1-4 h post-activation.

Animal Husbandry

All animals except those for one litter were farrowed in segregated housing to minimize exposure to pathogens. The other litter which was on a WT background, was farrowed in a standard pig barn with no segregation from other pigs. Some litters received feed containing tetracycline (110 g tetracycline/kg of feed) starting at birth and continuing until euthanasia. All animals that showed signs of infection received treatment with 2.5 mg/kg body weight Draxxin (Pfizer, New York, N.Y.) and 15 mg/kg body weight Nuflor (Schering-Plough, Kenilworth, N.J.).

Over a period of approximately 6 weeks, 5 litters farrowed, resulting in a total of 20 piglets. Three litters (11 piglets) resulted from SCNT using WT/pCTLA4-Tg transgenic cells, and two litters (9 piglets) were produced with GTKO/pCTLA4-Ig cells. All were live births except for two piglets in one WT background litter. With a few exceptions, birth weights were in the normal range. At birth, the animals nursed well and appeared in good health. Eight of the 11 WT piglets and seven of the nine GTKO piglets were positive for the pCTLA4-Ig transgene by Southern analysis (not shown), a 75% transgenesis rate.

Polymerase Chain Reaction (PCR) Analysis

PCR screening of transfected cells was performed in 96-well plates. Cells were disrupted in a lysing solution consisting of 50 mM Tris (pH 8.0), 0.15M NaCl, 10 mM EDTA, 1% sodium dodecyl sulfate (SDS), 25% sodium perchlorate, 1% 2-mercaptoethanol, and 200 µg/ml proteinase K. DNA isolated from pig tail samples was used for PCR and Southern analysis and was purified by a modified Marmur procedure (Marmur, J et al., J Mol Biol, 3:208-218, 1961). The PCR primers were designed to amplify a fragment which flanked the junction of the promoter and CTLA4-Ig coding sequence.

Western Blot Analysis

Tissue and cell lysates were prepared by homogenization in the presence of protease inhibitors (Then-no Scientific, Rockford, Ill.) followed by the addition of SDS to a final concentration of 1% and centrifugation to remove residual cellular debris. Protein concentration was determined with a BCA protein assay kit (Pierce, Rockford, Ill.). Heat denatured samples (10-20 ug protein) were fractionated on 4-12% BisTris SDS gradient gels (Invitrogen, Carlsbad, Calif.) under reduced conditions. Recombinant human CTLA4-Ig/Fc (R and D Systems, Minneapolis, Minn.) was used as a standard control protein. Following electrophoresis, proteins were transferred to a nitrocellulose membrane, stained with Memcode Protein Stain (Thermo Scientific, Rockford, Ill.) for total protein visualization, and blocked with casein-blocking buffer (Sigma-Aldrich Co., St. Louis, Mo.). The blocked membrane was incubated in rabbit anti-human IgG1-HRP (Binding Site, San Diego, Calif.), which recognizes the human IgG1 heavy chain region of pCTLA4-

Ig. Immunoreactive bands were detected with Super Signal West Pico Chemiluminescent Substrate (Thermo Scientific, Rockford, Ill.) and photographic imaging.

All pigs that were transgenic by Southern blot analysis for pCTLA4-Ig also expressed the transgene. Western blot analysis of tail lysates (FIG. 10a) indicated robust expression in all animals, albeit at different levels, with a major band of approximately 56 kDa under reduced and denatured conditions. In general, organ lysates also exhibited high levels of expression, including aorta, spleen, heart, lung, kidney, liver, and pancreas (FIG. 10b)).

Pig CTLA4-Ig Quantitative ELISA pCTLA4-Ig in transgenic pig serum was quantitated in an ELISA assay. Capture antibody was sheep anti-human IgG1 (The Binding Site, San Diego, Calif.) at 5 ug/ml. A standard curve was generated using hCTLA4Fc (R&D Systems Inc., Minneapolis, Minn.). Appropriate dilutions of sample pig sera were loaded in triplicate on the plate and incubated for 1 h at room temperature. Horseradish perixidase (HRP)-conjugated sheep anti-human IgG1 (The Binding Site, San Diego, Calif.) was added at 1:5000 dilution and incubated for 1 h at room temperature. Peroxidase substrate 3,3',5,5'-tetramethyllbenzidine (TMB) (Sigma-Aldrich Co., St. Louis, Mo.) was added for color development.

Figure 13:
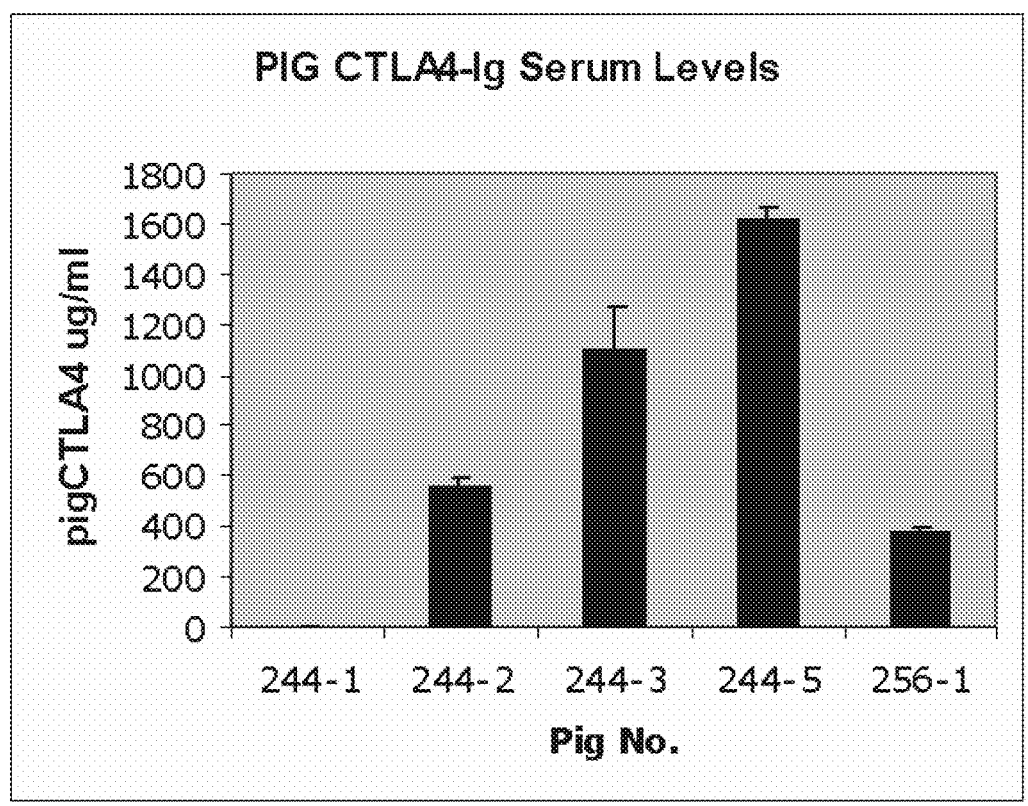
FIG. 13 is an ELISA analysis of serum pCTLA4-Tg levels (μg/ml) in pCTLA4Ig pigs.

Serum concentrations of pCTLA4-Ig were quite high in all transgenic pigs, ranging from approximately 380 to 1600 ug/ml serum (FIG. 13).

Pig IgG and IgM Quantitative ELISA

Pig serum IgG and IgM was quantitated using commercial pig IgG and IgM ELISA kits (Bethyl Laboratories, Montgomery, Tex.), which included all antibodies and reference serum. Capture antibodies were goat anti-pig IgG and goat anti-pig IgM at 1:100 dilution. A reference pig serum supplied with the kit was used to prepare dilutions for a standard curve. Appropriate dilutions of sample pig sera were loaded in triplicate on the plate and incubated for 1 h at room temperature. Goat anti-pig IgG-HRP or goat anti-pig IgM-HRP at 1:20000 dilution was added to the wells and incubated for 1 h at room temperature. TMB was added for color development.

Figure 12A:
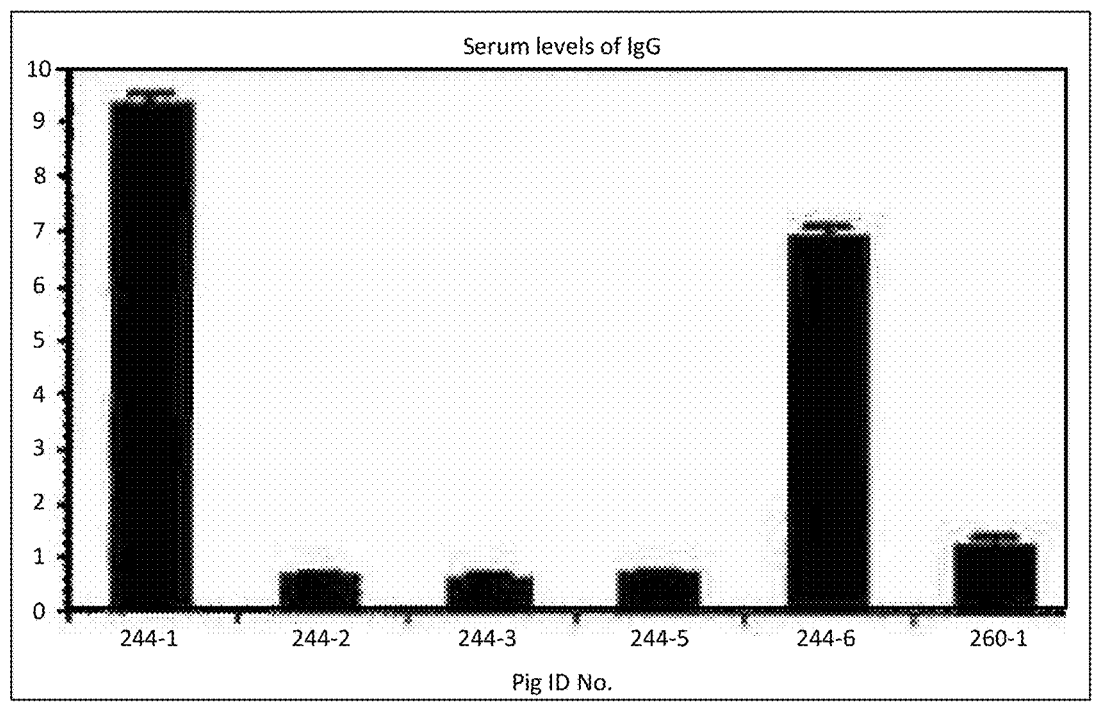
FIG. 12 shows ELISA analyses of serum IgG levels (mg/ml) (FIG. 12A) and serum IgM levels (mg/ml) (FIG. 12B) in pCTLA4Ig pigs. Pigs 244-1 and 244-6 are non-transgenic littermates.
Figure 12B:
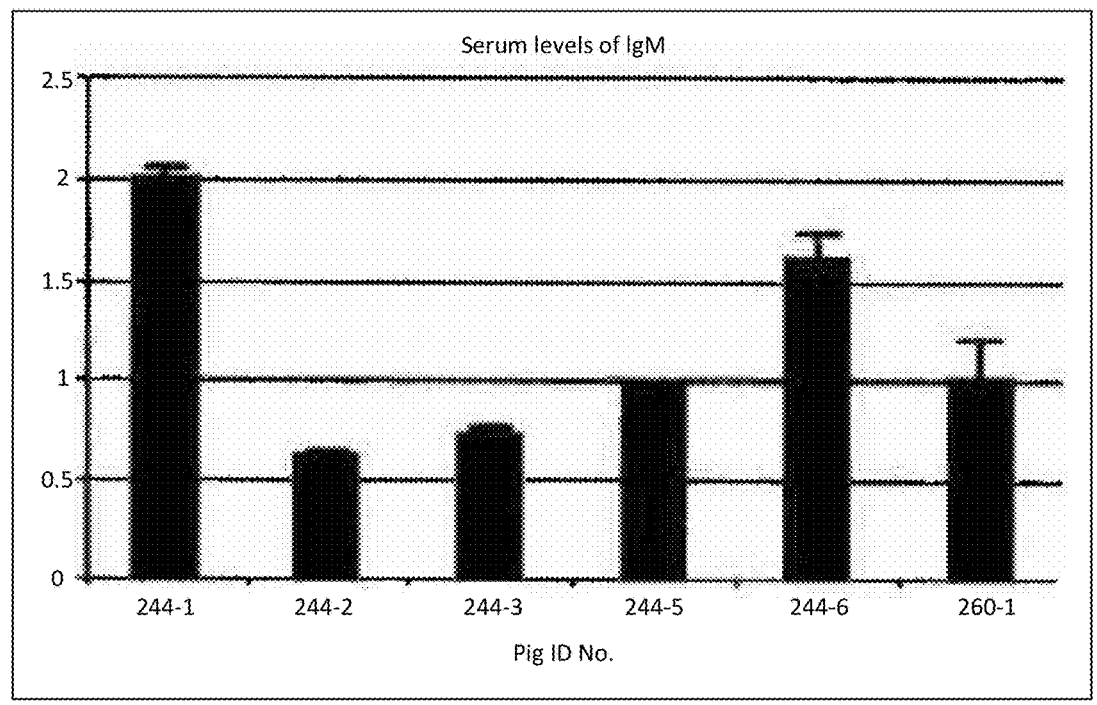

Serum concentrations of IgG and IgM were depressed in the pCTLA4-Ig pigs (FIG. 12). IgG levels were approximately 10-fold lower than their nontransgenic littermates (piglets 244.1 and 244.6 in FIGS. 12a and 12b). IgM was depressed as well, in some cases to less than half the level of a nontransgenic sibling. All transgenic animals, independent of housing or antibiotic treatment, had this characteristic serum IgG and IgM profile.

Hematology

A standard panel of hematology tests was performed on selected animals at the Virginia-Maryland Regional College of Veterinary Medicine, Virginia Polytechnic Institute and State University, Blacksburg, Va.

Hematological analysis indicated that, in litters raised without antibiotic treatment, transgenic pigs, in contrast to their non-transgenic littermates, had low white blood cell counts, ranging from 53% to 71% of normal levels. Lymphocyte counts were also subnormal in these animals, ranging from 14% to 61% of normal levels. Transgenic pigs treated with antibiotics maintained normal levels of white blood cells and lymphocytes.

Necropsy

Necropsies were performed on selected animals by the staff veterinarian at Revivicor, Inc, at the Virginia-Maryland Regional College of Veterinary Medicine, or at the College of Veterinary Medicine at Iowa State University, Ames, Iowa.

Three of these animals were necropsied; in all three cases, a diagnosis of septicemia was made. In one case, *Streptococcus equisimilis*, an opportunistic pathogen, was isolated as the causative agent. No organisms were cultured from the other two necropsies; in these cases, the diagnosis was based on histological findings or gross pathology. Since such acute infections developed within a few weeks after weaning, maternal antibodies transmitted in colostrum may have provided transient protection to these immunocompromised piglets. The pathogens believed to be the causative agents for the purulent infections seen in at least two of these animals are normal bacterial flora at our pig facility, but none of the nontransgenic littermates showed any sign of illness, despite their close proximity to the infected animals.

Features of septicemia at necropsy in three pCTLA4-Ig/WT pigs and the results of serological analysis, in particular the profoundly diminished serum IgG levels, indicated a severely immunocompromised status, and necessitated the addition of antibiotics to the feed as well as modified housing arrangements to minimize the chance of infection.

Histology

Heart, pancreas, kidney, and liver tissues from selected animals were processed and frozen in OCT compound (Electron Microscopy Sciences, Hatfield, Pa.) in cyromolds and stored at −70° C. Frozen sections (6 µm) were cut for immunofluorescent staining by the Virginia/Maryland Center for Veterinary Medicine onto positively-charged slides. Sections were fixed in acetone (Sigma, St. Louis, Mo.) and blocked with the avidin/biotin blocking kit (Invitrogen, Carlsbad, Calif.) as well as donkey serum (Jackson Immunoresearch, Westgrove, Pa.). Sections were stained with sheep anti-human IgG1 (The Binding Site, San Diego, Calif.) or sheep IgG isotype control (Jackson Immunoresearch, Westgrove, Pa.) for 1 h at room temperature in a humidified chamber. A biotinylated donkey anti-sheep IgG antibody was used as the secondary (Jackson Immunoresearch, Westgrove, Pa.) in both experimental and control samples. A fluorescein-conjugated streptavidin ((Jackson Immunoresearch, Westgrove, Pa.) was used as the tertiary antibody. Sections were preserved in Slow Fade (Invitrogen, Carlsbad, Calif.) and coverslipped for viewing under the Olympus Provis microscope and DP71 camera. Pictures were taken using the DP software (Olympus, Center Valley, Pa.).

Figure 11:
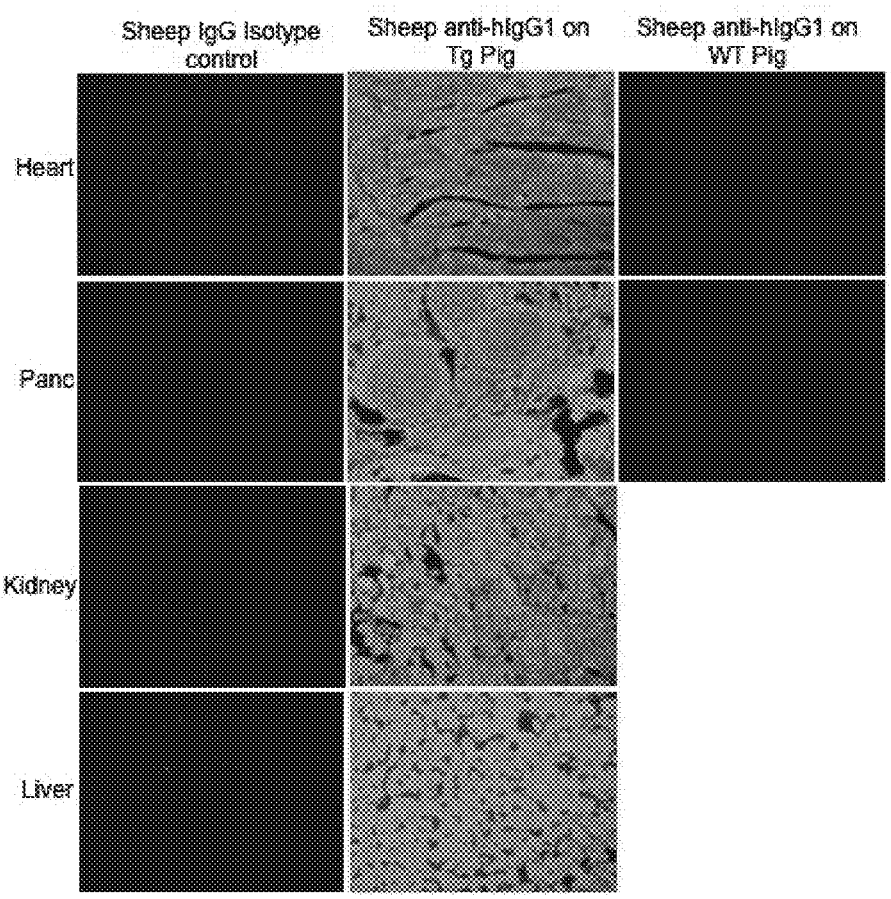
FIG. 11 shows immunofluorescent staining for human IgG1 in organ sections of tissues from a pig transgenic for pCTLA4-Ig. All tissues showed intense uniform staining, indicating that all tissue types expressed and secreted pCTLA4-Ig.

Piglet 264.4 was positive by Western for pCTLA4-Ig in all tissues tested; therefore immunofluorescence was employed to visualize and more specifically localize expression in tissues relevant to xenotransplantation, including heart, pancreas, kidney, and liver (FIG. 11). Expression was found to be intense and uniform in all tissues and in all cell types (which was expected from the CAG constitutive promoter). Control tissues from WT littermates were negative for human IgG1. pCTLA4 piglet isotype controls had minor background expression due to the polyclonal nature of the primary antibody and the minor cross-reactivity of sheep IgG with immunoglobulins of other species, such as human IgG1. This was most prominent in the heart.

These results demonstrate that overexpression of pCTLA4-Ig in transgenic pigs can produce an immunosuppressed phenotype. These animals showed decreased levels of immunoglobulins (IgG and IgM). It is likely that the high levels of pCTLA4-Ig produced in the blood and organs of these animals could have impacted T-cell-dependent B cell proliferation and differentiation and subsequent antibody production. By breeding, assisted reproduction, or a combination of transgenic strategies, pCTLA4-Ig transgenic pigs could be combined with knockout of the pig HC gene, to produce an animal with deficiencies in both T cell and B cell function. Such an animal would have broad utility as a model for the study of immune reactions in pigs, as well as, for studying both humoral and cell mediated reactions to pathogens, antigens, and for vaccine development.

Example 10: Testing of Vaccines

Pigs will be colonized with LA or LGG, inoculated with the AttHRV vaccine, and challenged with VirHRV. One group will be intravenously injected with an anti-CD8 mAb (anti-CD8α) ascites at 6, 5, 4, 3, 2, and 1 days (PID 22-27) before VirHRV challenge (PID 28) to completely deplete CD8 T cells. Ascites will be ordered from ImmunoPrecise (Victoria, Canada). After a single intravenous injection of the anti-pig CD8 mAb ascites (0.7 ml/kg), the frequencies of CD8+ T cells in blood of the pigs is reduced to the lowest levels (0-5% of total cells) at 4-6 days post injection. The completeness of CD8+ and CD4+CD8+ T cell depletion, and frequencies of CD4+ T cells will be monitored by flow cytometry. Rotavirus-specific IFN-γ+CD4+ and IFN-γ+ CD8+ T cell, CD4+IL-13+ Th cell and Treg cell responses will be measured at PID 28 and PCD 7. Th1, Th2, and Th3 cytokine levels in serum will be measured at PID 0, 10, 21, 28, and PCD 2 and 7. Virus shedding and diarrhea will be monitored daily from PCD 0-7. Viremia will be monitored on PCD 2 and 7.

The invention claimed is:

1. A method of characterizing the cellular immune response of an animal to an antigen comprising:
   (i) providing a genetically modified porcine animal lacking expression of functional porcine heavy chain immunoglobulin;
   (ii) administering the antigen to the animal;
   (iii) characterizing the cellular immune response of the animal to the antigen, wherein the porcine lacks expression of functional porcine heavy chain immunoglobulin due to a targeted disruption in both alleles of the porcine heavy chain (Hc) gene, which results in a lack of B-cell production in the porcine.

2. The method of claim 1 wherein the porcine has a disruption in at least one additional native gene in its genome.

3. The method of claim 1, wherein the porcine includes at least one xenogenous gene or transgene.

4. The method of claim 3, wherein the porcine expresses at least one xenogenous protein from the xenogenous gene or transgene.

5. The method of claim 4, wherein the protein is a costimulatory blockage molecule.

6. The method of claim 5, wherein the costimulatory blockage molecule is cytotoxic T-lymphocyte associated protein 4 (CTLA4).

7. The method of claim 6, wherein the CTLA4 is fused to an immunoglobulin (Ig) molecule.

8. The method of claim 1 wherein the antigen comprises an infectious agent or surface antigen thereof.

9. The method of claim 8, wherein the infectious agent is a virus.

10. The method of claim 1, wherein the porcine has a disruption in at least one additional native gene in its genome and wherein the additional native gene is an a-1,3-galactosyltransferase gene.

11. The method of claim 1, wherein the porcine has a disruption in at least one additional native gene in its genome and wherein the additional native gene is a CMP-Neu5Ac hydroxylase gene.

12. A method of characterizing the cellular immune response and course of infection in a porcine animal that has been treated with a prophylactic or therapeutic medicament against an infectious agent comprising:
   (a) exposing the porcine animal to the infectious agent or surface antigen thereof;
   (b) treating the porcine with the medicament; and (c) characterizing the cellular immune response and course of infection in the porcine to assess the effectiveness of the medicament, wherein the porcine animal is genetically modified to lack expression of functional porcine heavy chain immunoglobulin due to a targeted disruption in both alleles of the porcine heavy chain (Hc) gene, which results in a lack of B-cell production in the porcine.

13. The method of claim 12, wherein the medicament is a vaccine.

14. The method of claim 9, wherein the porcine further expresses an exogenous protein.

15. The method of claim 1 or claim 12, wherein the porcine has a targeted disruption in both alleles of the J6 joining region of the porcine heavy chain gene.

16. The method of claim 1 or claim 12, wherein the porcine has a targeted deletion of the J6 joining region of the porcine heavy chain gene.

\* \* \* \* \*

```
                               SEQUENCE LISTING

<160> NUMBER OF SEQ ID NOS: 19

<210> SEQ ID NO 1
   <211> LENGTH: 26
   <212> TYPE: DNA
   <213> ORGANISM: Artificial Sequence
   <220> FEATURE:
   <223> OTHER INFORMATION: primer

<400> SEQUENCE: 1
tctagaagac gctggagaga ggccag                                           26

<210> SEQ ID NO 2
   <211> LENGTH: 25
   <212> TYPE: DNA
   <213> ORGANISM: Artificial Sequence
   <220> FEATURE:
   <223> OTHER INFORMATION: primer

<400> SEQUENCE: 2
taaagcgcat gctccagact gcctt                                            25

<210> SEQ ID NO 3
   <211> LENGTH: 22
   <212> TYPE: DNA
   <213> ORGANISM: Artificial Sequence
   <220> FEATURE:
   <223> OTHER INFORMATION: primer

<400> SEQUENCE: 3
catcgccttc tatcgccttc tt                                               22

<210> SEQ ID NO 4
   <211> LENGTH: 22
   <212> TYPE: DNA
   <213> ORGANISM: Artificial Sequence
   <220> FEATURE:
   <223> OTHER INFORMATION: primer

<400> SEQUENCE: 4
aagtacttgc cgcctctcag ga                                               22

<210> SEQ ID NO 5
   <211> LENGTH: 312
   <212> TYPE: DNA
   <213> ORGANISM: Artificial Sequence
   <220> FEATURE:
   <223> OTHER INFORMATION: synthesized

<400> SEQUENCE: 5
ggctgaagtc tgaggcctgg cagatgagct tggacgtgcg ctggggagta ctggagaagg      60
```

```
actcccgggt ggggacgaag atgttcaaga cgggggggctg ctcctctacg actgcaggca    120
ggaacggggc gtcactgtgc cggcggcacc cggccccgcc cccgcacag ccacaggggg     180 agcccagctc acctggccca gagatggaca cggacttggt gccactgggg tgctggacct    240
cgcacaccag gaaggcctct gggtcctggg ggatgctcac agagggtagg agcacccggg    300
aggaggccaa gt                                                        312
```

<210> SEQ ID NO 6
<211> LENGTH: 394
<212> TYPE: DNA
<213> ORGANISM: Artificial Sequence
<220> FEATURE:
<223> OTHER INFORMATION: synthesized

<400> SEQUENCE: 6

```
ctctgcactc actaccgccg gacgcgcact gccgtgctgc ccatggacca cgctggggag    60
gggtgagcgg acagcacgtt aggaagtgtg tgtgtgcgcg tgggtgcaag tcgagccaag   120
gccaagatcc aggggctggg ccctgtgccc agaggagaat ggcaggtgga gtgtagctgg   180
attgaaaggt ggcctgaagg gtggggcatc ctgtttggag gctcactctc agccccaggg   240
tctctggttc ctgccggggt ggggggcgca aggtgcctac cacaccctgc tagcccctcg   300
tccagtcccg ggcctgcctc ttcaccacgg aagaggataa gccaggctgc aggcttcatg   360
tgcgccgtgg agaacccagt tcggcccttg gagg                               394
```

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7

```
gaggagaagc tggtggagt                                                 19
```

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8

```
tctcctgtgt tggctctgg                                                 19
```

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9

```
ggggacgaag atgttcaaga c                                              21
```

<210> SEQ ID NO 10
<211> LENGTH: 19
<212> TYPE: DNA
<213> ORGANISM: Artificial Sequence
<220> FEATURE:
<223> OTHER INFORMATION: primer

```
<400> SEQUENCE: 10
gaggagaagc tggtggagt                                                 19

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
tctcctgtgt tggctctgg                                                 19

<210> SEQ ID NO 12
<211> LENGTH: 18
<212> TYPE: DNA
<213> ORGANISM: Artificial Sequence
<220> FEATURE:
<223> OTHER INFORMATION: primer

<400> SEQUENCE: 12
ccaccaccac gcacgtga                                                  18

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
gaggagaagc tggtggagt                                                 19

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
tctcctgtgt tggctctgg                                                 19

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
gagccccgga gcaggtct                                                  18

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
tctccgcttc cgatggttca                                                20

<210> SEQ ID NO 17
<211> LENGTH: 20
```

```
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (4)..(4)
<223> OTHER INFORMATION: "k" is either T or G
<220> FEATURE:
<221> NAME/KEY: misc_feature
<222> LOCATION: (15)..(15)
<223> OTHER INFORMATION: "k" is either T or G

<400> SEQUENCE: 17
atgkgcatcg gggtkctctg                                     20

<210> SEQ ID NO 18
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (4)..(4)
<223> OTHER INFORMATION: "s" is either G or C
<220> FEATURE:
<221> NAME/KEY: misc_feature
<222> LOCATION: (11)..(11)
<223> OTHER INFORMATION: "k" is either T or G

<400> SEQUENCE: 18
atgsgctcca kgctcctttg                                     20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
atgctcaccg ggaacctttg                                     20
```